(12) United States Patent
Lu et al.

(10) Patent No.: US 12,157,894 B2
(45) Date of Patent: Dec. 3, 2024

(54) ABIOTIC STRESS TOLERANT PLANTS AND METHODS

(71) Applicants: PIONEER OVERSEAS CORPORATION, Johnston, IA (US); SINOBIOWAY BIO-AGRICULTURE GROUP CO. LTD., Beijing (CN)

(72) Inventors: Guihua Lu, San Diego, CA (US); Guokui Wang, Beijing (CN); Guanfan Mao, Beijing (CN); Changgui Wang, Beijing (CN); Rongrong Jiao, Beijing (CN); Yu Zhang, Beijing (CN); Guangwu Chen, Beijing (CN); Jiantao Wang, Beijing (CN)

(73) Assignees: SINOBIOWAY BIO-AGRICULTURE GROUP CO LTD; PIONEER OVERSEAS CORPORATION

( * ) Notice: Subject to any disclaimer, the term of this patent is extended or adjusted under 35 U.S.C. 154(b) by 231 days.

(21) Appl. No.: 17/595,469

(22) PCT Filed: May 22, 2019

(86) PCT No.: PCT/CN2019/087910
§ 371 (c)(1),
(2) Date: Nov. 17, 2021

(87) PCT Pub. No.: WO2020/232660
PCT Pub. Date: Nov. 26, 2020

(65) Prior Publication Data
US 2022/0213499 A1 Jul. 7, 2022

(51) Int. Cl.
*C12N 15/82* (2006.01)
*C12N 9/22* (2006.01)

(52) U.S. Cl.
CPC .......... *C12N 15/8273* (2013.01); *C12N 9/22* (2013.01); *C12N 15/8213* (2013.01); *C12N 15/8218* (2013.01); *C12N 15/8261* (2013.01)

(58) Field of Classification Search
None
See application file for complete search history.

(56) References Cited

U.S. PATENT DOCUMENTS

2013/0125258 A1* 5/2013 Emmanuel ......... C12N 15/8255
536/23.6

FOREIGN PATENT DOCUMENTS

WO  2017167228  10/2017
WO  2018001302  1/2018

OTHER PUBLICATIONS

Ptitsyn, Andrey A., and Jeffrey M. Gimble. "True or false: All genes are rhythmic." Annals of medicine 43.1 (2011): 1-12. (Year: 2011).*
Guo, Haiwei H., Juno Choe, and Lawrence A. Loeb. "Protein tolerance to random amino acid change." Proceedings of the National Academy of Sciences 101.25 (2004): 9205-9210. (Year: 2004).*
Ng, Pauline C., and Steven Henikoff. "Predicting deleterious amino acid substitutions." Genome research 11.5 (2001): 863-874. (Year: 2001).*
Genbank. "uncharacterized protein LLOC4331381 [Oryza sativa Japonica Group]" NCBI Reference Sequence: XP_015629335.1, Aug. 7, 2018.
Genbank. "AAA-ATPase At2g46620 [Oryza sativa Japonica Group]" NCBI Reference Sequence: XP_015628405.1, Aug. 7, 2018.
Genbank. "mavicyanin [Oryza sativa Japonica Group]" NCBI Reference Sequence: XP_015631850.1, Aug. 7, 2018.
Zhang, W. "The research on the function of rice gene OsAAA1 and screening of its interaction proteins" Chinese Master's Theses Full-text Database Agriculture Science and Technology, No. 05, May 15, 2019.
International Search Report and Written Opinion for PCT/CN2019/087910, mailed Feb. 24, 2020.

* cited by examiner

*Primary Examiner* — Charles Logsdon
*Assistant Examiner* — Kelsey L McWilliams

(57) ABSTRACT

Provided are suppression DNA constructs and CRISPR/Cas9 DNA constructs that are useful for conferring improved drought tolerance, yield, and/or nitrogen stress tolerance in a plant. Also provided are genome edited plants, or plants expressing a suppression DNA construct, having improved drought tolerance, yield and/nitrogen stress tolerance. Further provided are methods for improving drought tolerance, yield, and/or nitrogen stress tolerance by introducing a genome edit in a plant or expressing a suppression DNA construct in a plant.

14 Claims, 5 Drawing Sheets

Specification includes a Sequence Listing.

ABIOTIC STRESS TOLERANT PLANTS AND METHODS

FIELD

The field of the disclosure relates to plant breeding and genetics and, particularly, relates to improving tolerance to abiotic stress in plants.

REFERENCE TO SEQUENCE LISTING SUBMITTED ELECTRONICALLY

The official copy of the sequence listing is submitted electronically via EFS-Web as an ASCII formatted sequence listing with a file named RTS22593N-US-PCT_SequenceListing_ST25.txt created on Oct. 21, 2021 and having a size of 234 kilobytes and is filed concurrently with the specification. The sequence listing comprised in this ASCII formatted document is part of the specification and is herein incorporated by reference in its entirety.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249).

Accordingly, there is a need to develop compositions and methods that increase tolerance to abiotic stress in plants. This invention provides such compositions and methods.

SUMMARY

The following embodiments are among those encompassed by the disclosure:

In one embodiment, the present disclosure provides a suppression DNA construct comprising at least one heterologous regulatory element operably linked to suppression elements, wherein the suppression elements decrease the expression of an endogenous target polynucleotide encoding a polypeptide comprising an amino acid sequence of at least 90% sequence identity to SEQ ID NO: 3, 6, 9, 12, 15, 18 or 21. In certain embodiments, the suppression elements comprise at least 100 contiguous base pairs of a polynucleotide encoding a polypeptide comprising an amino acid sequence of at least 90% sequence identity to SEQ ID NO: 3, 6, 9, 12, 15, 18 or 21. In certain embodiments, the suppression elements comprise the polynucleotide of SEQ ID NO: 51.

The present disclosure also provides a CRISPR/Cas construct comprising at least one heterologous regulatory sequence operably linked to gRNA, wherein the gRNA is targeted to a genomic region containing an endogenous BCS1-2, DnaJ7, LNTP10, GH17.2, DUF6, ATAP1 or PCL1 gene and/or its regulatory elements to reduce the expression or activity of an endogenous BCS1-2, DnaJ7, LNTP10, GH17.2, DUF6, ATAP1 or PCL1 polypeptide. In certain embodiments, the endogenous gene encodes a polypeptide with amino acid sequence of at least 90% identity to SEQ ID NO: 3, 6, 9, 12, 15, 18 or 21. In certain embodiments, the BCS1-2, DnaJ7, LNTP10, GH17.2, DUF6, ATAP1 or PCL1 gene comprises a polynucleotide with nucleotide sequence of SEQ ID NO: 1, 2, 4, 5, 7, 8, 10, 11, 13, 14, 16, 17, 19, or 20 or an allelic variant thereof comprising 1 to about 10 nucleotide changes. In certain embodiments, the endogenous regulatory elements comprise a polynucleotide with nucleotide sequence of SEQ ID NO: 74 or 75.

The present disclosure further provides a modified plant or seed having decreased expression or activity of an endogenous BCS1-2, DnaJ7, LNTP10, GH17.2, DUF6, ATAP1 or PCL1 polypeptide. In certain embodiments, the modified plant or seed comprises a suppression DNA construct comprising at least one heterologous regulatory element operably linked to suppression elements, wherein the suppression elements decrease the expression of the endogenous BCS1-2, DnaJ7, LNTP10, GH17.2, DUF6, ATAP1 or PCL1 polypeptide. In certain embodiments, the polypeptide comprises an amino acid sequence of at least 90% sequence identity to SEQ ID NO: 3, 6, 9, 12, 15, 18 or 21. In certain embodiments, the suppression elements comprise at least 100 contiguous base pairs of a polynucleotide encoding an amino acid sequence of at least 90% sequence identity to SEQ ID NO: 3, 6, 9, 12, 15, 18 or 21. In certain embodiments, the suppression elements comprise the polynucleotide of SEQ ID NO: 51.

In certain embodiments, the modified plant or seed comprises a targeted genetic modification at a genomic locus comprising a polynucleotide encoding a BCS1-2, DnaJ7, LNTP10, GH17.2, DUF6, ATAP1 or PCL1 polypeptide, wherein the genetic modification decreases the expression and/or activity of the polypeptide. In certain embodiments, the polynucleotide encodes a polypeptide comprising an amino acid sequence of at least 90% sequence identity to SEQ ID NO: 3, 6, 9, 12, 15, 18 or 21.

In certain embodiments, the modified plant or seed exhibits at least one phenotype selected from the group consisting of: increased drought tolerance, increased grain yield, increased abiotic stress tolerance, improved nitrogen stress tolerance, or improved nitrogen use efficiency (NUE). In certain embodiments, the modified plant or seed having decreased expression and/or activity of a BCS1-2, DnaJ7, LNTP10, GH17.2, DUF6, ATAP1 or PCL1 polypeptide has increased drought tolerance, increased grain yield, and/or increased abiotic stress tolerance. In certain embodiments, the modified plant or seed having decreased expression and/or activity of a LNTP10, DUF6, or ATAP1 polypeptide has improved nitrogen stress tolerance, or improved nitrogen use efficiency (NUE) and/or increased grain yield when grown under low nitrogen conditions compared to a control plant.

In certain embodiments, the plant of the compositions and methods described herein is selected from the group consisting of rice, maize, soybean, sunflower, sorghum, canola, wheat, alfalfa, cotton, barley, millet, sugar cane and switchgrass.

Also provided are methods for increasing drought tolerance in a plant, the method comprising decreasing the expression and/or activity of at least one polynucleotide encoding a BCS1-2, DnaJ7, LNTP10, GH17.2, DUF6, ATAP1 or PCL1 polypeptide in the plant. In certain embodiments, the polypeptide comprises an amino acid sequence of at least 80% sequence identity to SEQ ID NO: 3, 6, 9, 12, 15, 18 or 21.

In certain embodiments, the method for increasing drought tolerance comprises: (a) introducing into a regenerable plant cell a suppression DNA construct, wherein the suppression DNA construct comprises at least one heterologous regulatory element operably linked to suppression elements; (b) regenerating a modified plant from the regenerable plant cell, wherein the plant comprises the suppression DNA construct. In certain embodiments, the suppression elements decrease the expression of an endogenous target polynucleotide with amino acid sequence of at least 90% sequence identity to SEQ ID NO: 3, 6, 9, 12, 15, 18 or 21. In certain embodiments, the suppression elements comprise at least 100 contiguous base pairs of a polynucleotide with amino acid sequence of at least 90% sequence identity to SEQ ID NO: 3, 6, 9, 12, 15, 18 or 21. In certain embodiments, the suppression elements comprise the polynucleotide of SEQ ID NO: 51.

In certain embodiments, the method for increasing drought tolerance comprises: (a) introducing into a regenerable plant cell a targeted genetic modification at a genomic locus comprising a polynucleotide encoding a BCS1-2, DnaJ7, LNTP10, GH17.2, DUF6, ATAP1 or PCL1 polypeptide; and (b) generating the plant, wherein the plant comprises in its genome the introduced genetic modification and has decreased expression and/or activity of the polypeptide. In certain embodiments, the polypeptide comprises an amino acid sequence of at least 80% sequence identity, when compared to SEQ ID NO: 3, 6, 9, 12, 15, 18 or 21. In certain embodiments, the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at 80% sequence identity, when compared to SEQ ID NO: 3, 6, 9, 12, 15, 18 or 21.

In certain embodiments, the targeted genetic modification is introduced by a CRISPR/Cas construct comprising at least one heterologous regulatory sequence operably linked to gRNA, wherein the gRNA is targeted to the endogenous BCS1-2, DnaJ7, LNTP10, GH17.2, DUF6, ATAP1 or PCL1 gene and/or its regulatory elements.

Also provided are methods for increasing nitrogen stress tolerance, NUE, and/or grain yield in a plant, the method comprising decreasing the expression and/or activity of at least one polynucleotide encoding a LNTP10, DUF6, or ATAP1 polypeptide in the plant. In certain embodiments, the polypeptide comprises an amino acid sequence of at least 80% sequence identity to SEQ ID NO: 9, 15, or 18.

In certain embodiments, the method for increasing nitrogen stress tolerance, NUE, and/or grain yield comprises: (a) introducing into a regenerable plant cell a suppression DNA construct, wherein the suppression DNA construct comprises at least one heterologous regulatory element operably linked to suppression elements; (b) regenerating a modified plant from the regenerable plant cell wherein the plant comprises the suppression DNA construct. In certain embodiments, the suppression elements suppress the expression of an endogenous target polynucleotide with amino acid sequence of at least 90% sequence identity to SEQ ID NO: 9, 15, or 18. In certain embodiments, the suppression elements comprise at least 100 contiguous base pairs of a polynucleotide with amino acid sequence of at least 90% sequence identity to SEQ ID NO: 9, 15, or 18.

In certain embodiments, the method for increasing nitrogen stress tolerance, NUE, and/or grain yield comprises: (a) introducing into a regenerable plant cell a targeted genetic modification at a genomic locus comprising a polynucleotide encoding a LNTP10, DUF6, or ATAP1 polypeptide; and (b) generating the plant, wherein the plant comprises in its genome the introduced genetic modification and has decreased expression and/or activity of the polypeptide. In certain embodiments, the polypeptide comprises an amino acid sequence of at least 80% sequence identity, when compared to SEQ ID NO: 9, 15, or 18. In certain embodiments, the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at 80% sequence identity, when compared to SEQ ID NO: 9, 15, or 18.

BRIEF DESCRIPTION OF THE DRAWINGS AND SEQUENCE LISTING

The disclosure can be more fully understood from the following detailed description and the accompanying drawings and Sequence Listing which form a part of this application. The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

Sequence Listing Description

Figure 1:
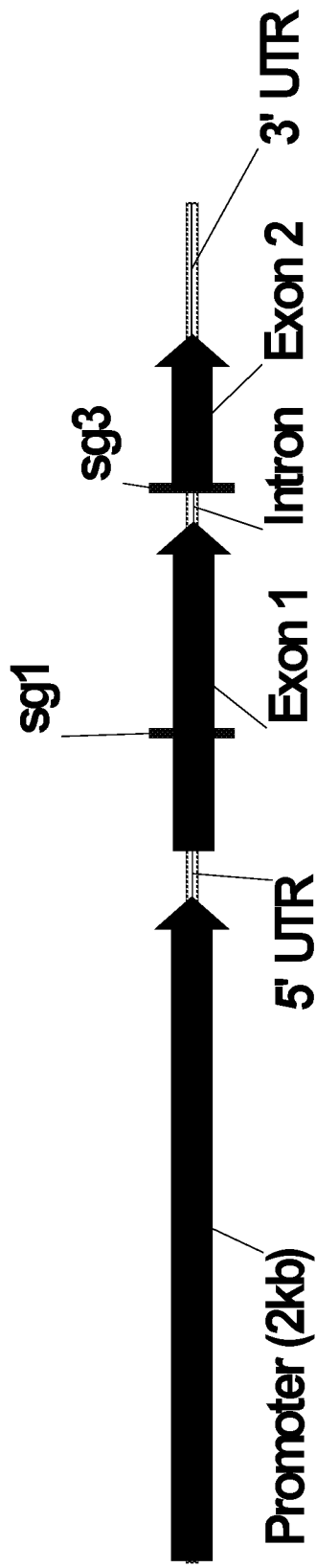
FIG. 1 shows the schematic of sgRNA distribution in the genome of OsBCS1-2 gene.
Figure 2:
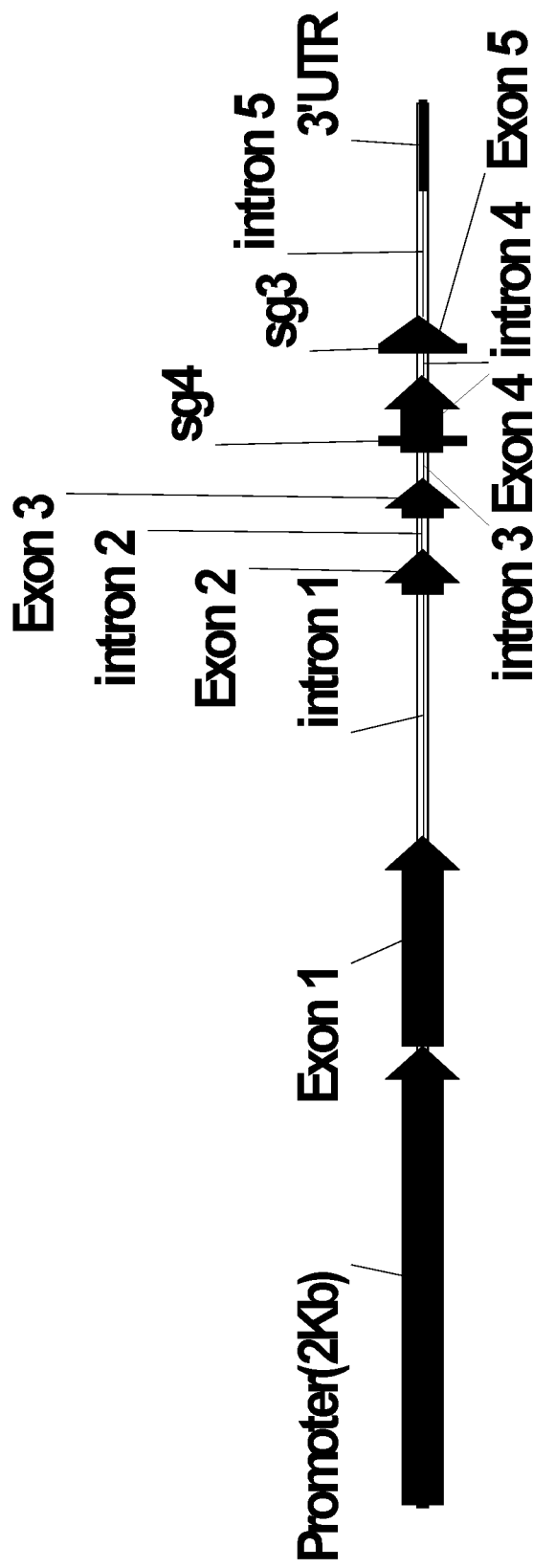
FIG. 2 shows the schematic of sgRNA distribution in the genome of OsDnaJ7 gene.
Figure 3:
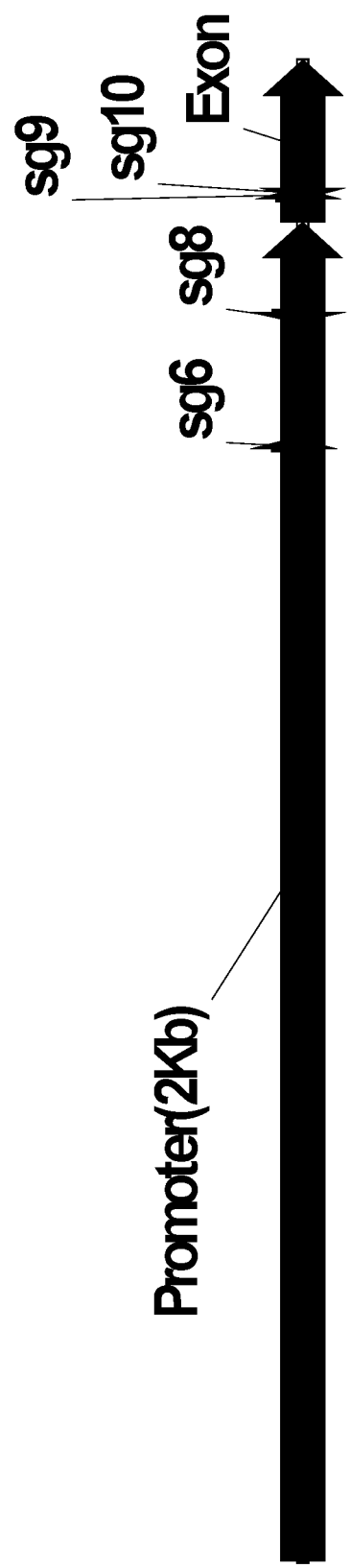
FIG. 3 shows the schematic of sgRNA distribution in the genome of OsLNTP10 gene and its regulatory element.
Figure 4:
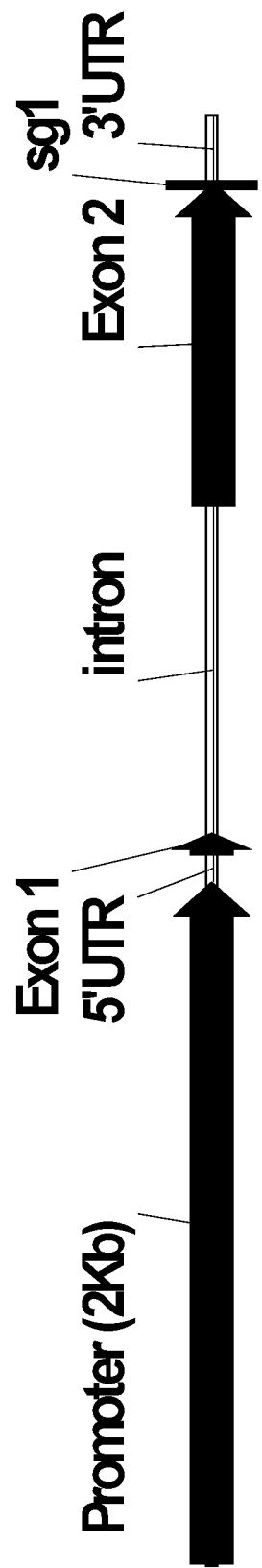
FIG. 4 shows the schematic of sgRNA distribution in the genome of OsGH17.2 gene and its regulatory element.
Figure 5:
FIG. 5 shows the schematic of sgRNA distribution in the genome of OsDUF6 gene.

| Source species | Clone Designation | SEQ ID NO: (Nucleotide) | SEQ ID NO: (Amino Acid) |
|---|---|---|---|
| Oryza sativa | OsBCS1-2 | 1, 2 | 3 |
| Oryza sativa | OsDnaJ7 | 4, 5 | 6 |
| Oryza sativa | OsLNTP10 | 7, 8 | 9 |
| Oryza sativa | OsGH17.2 | 10, 11 | 12 |
| Oryza sativa | OsDUF6 | 13, 14 | 15 |
| Oryza sativa | OsATAP1 | 16, 17 | 18 |
| Oryza sativa | OsPCL1 | 19, 20 | 21 |
| Artificial | Primers | 22-49, 52-55 | n/a |
| Lycopersicon esculintum | Intron | 50 | n/a |
| Oryza sativa | Sense strand cDNA fragment of OsPCL1 used for constructing RNAi vector | 51 | n/a |

TABLE 1-continued

Sequence Listing Description

| Source species | Clone Designation | SEQ ID NO: (Nucleotide) | SEQ ID NO: (Amino Acid) |
|---|---|---|---|
| Artificial | gRNA | 56-66 | n/a |
| Zea mays | Ubiquitin Promoter | 67 | n/a |
| Artificial | Nucleus localization sequence | 68 | n/a |
| Cauliflower mosaic virus | CaMV 3'UTR | 69 | n/a |
| Oryza sativa | rU6-Promoter | 70 | n/a |
| Artificial | gRNA scaffold | 71 | n/a |
| Artificial | pMD19GW | 72 | n/a |
| Artificial | pCAMBIA 1300DsRed-35S-GW | 73 | n/a |
| Oryza sativa | OsLNTP10 promoter | 74 | n/a |
| Oryza sativa | 3'UTR of OsGH17.2 | 75 | n/a |
| Oryza sativa | BCS1-2 paralog | 76 | 77 |
| Zea mays | BCS1-2 homolog | 78 | 79 |
| Sorghum bicolor | BCS1-2 homolog | 80 | 81 |
| Arabidopsis | BCS1-2 homolog | 82 | 83 |
| Glycine max | BCS1-2 homolog | 84 | 85 |
| Oryza sativa | DnaJ7 paralog | 86 | 87 |
| Zea mays | DnaJ7 homolog | 88 | 89 |
| Sorghum bicolor | DnaJ7 homolog | 90 | 91 |
| Arabidopsis | DnaJ7 homolog | 92 | 93 |
| Glycine max | DnaJ7 homolog | 94 | 95 |
| Oryza sativa | LNTP10 paralog | 96 | 97 |
| Sorghum bicolor | LNTP10 homolog | 98 | 99 |
| Oryza sativa | GH17.2 paralog | 100 | 101 |
| Zea mays | GH17.2 homolog | 102 | 103 |
| Sorghum bicolor | GH17.2 homolog | 104 | 105 |
| Arabidopsis | GH17.2 homolog | 106 | 107 |
| Glycine max | GH17.2 homolog | 108 | 109 |
| Oryza sativa | DUF6 paralog | 110 | 111 |
| Zea mays | DUF6 homolog | 112 | 113 |
| Sorghum bicolor | DUF6 homolog | 114 | 115 |
| Arabidopsis | DUF6 homolog | 116 | 117 |
| Glycine max | DUF6 homolog | 118 | 119 |
| Oryza sativa | ATAP1 paralog | 120 | 121 |
| Zea mays | ATAP1 homolog | 122 | 123 |
| Sorghum bicolor | ATAP1 homolog | 124 | 125 |
| Arabidopsis | ATAP1 homolog | 126 | 127 |
| Glycine max | ATAP1 homolog | 128 | 129 |
| Oryza sativa | PCL1 paralog | 130 | 131 |
| Zea mays | PCL1 homolog | 132 | 133 |
| Sorghum bicolor | PCL1 homolog | 134 | 135 |
| Arabidopsis | PCL1 homolog | 136 | 137 |
| Glycine max | PCL1 homolog | 138 | 139 |

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

Definitions

As used herein, "increased drought tolerance" of a plant refers to any measurable improvement in a physiological or physical characteristic, such as yield, as measured relative to a reference or control plant when grown under drought conditions. Typically, when a plant comprising a recombinant DNA construct or DNA modification in its genome exhibits increased drought tolerance relative to a reference or control plant, the reference or control plant does not comprise in its genome the recombinant DNA construct or DNA modification.

As used herein, "increased nitrogen stress tolerance" of a plant refers to any measurable improvement in a physiological or physical characteristic, such as yield, as measured relative to a reference or control plant, when grown under low nitrogen and/or nitrogen limiting conditions. Typically, when a plant comprising a recombinant DNA construct or DNA modification in its genome exhibits increased nitrogen stress tolerance relative to a reference or control plant, the reference or control plant does not comprise in its genome the recombinant DNA construct or DNA modification.

As used herein "nitrogen use efficiency (NUE)" refers to the ratio between the amount of fertilizer N removed by a plant and the amount of fertilizer N applied. Accordingly, in certain embodiments an increase in N use efficiency refers to any detectable increase in the amount of fertilizer N removed by a plant and the amount of fertilizer N applied. A person of ordinary skill in the art can calculate N use efficiency using routine methods in the art.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control," "control plant," or "control plant cell" or the like provides a reference point for measuring changes in phenotype of a subject plant or plant cell in which genetic alteration, such as transformation, has been affected as to a gene of interest. For example, a control plant may be a plant having the same genetic background as the subject plant except for the genetic alteration that resulted in the subject plant or cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment. "Promoter functional in a plant" is a promoter capable of controlling transcription of genes in plant cells whether or not its origin is from a plant cell. "Tissue-specific promoter" and "tissue-preferred promoter" refers to a promoter that is expressed predominantly but not necessarily exclusively in one tissue or organ, but that may also be expressed in one specific cell or cell type. "Developmentally regulated promoter" is a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

As used herein "increased", "increase", or the like refers to any detectable increase in an experimental group (e.g., plant with a DNA modification described herein) as compared to a control group (e.g., wild-type plant that does not comprise the DNA modification). Accordingly, increased expression of a protein comprises any detectable increase in the total level of the protein in a sample and can be determined using routine methods in the art such as, for example, Western blotting and ELISA.

As used herein, "yield" refers to the amount of agricultural production harvested per unit of land, and may include reference to bushels per acre or kilograms per mu of a crop at harvest, as adjusted for grain moisture (e.g., typically 15% for maize, 13.5% for rice). Grain moisture is measured in the grain at harvest. The adjusted test weight of grain is determined to be the weight in pounds per bushel or grams per plant, adjusted for grain moisture level at harvest.

A "suppression DNA construct" is a recombinant DNA construct which when transformed or stably integrated into the genome of the plant, results in "silencing" of a target gene in the plant. The target gene may be endogenous or transgenic to the plant.

"Silencing", as used herein with respect to the target gene, refers generally to the suppression of levels of mRNA or protein/enzyme expressed by the target gene, and/or the level of the enzyme activity or protein functionality. The terms "suppression", "suppressing" and "silencing", used interchangeably herein, includes lowering, reducing, declining, decreasing, inhibiting, eliminating or preventing.

Suppression DNA constructs are well-known in the art, and may be readily constructed once the target gene of interest is selected, and include, without limitation, co-suppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target gene or gene product. "Co-suppression" refers to the production of sense RNA transcripts capable of suppressing the expression of the target gene or gene product. "Sense" RNA refers to RNA transcript that includes the mRNA and can be translated into protein within a cell or in vitro. Another variation describes the use of plant viral sequences to direct the suppression of proximal mRNA encoding sequences (PCT Publication No. WO 98/36083 published on Aug. 20, 1998).

RNA interference (RNAi) refers to the process of sequence-specific post-transcriptional gene silencing in animals mediated by short interfering RNAs (siRNAs) (Fire et al., Nature 391:806 (1998)). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., *Trends Genet.* 15:358 (1999)).

As used herein, "sequence identity" or "identity" in the context of two polynucleotides or polypeptide sequences make reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Unless stated otherwise, multiple alignments of the sequences provided herein are performed using the Clustal V method of alignment (Higgins and Sharp. (1989) CABIOS. 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Compositions:

The present disclosure provides constructs to decrease the expression and/or activity of a BCS1-2, DnaJ7, LNTP10, GH17.2, DUF6, ATAP1, or PCL1 polypeptide.

In one aspect of the disclosure, the polypeptide comprises an amino acid sequence that is at least 80% identical (e.g. 81%, 82%, 83%, 84%, 85%, 86%, 87%, 88%, 89%, 90%, 91%, 92%, 93%, 94%, 95%, 96%, 97%, 98%, 99%, or 100%) to the amino acid sequence of any one of SEQ ID NO: 3 (OsBCS1-2), SEQ ID NO: 6 (OsDnaJ7), SEQ ID NO: 9 (OsLNTP10), SEQ ID NO: 12 (OsGH17.2), SEQ ID NO: 15 (OsDUF6), SEQ ID NO: 18 (OsATAP1), and SEQ ID NO: 21 (OsPCL1).

"OsBCS1-2" refers to a rice polypeptide that confers drought sensitive phenotype when overexpressed. The OsBCS1-2 polypeptide (SEQ ID NO: 3) is encoded by the coding sequence (CDS) (SEQ ID NO: 2) or nucleotide sequence (SEQ ID NO: 1) at rice gene locus LOC_Os01g42030.1, which is annotated as "mitochondrial chaperone BCS1, putative, expressed" in TIGR. "BCS1-2 polypeptide" refers herein to the OsBCS1-2 polypeptide and its paralogs (e.g., SEQ ID NO: 77 encoded by SEQ ID NO: 76) or homologs from other organisms, such as maize (SEQ ID NO: 79 encoded by SEQ ID NO: 78), sorghum (SEQ ID NO: 81 encoded by SEQ ID NO: 80), *Arabidopsis* (SEQ ID NO: 83 encoded by SEQ ID NO: 82), or soybean (SEQ ID NO: 85 encoded by SEQ ID NO: 84).

"OsDnaJ7" refers to a rice polypeptide that confers drought sensitive phenotype when overexpressed. The OsDnaJ7 polypeptide (SEQ ID NO: 6) is encoded by the coding sequence (CDS) (SEQ ID NO: 5) or nucleotide sequence (SEQ ID NO: 4) at rice gene locus LOC_Os02g51730.1, which is annotated as "DnaJ homolog subfamily C member 7" in TIGR and "universal stress protein domain containing protein, putative" in NCBI. "DnaJ7 polypeptide" refers herein to the OsDnaJ7 polypeptide and its paralogs (e.g., SEQ ID NO: 87 encoded by SEQ ID NO: 86) or homologs from other organisms, such as maize (SEQ ID NO: 89 encoded by SEQ ID NO: 88), sorghum (SEQ ID NO: 91 encoded by SEQ ID NO: 90), *Arabidopsis* (SEQ ID NO: 93 encoded by SEQ ID NO: 92), or soybean (SEQ ID NO: 95 encoded by SEQ ID NO: 94).

"OsLNTP10" refers to a rice polypeptide that confers drought sensitive phenotype when overexpressed. The OsLNTP10 polypeptide (SEQ ID NO: 9) is encoded by the coding sequence (CDS) (SEQ ID NO: 8) or nucleotide sequence (SEQ ID NO: 7) at rice gene locus LOC_Os05g38940.1, which is annotated as "expressed protein" in TIGR. "LNTP10 polypeptide" refers herein to the OsLNTP10 polypeptide and its paralogs (e.g., SEQ ID NO: 97 encoded by SEQ ID NO: 96) or homologs from other organisms, such as sorghum (SEQ ID NO: 99 encoded by SEQ ID NO: 98).

"OsGH17.2" refers to a rice polypeptide that confers drought sensitive phenotype when overexpressed. The OsGH17.2 polypeptide (SEQ ID NO: 12) is encoded by the coding sequence (CDS) (SEQ ID NO: 11) or nucleotide sequence (SEQ ID NO: 10) at rice gene locus LOC_Os01g58730.1, which is annotated as "Glycosyl hydrolases family 17, putative, expressed" in TIGR. "GH17.2 polypeptide" refers herein to the OsGH17.2 polypeptide and its paralogs (e.g., SEQ ID NO: 101 encoded by SEQ ID NO: 100) or homologs from other organisms, such as maize (SEQ ID NO: 103 encoded by SEQ ID NO: 102), sorghum (SEQ ID NO: 105 encoded by SEQ ID NO: 104), *Arabidopsis* (SEQ ID NO: 107 encoded by SEQ ID NO: 106), or soybean (SEQ ID NO: 109 encoded by SEQ ID NO: 108).

"OsDUF6" refers to a rice polypeptide that confers drought sensitive phenotype when overexpressed. The OsDUF6 polypeptide (SEQ ID NO: 15) is encoded by the coding sequence (CDS) (SEQ ID NO: 14) or nucleotide sequence (SEQ ID NO: 13) at rice gene locus LOC_Os03g02280.1, which is annotated as "DUF584 domain containing protein, putative, expressed" in TIGR. "DUF6 polypeptide" refers herein to the OsDUF6 polypeptide and its paralogs (e.g., SEQ ID NO: 111 encoded by SEQ ID NO: 110) or homologs from other organisms, such as maize (SEQ ID NO: 113 encoded by SEQ ID NO: 112), sorghum (SEQ ID NO: 115 encoded by SEQ ID NO: 114), Arabidopsis (SEQ ID NO: 117 encoded by SEQ ID NO: 116), or soybean (SEQ ID NO: 119 encoded by SEQ ID NO: 118).

"OsATAP1" refers to a rice polypeptide that confers drought sensitive phenotype when overexpressed. The OsATAP1 polypeptide (SEQ ID NO: 18) is encoded by the coding sequence (CDS) (SEQ ID NO: 17) or nucleotide sequence (SEQ ID NO: 16) at rice gene locus LOC_Os03g02330.1, which is annotated as "AAA-type ATPase family protein, putative, expressed" in TIGR. "ATAP1 polypeptide" refers herein to the OsATAP1 polypeptide and its paralogs (e.g., SEQ ID NO: 121 encoded by SEQ ID NO: 120) or homologs from other organisms, such as maize (SEQ ID NO: 123 encoded by SEQ ID NO: 122), sorghum (SEQ ID NO: 125 encoded by SEQ ID NO: 124), Arabidopsis (SEQ ID NO: 127 encoded by SEQ ID NO: 126), or soybean (SEQ ID NO: 129 encoded by SEQ ID NO: 128).

"OsPCL1" refers to a rice polypeptide that confers drought sensitive phenotype when overexpressed. The OsPCL1 polypeptide (SEQ ID NO: 21) is encoded by the coding sequence (CDS) (SEQ ID NO: 20) or nucleotide sequence (SEQ ID NO: 19) at rice gene locus LOC_Os03g02400.1, which is annotated as "Plastocyanin-like domain containing protein, putative, expressed" in TIGR. "PCL1 polypeptide" refers herein to the OsPCL1 polypeptide and its paralogs (e.g., SEQ ID NO: 131 encoded by SEQ ID NO: 130) or homologs from other organisms, such as maize (SEQ ID NO: 133 encoded by SEQ ID NO: 132), sorghum (SEQ ID NO: 135 encoded by SEQ ID NO: 134), Arabidopsis (SEQ ID NO: 137 encoded by SEQ ID NO: 136), or soybean (SEQ ID NO: 139 encoded by SEQ ID NO: 138).

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

A. Suppression DNA Constructs and CRISPR/Cas Constructs

Provided are suppression DNA constructs that decrease the expression and/or activity of a BCS1-2, DnaJ7, LNTP10, GH17.2, DUF6, ATAP1, or PCL1 polypeptide. In certain embodiments, the suppression DNA construct is a co-suppression construct, antisense construct, viral-suppression construct, hairpin suppression construct, stem-loop suppression construct, double-stranded RNA-producing construct, and more generally, RNAi (RNA interference) construct and small RNA constructs such as siRNA (short interfering RNA) constructs and miRNA (microRNA) constructs.

In certain embodiments, the suppression DNA construct comprises at least one heterologous regulatory element operably linked to suppression elements, wherein the suppression elements suppress the expression of an endogenous target polynucleotide with amino acid sequence of at least 90% sequence identity to SEQ ID NO: 3, 6, 9, 12, 15, 18 or 21. In certain embodiments, the suppression elements comprise at least 100 contiguous base pairs of a polynucleotide with amino acid sequence of at least 90% sequence identity to SEQ ID NO: 3, 6, 9, 12, 15, 18 or 21. In certain embodiments, the suppression elements comprise the polynucleotide of SEQ ID NO: 51.

The present disclosure also provides a CRISPR/Cas construct comprising at least one heterologous regulatory sequence operably linked to gRNA, wherein the gRNA is targeted to a genomic region containing an endogenous BCS1-2, DnaJ7, LNTP10, GH17.2, DUF6, ATAP1 or PCL1 gene and/or its regulatory elements to reduce the expression or activity of an endogenous BCS1-2, DnaJ7, LNTP10, GH17.2, DUF6, ATAP1 or PCL1 polypeptide. In certain embodiments, the endogenous gene encodes a polypeptide with amino acid sequence of at least 90% identity to SEQ ID NO: 3, 6, 9, 12, 15, 18 or 21. Further, the BCS1-2, DnaJ7, LNTP10, GH17.2, DUF6, ATAP1 or PCL1 gene comprises a polynucleotide with nucleotide sequence of SEQ ID NO: 1, 2, 4, 5, 7, 8, 10, 11, 13, 14, 16, 17, 19, or 20 or an allelic variant thereof comprising 1 to about 10 nucleotide changes. In certain embodiments, the endogenous regulatory elements comprise a polynucleotide with nucleotide sequence of SEQ ID NO: 74 or 75. In certain embodiments, the gRNA comprises a sequence comprising one or more of SEQ ID NOs: 56-66.

In certain embodiments the at least one regulatory element is a heterologous regulatory element. In certain embodiments, the at least one regulatory element of the recombinant DNA construct comprises a promoter. In certain embodiments, the promoter is a heterologous promoter.

A number of promoters can be used in recombinant DNA constructs of the present disclosure. The promoters can be selected based on the desired outcome, and may include constitutive, tissue-specific, inducible, or other promoters for expression in the host organism.

A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) *Plant J.* 12(2):255-265; Kwon et al. (1994) *Plant Physiol.* 105:357-367; Yamamoto et al. (1994) *Plant Cell Physiol.* 35(5):773-778; Gotor et al. (1993) *Plant J.* 3:509-518; Orozco et al. (1993) *Plant Mol. Biol.* 23(6): 1129-1138; and Matsuoka et al. (1993) *Proc. Natl. Acad. Sci. USA* 90(20):9586-9590).

Promoters which are seed or embryo-specific and may be useful in the disclosure include soybean Kunitz trypsin inhibitor (Kti3, Jofuku and Goldberg. (1989) *Plant Cell* 1:1079-1093), convicilin, vicilin, and legumin (pea cotyledons) (Rerie, W. G., et al. (1991) *Mol. Gen. Genet.* 259: 149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7: L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Also contemplated are synthetic promoters which include a combination of one or more heterologous regulatory elements.

The promoter of the suppression DNA constructs of the invention can be any type or class of promoter known in the art, such that any one of a number of promoters can be used to express the various polynucleotide sequences disclosed herein, including the native promoter of the polynucleotide sequence of interest. The promoters for use in the suppression DNA constructs of the invention can be selected based on the desired outcome.

The suppression DNA constructs of the present disclosure may also include other regulatory elements, including but not limited to, translation leader sequences, introns, and polyadenylation recognition sequences. In certain embodiments, a suppression DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol Cell Biol.* 8:4395-4405; Callis et al. (1987) *Genes Dev.* 1:1183-1200).

B. Plants and Plant Cells

Provided are plants, plant cells, plant parts, seed and grain comprising in its genome any of the suppression DNA constructs described herein, so that the plants, plant cells, plant parts, seed, and/or grain have decreased expression of the encoded polypeptide.

Also provided are plants, plant cells, plant parts, seeds, and grain comprising an introduced genetic modification at a genomic locus that encodes a polypeptide described herein. In certain embodiments, the polypeptide comprises an amino acid sequence that is at least 80% identical to an amino acid sequence selected from the group consisting of SEQ ID NOs: 3, 6, 9, 12, 15, 18 or 21. In certain embodiments, the genetic modification decreases the activity of the encoded polypeptide. In certain embodiments, the genetic modification decreases the level of the encoded polypeptide. In certain embodiments, the genetic modification decreases both the level and activity of the encoded polypeptide.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

In certain embodiments the plant exhibits increased drought tolerance and/or nitrogen stress tolerance when compared to a control plant. In certain embodiments, the plant exhibits an alteration of at least one agronomic characteristic when compared to the control plant.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

C. Stacking with Other Traits of Interest

In some embodiments, the inventive polynucleotides disclosed herein are engineered into a molecular stack. Thus, the various host cells, plants, plant cells, plant parts, seeds, and/or grain disclosed herein can further comprise one or more traits of interest. In certain embodiments, the host cell, plant, plant part, plant cell, seed, and/or grain is stacked with any combination of polynucleotide sequences of interest in order to create plants with a desired combination of traits. As used herein, the term "stacked" refers to having multiple traits present in the same plant or organism of interest. For example, "stacked traits" may comprise a molecular stack where the sequences are physically adjacent to each other. A trait, as used herein, refers to the phenotype derived from a particular sequence or groups of sequences. In one embodiment, the molecular stack comprises at least one polynucleotide that confers tolerance to glyphosate. Polynucleotides that confer glyphosate tolerance are known in the art.

In certain embodiments, the molecular stack comprises at least one polynucleotide that confers tolerance to glyphosate and at least one additional polynucleotide that confers tolerance to a second herbicide.

In certain embodiments, the plant, plant cell, seed, and/or grain having an inventive polynucleotide sequence may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glufosinate herbicides; herbicides which target the protox enzyme (also referred to as "protox inhibitors").

The plant, plant cell, plant part, seed, and/or grain comprising decreased expression and/or activity of the polypeptides described herein can also be combined with at least one other trait to produce plants that further comprise a variety of desired trait combinations. For instance, the plant, plant cell, plant part, seed, and/or grain may be stacked with polynucleotides encoding polypeptides having pesticidal and/or insecticidal activity, or a plant, plant cell, plant part, seed, and/or grain having an inventive polynucleotide sequence may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods:

A. Method for Increasing Drought Tolerance, Increasing Grain Yield, and/or Increasing Nitrogen Use Efficiency in a Plant Provided is a method for increasing drought tolerance, increasing grain yield, and/or increasing nitrogen use efficiency in a plant, comprising decreasing the expression and/or activity of at least one polynucleotide encoding a BCS1-2, DnaJ7, LNTP10, GH17.2, DUF6, ATAP1 or PCL1 polypeptide. In certain embodiments, polynucleotide encodes a polypeptide comprising an amino acid sequence of at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12, 15, 18 or 21.

In certain embodiments, the method comprises: (a) expressing in a regenerable plant cell a suppression DNA construct, described herein; and (b) generating the plant, wherein the plant comprises in its genome the suppression DNA construct. In certain embodiments the regulatory element is a heterologous promoter.

In certain embodiments, the method comprises: (a) introducing in a regenerable plant cell a targeted genetic modification at a genomic locus that encodes the polypeptide; and (b) generating the plant, wherein the level and/or activity of the encoded polypeptide is decreased in the plant. In certain embodiments the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), engineered site-specific meganucleases, or Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at least 80% identical to an amino acid sequence selected from the group consisting of SEQ ID NOs: 3, 6, 9, 12, 15, 18 or 21.

The plant for use in the inventive methods can be any plant species described herein. In certain embodiments, the plant is maize, soybean, or rice.

Various methods can be used to introduce a sequence of interest into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-

1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed plant cells which are derived by plant transformation techniques, including those discussed above, can be cultured to regenerate a whole plant which possesses the transformed genotype (i.e., an inventive polynucleotide), and thus the desired phenotype, such as increased yield. For transformation and regeneration of maize see, Gordon-Kamm et al., *The Plant Cell*, 2:603-618 (1990).

Various methods can be used to introduce a genetic modification at a genomic locus that encodes a polypeptide disclosed herein into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533(7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C-G to T-A conversion and A-T to G-C conversion at one more location made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR-Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

EXAMPLES

The following are examples of specific embodiments of some aspects of the invention. The examples are offered for illustrative purposes only and are not intended to limit the scope of the invention in any way.

Example 1

Cloning and Vector Construction of Drought Sensitive Genes

A binary construct that contains four multimerized enhancers elements derived from the Cauliflower Mosaic Virus 35S (CaMV 35S) promoter was used, and the rice activation tagging population was developed from four *japonica* (*Oryza sativa* ssp. *Japonica*) varieties (Zhonghua 11, Chaoyou 1, Taizhong 65 and Nipponbare), which were transformed by Agrobacteria-mediated transformation method as described by Lin and Zhang ((2005) *Plant Cell Rep*. 23:540-547). The transgenic lines generated were developed and the transgenic seeds were harvested to form the rice activation tagging population.

Drought sensitive tagging lines (ATLs) were confirmed in repeated field experiments and their T-DNA insertion loci were determined by ligation mediated nested PCR (OsBCS1-2, OsLNTP10) or plasmid rescue method (OsGH17.2, OsATAP1, OsDnaJ7, OsDUF6) or inverse PCR method (OsPCL1). The genes near by the left border and right border of the T-DNA were cloned and the functional genes were recapitulated by field screens. Only the recapitulated functional genes are shown herein. And based on LOC IDs of the genes shown in Table 2, primers were designed for cloning the rice drought sensitive genes OsBCS1-2, OsDnaJ7, OsLNTP10, OsGH17.2, OsDUF6, OsATAP1, OsPCL1.

TABLE 2

Rice gene names, Gene IDs (from TIGR) and Construct IDs

| Gene name | LOC ID | Construct ID |
|---|---|---|
| OsBCS1-2 | LOC_Os01g42030.1 | DP0962 |
| OsDnaJ7 | LOC_Os02g51730.1 | DP0396 |
| OsLNTP10 | LOC_Os05g38940.1 | DP0866 |
| OsGH17.2 | LOC_Os01g58730.1 | DP0334 |
| OsDUF6 | LOC_Os03g02280.1 | DP0786 |
| OsATAP1 | LOC_Os03g02330.1 | DP0329 |
| OsPCL1 | LOC_Os03g02400.1 | DP0780 |

PCR amplified products were extracted after the agarose gel electrophoresis using a column kit and then ligated with TA cloning vectors. The sequences and orientation in these constructs were confirmed by sequencing. Each gene was cloned into a plant binary construct.

Example 2

Transformation and Gene Expression Analysis of Transgenic Rice Lines

Zhonghua 11 (*Oryza sativa* L.) were transformed with either a vector prepared in Example 1 or an empty vector (DP0158) by Agrobacteria-mediated transformation as described by Lin and Zhang ((2005) *Plant Cell Rep.* 23:540-547). Transgenic seedlings (To) generated in the transformation laboratory were transplanted in field to get $T_1$ seeds. The $T_1$ and subsequent $T_2$ seeds were screened to confirm transformation and positively identified transgenic seeds were used in the following trait screens.

The gene expression levels in the leaves of the transgenic rice plants were determined by RT-PCR. Primers were designed for RT-PCR for OsBCS1-2, OsDnaJ7, OsLNTP10, OsGH17.2, OsDUF6, OsATAP1 and OsPCL1 genes in the over-expression transgenic rice. The level of expression in ZH11-TC (tissue cultured ZH11 rice) was set at 1.00, and the expression levels in the transgenic plants were compared to ZH11-TC. Gene expression was normalized based on the EF-1α mRNA levels, and the results from the gene expression analysis are provided in Table 3 below.

TABLE 3

Relative Expression Level Fold Increase in Transgenic Rice Plants

| Gene name | Construct ID | Relative Expression Level Fold Increase |
|---|---|---|
| OsBCS1-2 | DP0962 | From 38.25 to 4456.27 |
| OsDnaJ7 | DP0396 | From 6.4 to 4052.74 |
| OsLNTP10 | DP0866 | From 0.43 to 237.78 |
| OsGH17.2 | DP0334 | From 37794.93 to 446767 |
| OsDUF6 | DP0786 | From 1.59 to 125.82 |
| OsATAP1 | DP0329 | From 2.01 to 17.67 |
| OsPCL1 | DP0780 | From 1.75 to 1994.24 |

Example 3

Characterization of the Transgenic Rice Plants

The transgenic rice plants from Example 2 and ZH11-TC and DP0158 rice plants were tested for: (a) drought tolerance, (b) grain yield under well-watered conditions, (c) low nitrogen tolerance/nitrogen use efficiency.

$T_2$ seeds from the plants of Example 2 were sterilized by 800 ppm carbendazol for 8 hours at 32° C. and washed 3-5 time, soaked in water for 16 hours at 32° C., and germinated for 18 hours at 35-37° C. in an incubator. Germinated seeds were used as follows for each test:

(a) drought tolerance—germinated seeds were planted in a seedbed field. At 3-leaf stage, the seedlings were transplanted into the testing field with 4 replicates and 10 plants per replicate for each transgenic line, and the 4 replicates were planted in the same block. ZH11-TC and DP0158 seedlings were nearby the transgenic lines in the same block, and were used as controls in the statistical analysis. The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.). Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain yield per plant was measured. The grain yield data were statistically analyzed using mixed linear model.

(b) grain yield under well-watered conditions—germinated seeds were planted in a seedbed field. At 3-leaf stage, the seedlings were transplanted into the testing field with 4 replicates and 40 plants per replicate for each transgenic line, and the 4 replicates were planted in the same block. ZH11-TC, DP0158 and negative seedlings were nearby the transgenic lines in the same block, and were used as controls in the statistical analysis. The rice plants were managed by normal practice using pesticides and fertilizers. At the end of the growing season, representative plants of each transgenic line were harvested from the middle of the row per line, and grain yield per plant was measured. The grain yield data were statistically analyzed using mixed linear model.

(c) low nitrogen tolerance/nitrogen use efficiency—One nitrogen level: N-0 (using fertilizer without nitrogen) was set in the experiment. Germinated seeds were planted in a seedbed field. At 3-leaf stage, the seedlings were transplanted into the testing field with 4 replicates and 10 plants per replicate for each transgenic line, and the 4 replicates were planted in the same block. The ZH11-TC, DP0158 and negative plants were planted nearby the transgenic lines in the same block, and were used as controls in the statistical analysis. The rice plants were managed by normal practice using pesticides, but applying phosphorous fertilizer and potassium fertilizer for N-0 treatment.

At the end of the season, six representative plants of each transgenic line were harvested from the middle of the row per line and grain yield per plant was measured. The grain yield per plant data were statistically analyzed using mixed linear model by ASRemI program. Positive transgenic lines are selected based on the analysis (P<0.1).

The results from these studies are provided in Table 4, which provides the combined data of the transgenic lines for each of the constructs.

TABLE 4

Agronomic Characteristics of the Transgenic Rice Plants

| No | Construct ID | Avg. yield per plant under field drought conditions (g/plant) | Avg. Yield per plant under field low nitrogen conditions (g/plant) |
|---|---|---|---|
| 1 | ZH11-TC | 12.36 ± 2.09 | |
|   | DP0158 | 8.26 ± 2.09 | |
|   | DP0962 | 4.96 ± 1.76 $^{a,\,b}$ | |
| 2 | ZH11-TC | 4.62 ± 0.51 | |
|   | DP0158 | 3.36 ± 0.51 | |
|   | DP0396 | 3.40 ± 0.76 | |
| 3 | ZH11-TC | 5.61 ± 1.67 | 47.43 ± 3.86 |
|   | DP0158 | 4.53 ± 1.66 | 39.15 ± 3.86 |
|   | DP0866 | 4.01 ± 1.67 | 30.11 ± 3.39 $^{a,\,b}$ |
| 4 | ZH11-TC | 5.48 ± 0.89 | |
|   | DP0158 | 3.60 ± 0.89 | |
|   | DP0334 | 1.24 ± 0.73 $^{a,\,b}$ | |
| 5 | ZH11-TC | 8.88 ± 2.27 | 30.41 ± 2.02 |
|   | DP0158 | 8.34 ± 2.10 | 32.24 ± 2.01 |
|   | DP0786 | 2.50 ± 2.33 $^{a,\,b}$ | 21.08 ± 1.33 $^{a,\,b}$ |
| 6 | ZH11-TC | 5.44 ± 0.89 | 34.75 ± 2.95 |
|   | DP0158 | 4.03 ± 0.89 | 31.5 ± 2.95 |
|   | DP0329 | 1.78 ± 0.81 $^{a,\,b}$ | 26.79 ± 1.85 $^{a}$ |
| 7 | ZH11-TC | 3.63 ± 1.24 | |
|   | DP0158 | 4.11 ± 1.12 | |
|   | DP0780 | 2.86 ± 0.96 | |

$^{a}$ P ≤ 0.1 compared to ZH11-TC control in field;
$^{b}$ P ≤ 0.1 compared to DP0158 control in field.

DP0962-transgenic rice plants were tested five times in Hainan and Ningxia field in two years, respectively. Four of them showed that the average yield per plant of DP0962-transgenic rice decreased under field drought conditions compared to the controls. And the leaf rolling phenotype was observed in OsBCS1-2 high-expressing lines, while the OsBCS1-2 low-expressing lines showed good seed setting rate without leaf rolling phenotype. These results demonstrated that the yield and drought sensitive phenotype of DP0962-transgenic plants are correlated to the OsBCS1-2 gene expression level. As shown in Table 4, in Ningxia field, 9 of 12 events showed the yield per plant significantly decrease (P<0.1) than that of controls. The average yield per plant of these 12 events is 60% and 40% lower than that of ZH11-TC and DP0158 controls, respectively. Both yield and phenotypical observations consistently showed that OsBCS1-2 is a rice drought sensitive gene.

DP0396-transgenic rice plants were tested four times in Hainan, Beijing and Ningxia in two years. All experiments consistently showed that the average yield per plant of DP0396-transgenic rice decreased, and the leaf rolling phenotype can also be observed in OsDnaJ7 high-expressing lines under field drought conditions. From the Hainan field, 3 of 6 OsDnaJ7 high-expressing lines showed significantly decreased yield per plant than that of ZH11-TC and DP0158 controls. The average yield per plant of these 3 events is 68% and 56% lower than that of ZH11-TC and DP0158 controls, respectively. But another three OsDnaJ7 low-expressing lines showed the yield per plant increased than that of DP0158 controls, and the average yield per plant of these 3 events is 15% and 58% higher than that of ZH11-TC and DP0158 controls, respectively (Table 4). Both yield and phenotypical observations consistently showed that OsDnaJ7 is a rice drought sensitive gene.

DP0866-transgenic rice plants were tested three times in Hainan and Ningxia in two years. All the experiments consistently showed that the average yield per plant of OsLNTP10 high-expressing lines decreased, while the average yield per plant of OsLNTP10 low-expressing lines increased under the field drought conditions. From the Hainan field, 5 of 9 low-expressing lines observed good seed setting rate, and showed significantly increased yield per plant than that of ZH11-TC and DP0158 controls. The average yield of these 5 low-expressing lines is 52% and 89% higher than that of ZH11-TC and DP0158 controls, respectively. Another 4 high-expressing lines showed decreased yield per plant than that of ZH11-TC and DP0158 controls. The average yield of these 4 high-expressing lines is 29% and 11% lower than that of ZH11-TC and DP0158 controls, respectively. The average yield per plant of these 4 low-expressing lines is showed in Table 4. Under the field low nitrogen conditions, DP0866-transgenic rice plants were tested three times in Beijing. All experiments obtained the consistently results. At one year in Beijing, 4 of 9 high-expressing lines showed decreased the yield per plant than that of ZH11-TC and DP0158 controls. The average yield of these 4 high-expressing events is 36% and 23% lower than that of ZH11-TC and DP0158 controls, respectively. Another 5 low-expressing lines showed increased yield per plant than that of the controls. The average yield per plant of these 5 low-expressing lines is 2% and 24% higher than that of ZH11-TC and DP0158 controls, respectively (Table 4). Both yield and phenotypical observations consistently showed that OsLNTP10 is a rice drought sensitive and low nitrogen sensitive gene.

DP0334-transgenic rice plants were tested two times in Hainan and Ningxia in one year. All the experiments consistently showed that over-expressing of OsGH17.2 gene in DP0334-transgenic lines decreased the yield per plant under field drought conditions. From the Ningxia field, all 12 lines were observed leaf rolling phenotypes and the average yield per plant showed significantly decreased than that of ZH11-TC and DP0158 controls. The average yield per plant of these 12 lines is 77% and 66% lower than that of ZH11-TC and DP0158 controls, respectively (Table 4). Both yield and phenotypical observations consistently showed that OsGH17.2 is a rice drought sensitive gene.

DP0786-transgenic rice plants were tested three times under field drought conditions in Hainan and Ningxia in two years. All the experiments consistently showed that over-expressing of OsDUF6 gene in DP0786-transgenic lines decreased the yield per plant under field drought conditions. From the Ningxia field, 3 of 6 lines showed significantly decreased the yield per plant than that of ZH11-TC and DP0158 controls. The average yield per plant of these 3 positive lines is 72% and 70% lower than that of ZH11-TC and DP0158 controls, respectively (Table 4). Under field low nitrogen conditions, DP0786-transgenic lines were tested two times in Beijing. Both experiments obtained the consistently results. In the second year in Beijing, all the 12 lines showed decreased yield per plant than that of ZH11-TC and DP0158 controls. Nine of twelve lines showed significantly decreased the yield per plant than that of ZH11-TC and DP0158 controls. The average yield per plant of these 12 lines is 72% and 70% lower than that of ZH11-TC and DP0158 controls, respectively (Table 4). These data consistently showed that OsDUF6 is a rice drought sensitive and low nitrogen sensitive gene.

DP0329-transgenic rice plants were tested two times in one year in Hainan and Ningxia respectively. Both experiments consistently showed that over-expressing of OsATAP1 decreased the average yield per plant under field drought conditions. From the Hainan field, 10 of 12 lines showed significantly decreased the yield per plant than that of ZH11-TC and DP0158 controls. The average yield per plant of these 10 lines is 67% and 55% lower than that of ZH11-TC and DP0158 controls, respectively, as shown in Table 4. Under field low nitrogen conditions, the DP0329-transgenic lines were tested one time in Beijing. As the results in Table 4, the average yield per plant of DP0329-transgenic plants is significantly lower than that of ZH11-TC and DP0158 controls. Nine of twelve events showed significantly decreased the average yield per plant than that of ZH11-TC control, and 3 of 12 lines showed significantly decreased the average yield per plant than that of DP0158 control. These data consistently showed that OsATAP1 is a rice drought sensitive and low nitrogen sensitive gene.

DP0780-transgenic rice plants were tested three times in two years in Hainan and Ningxia respectively. All experiments consistently showed that over-expressing of OsPCL1 gene decreased the yield per plant under field drought conditions. From the Hainan field, 2 of 7 lines showed significantly decreased the yield per plant than that of ZH11-TC and DP0158 controls. The average yield of these 7 lines is 21% and 30% lower than that of ZH11-TC and DP0158 controls, respectively, as shown in Table 4. These data consistently showed that OsPCL1 is a rice drought sensitive gene.

Taken together, these results indicate that OsBCS1-2, OsDnaJ7, OsLNTP10, OsGH17.2, OsDUF6, OsATAP1 and OsPCL1 transgenic rice plants showed drought sensitive phenotype at the vegetative stages and obtained less grain yield per plant than that of controls after drought stress. The yield and drought sensitive phenotype of the transgenic rice plants are correlated to the OsBCS1-2, OsDnaJ7 and OsGH17.2 gene expression level, respectively. The average yield per plant of OsBCS1-2, OsDnaJ7 and OsGH17.2 high-expressing lines decreased, while the average yield per plant increased in OsBCS1-2, OsDnaJ7 and OsGH17.2 low-expressing lines. OsLNTP10, OsDUF6 and OsATAP1 transgenic rice plants showed sensitive to low nitrogen stress in field.

Example 4

RNAi and CRISPR/Cas9 Vectors Construction and Transformation Construction of RNAi Constructs The forward cDNA fragments and reverse cDNA fragments were cloned for OsPCL1 gene using the template (SEQ ID NO: 51) and primers (SEQ ID NO: 52-55). Then the forward cDNA fragments, intron (SEQ ID NO: 50) and the reverse cDNA fragments were ligated together, and ligated with pMD19GW vector (SEQ ID NO: 72). After the sequences and orientation in the construct were confirmed by sequencing, the RNAi structure fragments (forward cDNA-intron-reverse cDNA) were cloned into pCAMBIA1300DsRed-35S-GW construct (SEQ ID NO: 73) to obtain the RNAi construct (DP3022).
Construction of CRISPR/Cas9 Constructs:

In the CRISPR-Cas9 system, maize Ubi promoter (SEQ ID NO: 67) drives the optimized coding sequence (SEQ ID NO: 68) of Cas9 protein; CaMV35S 3'-UTR (SEQ ID NO: 69) improves the expression level of Cas9 protein; and rice U6 promoter (SEQ ID NO: 70) drives the expression of gRNA (gRNA scaffold, SEQ ID NO: 71).

Target genomic sequences are analyzed using available tools to generate candidate sgRNA sequences. The sgRNA sequences can also be generated by other web-tools including, but not limited to, CRISPR-PLANT, available online.

The sequences of OsBCS1-2 (SEQ ID NO: 1 and SEQ ID NO: 2), OsDnaJ7 (SEQ ID NO: 4 and SEQ ID NO: 5), OsLNTP10 (SEQ ID NO: 7 and SEQ ID NO: 8), OsGH17.2 (SEQ ID NO: 10 and SEQ ID NO: 11), and OsDUF6 (SEQ ID NO: 13 and SEQ ID NO: 14) genes were analyzed to generate sgRNA sequences. The sgRNA sequences are listed in SEQ ID NO: 56-66.

One sgRNA can be used to make the genome editing construct; the sgRNA can be selected from any region of the fragment such as promoter, exon, intron and UTR. The single sgRNA can guide the Cas9 enzyme to the target region and generate the double strand break at the target DNA sequence, non-homologous end-joining (NHEJ) repairing mechanism and homology directed repair (HDR) will be triggered, and it often induces random insertion, deletion and substitution at the target site. This edit, for example, can remove an expression element in the regulatory element region to reduce the mRNA levels or can result in a structural change in the polypeptide that may result in reduced activity of the protein.

Two sgRNAs can be used to make the genome editing construct. Two or more sgRNAs can be selected from any region of the fragment such as promoter, exon, intron and UTR. This construct can lead to fragment deletion or point mutation (small insertion, deletion and substitution).

Table 5 shows the target gene, target position, and the specific strand for genome editing of OsBCS1-2, OsDnaJ7, OsLNTP10, OsGH17.2 and OsDUF6 genes and its regulatory element. DP3039 and DP2801 are constructs for editing one target position of OsLNTP10 and OsGH17.2, respectively. DP2805, DP3092 and DP3093 are constructs for editing two target positions of OsBCS1-2, OsDnaJ7 and OsDUF6, respectively. DP3041 is construct for editing three target positions of OsLNTP10 gene. For editing one target position, the target primers first anneal to form short double strand fragment, and then the fragment is inserted in pHSG396GW-URS-UC-mpCas9&rU6-DsRed construct. After confirmed the nucleotide sequence of the sgRNA fragments, the sgRNA fragments are ligated with the expression vector of pCAMBIA1300DsRed-GW-Adv.ccdB. While, for editing two or more target positions, the different primers should first anneal to form the double strand fragments, and then stack together and insert in the pHSG396GW-URS-UC-mpCas9&rU6-DsRed construct and then ligate with pCAMBIA1300DsRed-GW-Adv.ccdB verctor.

TABLE 5 gRNAs for Constructing CRISPR/Cas9 Constructs

| Construct ID | Target site ID | Target gene | Target position | Strand (+/−) | SEQ ID NO: |
|---|---|---|---|---|---|
| DP2805 | gRNA1 | OsBCS1-2 | Chr1: 23839362-23839381 | − | 56 |
|  | gRNA3 |  | Chr1: 23840101-23840120 | + | 57 |
| DP3092 | gRNA3 | OsDnaJ7 | Chr2: 31687228-31687247 | − | 58 |
|  | gRNA4 |  | Chr2: 31687631-31687650 | + | 59 |
| DP3039 | gRNA9 | OsLNTP10 | Chr5: 22828469-22828488 | + | 62 |
| DP3041 | gRNA6 |  | Chr5: 22828096-22828115 | + | 60 |
|  | gRNA8 |  | Chr5: 22828289-22828308 | − | 61 |

TABLE 5-continued gRNAs for Constructing CRISPR/Cas9 Constructs

| Construct ID | Target site ID | Target gene | Target position | Strand (+/−) | SEQ ID NO: |
|---|---|---|---|---|---|
| | gRNA10 | | Chr5: 22828474-22828493 | − | 63 |
| DP2801 | gRNA1 | OsGH17.2 | Chr1: 33949572-33949591 | − | 64 |
| DP3093 | gRNA3 | OsDUF6 | Chr3: 781754-781773 | − | 65 |
| | gRNA4 | | Chr3: 781206-781225 | − | 66 |

The RNAi and CRISPR/Cas9 constructs were transformed into the rice plants as described in Example 2.

Example 5

Identification the Cleavage Sites and the Modifications of the Drought Sensitive Genes in Genome Edited Rice Plants The primers were designed to amplify the target sequence near the genome editing target sites using the genome DNA of the transformed seedlings as template. The amplified target sequences were sequenced to confirm the editing results. Modifications such as insertion of at least one nucleotide, deletion of at least one nucleotide, replacement of at least one nucleotide were produced, which resulted the early termination of the coding sequence, translation shift and/or deletion of at least one amino acid residues.

In DP2805 rice plants, 10 modifications were identified at the expected sites. Nine mutants resulted in early stops of the ORF and further resulted in 147 to 387 amino acid residues in length; 1 mutant resulted in deletion of 27 nucleotides and deletion of 7 amino acid residues.

In DP3092 rice plants, 6 modifications were identified at the expected sites. Two mutants resulted in translation shift, but the translations were not stopped at the original stop code site; 1 mutant results in translation shift, but the translations were stopped at the original stop code site; 2 mutants resulted in early stops of the ORF and further resulted in 553 amino acid residues in length; 1 mutant resulted in insertion of one nucleotide and deletion of 169 nucleotides, and finally stopped at the original stop code site and resulted in deletion of 56 amino acid residues.

In DP3039 rice plant, 5 modifications were identified at the expected sites. Three mutants resulted in translation shift, but the translations were not stopped at the original stop code site; 1 mutant resulted in early stops of the ORF by 20 nucleotides replacement and further resulted in 74 amino acid residues in length; 1 mutant resulted in early stops of the ORF and further resulted in 28 amino acid residues in length.

In DP3041 rice plant, 29 modifications were identified at the expected sites. Six mutants resulted in translation shift, but the translations were not stopped at the original stop code site; 6 mutants resulted in early stops of the ORF and further resulted in 29 amino acid residues in length; 17 mutants were edited at the promotor and/or UTR regions.

In DP2801 rice plant, 17 modifications were identified at the expected sites. Ten mutants lead to deletion of 1 to 732 nucleotides at UTR region; 3 mutants lead to insertion of one nucleotide at UTR region; 4 mutants lead to nucleotides fragment replacement at UTR region.

In DP3093 rice plant, 9 modifications were identified at the expected sites. All the mutants resulted in frameshift mutation and were not stopped at the original stop code site.

The genome edited homozygous rice plants were used in the following functional tests.

Example 6

Characterization of the Gene Expression Suppressed or Genome Edited Rice Plants $T_2$ seeds were screened in the field to validate whether reducing the gene expression can enhance drought tolerance of the gene expression suppressed or genome edited rice plants. The screening method was described in Example 3. ZH11-TC, DP0158 or the genome edited negative rice plants were nearby the modified lines in the same block and were used as controls in the statistical analysis. The results from these studies are provided in Table 6.

TABLE 6

Agronomic Characteristics of the Gene Expression Suppressed or Genome Edited Rice Plants

| No | Construct ID | Avg. yield per plant under field drought conditions (g/plant) | Avg. yield per plant under field well-watered conditions (g/plant) |
|---|---|---|---|
| 1 | ZH11-TC | 4.29 ± 0.57 | 26.61 ± 1.27 |
| | DP0158 | 3.30 ± 0.54 | 22.34 ± 1.19 |
| | Negative | 4.03 ± 0.48 | 26.55 ± 0.87 |
| | DP2805 | 4.79 ± 0.48 [b, c] | 26.49 ± 0.72 [b] |
| 2 | ZH11-TC | 5.29 ± 0.27 | 27.30 ± 1.12 |
| | DP0158 | 4.27 ± 0.28 | 23.31 ± 1.45 |
| | DP3092 | 5.96 ± 0.23 [a, b] | 28.18 ± 1.00 [b] |
| 3 | ZH11-TC | 6.31 ± 0.36 | 27.02 ± 1.13 |
| | DP0158 | 4.75 ± 0.35 | 23.30 ± 1.44 |
| | Negative | 5.23 ± 0.30 | 25.80 ± 1.01 |
| | DP3039 | 6.90 ± 0.31 [a, b, c] | 28.40 ± 1.03 [b, c] |
| 4 | ZH11-TC | 6.31 ± 0.36 | 27.02 ± 1.13 |
| | DP0158 | 4.75 ± 0.35 | 23.30 ± 1.44 |
| | Negative | 5.23 ± 0.30 | 25.80 ± 1.01 |
| | DP3041 | 6.60 ± 0.30 [b, c] | 28.37 ± 1.00 [b, c] |
| 5 | ZH11-TC | 31.84 ± 2.61 | 41.62 ± 1.99 |
| | DP0158 | 31.69 ± 2.61 | 46.72 ± 2.06 |
| | DP2801 | 35.01 ± 2.28 [a, b] | 49.84 ± 0.99 [a] |
| 6 | ZH11-TC | 39.69 ± 2.73 | |
| | DP0158 | 37.18 ± 2.52 | |
| | Negative | 34.73 ± 3.16 | |
| | DP3093 | 42.18 ± 1.78 [b, c] | |
| 7 | ZH11-TC | 40.80 ± 1.11 | |
| | DP0158 | 39.99 ± 1.12 | |
| | DP3022 | 48.06 ± 2.26 [a, b] | |

[a] $P \leq 0.1$ compared to ZH11-TC control in field;
[b] $P \leq 0.1$ compared to DP0158 control in field;
[c] $P \leq 0.1$ compared to negative control in field.

OsBCS1-2-gene edited plants (DP2805) were tested three times under field drought and well-watered conditions in Ningxia and Hainan in two years. All experiments consistently showed that the average yield per plant of DP2805 plants increased under field drought and well-watered conditions. Under the field drought condition in Hainan, 8 of 11 lines showed significantly increased yield than that of DP0158 control. The average yield per plant of these 8 positive lines is 53% higher than that of DP0158 control. Under the field well-watered conditions in Hainan, 8 of 15 lines showed significantly increased the yield per plant than that of DP0158 control. The average yield per plant of these 8 positive lines is 27% higher than that of DP0158 control. All these results from Hainan field are shown in Table 6.

OsDnaJ7-gene edited plants (DP3092) were tested two times in one year under field drought and well-watered conditions in Ningxia and Hainan, respectively. Both experiments consistently showed that DP3092 plants increased the average yield per plant under field drought and well-watered conditions. Under the field drought conditions in Ningxia, 5 of 19 lines showed significantly increased the yield per plant than that of ZH11-TC and DP0158 controls. The average yield per plant of these 19 lines is both 10% higher than that of ZH11-TC and DP0158 controls, respectively. Under the field well-watered conditions in Ningxia, 7 of 18 lines showed significantly increased the yield per plant than that of ZH11-TC and DP0158 controls, respectively. The average yield per plant of these 18 lines is 3% and 21% higher than that of ZH11-TC and DP0158 controls, respectively. All these results from Ningxia field are shown in Table 6.

OsLNTP10-gene edited plants (DP3039) were tested one time under field drought and well-watered conditions in Hainan. The experiment showed that DP3039 plants increased the average yield per plant under field drought and well-watered conditions. Under the field drought conditions, 6 of 8 lines showed significantly increased the yield per plant than that of ZH11-TC and DP0158 controls. The average yield per plant of these 8 lines is 9% and 45% higher than that of ZH11-TC and DP0158 controls, respectively. Under the field well-watered conditions, 6 of 10 lines showed significantly increased the yield per plant than that of ZH11-TC and DP0158 controls. The average yield per plant of these 10 lines is 5% and 22% higher than that of ZH11-TC and DP0158 controls, respectively. All these results from Hainan field are shown in Table 6.

OsLNTP10-gene edited plants (DP3041) were tested one time under field drought and well-watered conditions in Hainan. The experiment showed that DP3041 plants increased the average yield per plant under field drought and well-watered conditions. Under the field drought conditions, 7 of 11 lines showed significantly increased the yield per plant than that of ZH11-TC and DP0158 controls. The average yield per plant of these 11 lines is 5% and 39% higher than that of ZH11-TC and DP0158 controls, respectively. Under the field well-watered conditions, 6 of 13 lines showed significantly increased the yield per plant than that of ZH11-TC and DP0158 controls. The average yield per plant of these 13 lines is 5% and 21% higher than that of ZH11-TC and DP0158 controls, respectively. All these results from Hainan field are shown in Table 6.

OsGH17.2-gene edited plants (DP2801) were tested one time under field drought and well-watered conditions in Ningxia. The experiment showed that DP2801 plants increased the average yield per plant. Under the field drought conditions, 5 of 19 lines showed significantly increased the yield per plant than that of ZH11-TC and DP0158 controls. The average yield per plant of these 19 lines is both 10% higher than that of ZH11-TC and DP0158 controls. Under the field well-watered conditions, 7 of 18 lines showed significantly increased the yield per plant than that of ZH11-TC and DP0158 controls, respectively. The average yield per plant of these 18 lines is 20% and 7% higher than that of ZH11-TC and DP0158 controls, respectively. All these results from Ningxia field are shown in Table 6.

OsDUF6-gene edited plants (DP3093) were tested one time under field drought condition in Ningxia. The experiment showed that DP3093 plants increased the average yield per plant. Under the field drought conditions, 4 of 10 lines showed significantly increased the yield per plant than that of ZH11-TC and DP0158 controls. The average yield per plant of these 10 lines is 6% and 13% higher than that of ZH11-TC and DP0158 controls, respectively. All these results from Ningxia field are shown in Table 6.

OsPCL1-gene suppression plants (DP3022) were tested two times under field drought condition in Ningxia and Hainan. The experiments showed that DP3022 plants increased the average yield per plant. From the Ningxia field, 5 of 7 lines showed significantly increased the yield per plant than that of ZH11-TC and DP0158 controls. The average yield per plant of these 7 lines is 18% and 20% higher than that of ZH11-TC and DP0158 controls, respectively, as shown in Table 6.

Taken together, these results indicate that OsBCS1-2, OsDnaJ7, OsLNTP10, OsGH17.2, OsDUF6, OsATAP1 and OsPCL1-gene edited or gene suppression rice plants showed drought tolerance phenotype at the vegetative stages and increased grain yield per plant than that of controls after drought stress and/or normal conditions.

Example 7

Transformation and Evaluation of Maize with Decreased Expression of the Homolog of the Rice Drought Sensitive Genes Maize plants can be modified (e.g., suppression DNA construct or targeted genetic modification), as described herein, to reduce the expression and/or activity of the homolog from maize. Expression of the suppression elements in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The suppression DNA construct can be introduced into maize cells by particle bombardment substantially as described in International Patent Publication WO 2009/006276. Alternatively, maize plants can be transformed with the suppression DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999. Alternatively, a targeted genetic modification can be introduced at a genomic locus encoding the homologous protein using methods known in the art.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

Example 8

Evaluation of Sorghum with Decreased Expression of the Homolog of the Rice Drought Sensitive Genes Sorghum can be modified (e.g., suppression DNA construct or targeted genetic modification), as described herein, to reduce the expression and/or activity of the homolog from sorghum.

Example 9

Evaluation of Soybean with Decreased Expression of the Homolog of the Rice Drought Sensitive Genes Soybean plants can be modified (e.g., suppression DNA construct or targeted genetic modification), as described herein, to reduce the expression and/or activity of the homolog from *Glycine max*.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

Example 10

Laboratory Drought Screening of Rice Drought Sensitive Genes in *Arabidopsis*

To understand whether rice drought tolerance genes can improve dicot plants' drought tolerance, or other traits, the rice vectors described herein can be transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in dicot plants to enhance drought tolerance.

---

What is claimed is:

1. A modified plant or seed comprising a targeted genetic modification or suppression DNA construct decreasing the expression or activity of a polypeptide comprising an amino acid sequence that is at least 95% identical to SEQ ID NO: 9 when compared to the expression or activity of the corresponding polypeptide in a control plant, wherein the plant exhibits increased drought tolerance, increased nitrogen stress tolerance, and/or increased grain yield.

2. The modified plant or seed of claim 1, wherein the plant comprises a suppression DNA construct comprising at least one regulatory element operably linked to the suppression elements, wherein the suppression elements comprise at least 100 contiguous base pairs of (a) a polynucleotide with nucleotide sequence of at least 98% identity to SEQ ID NO: 8; or (b) a polynucleotide encoding a polypeptide with amino acid sequence with at least 95% sequence identity to SEQ ID NO: 9; or (c) the full complement of the nucleotide sequence of (a) or (b).

3. The modified plant or seed of claim 2, wherein the suppression elements comprise SEQ ID NO: 51.

4. The modified plant or seed of claim 1, wherein the plant comprises a targeted genetic modification at an endogenous genomic locus comprising a polynucleotide sequence encoding a polypeptide comprising an amino acid sequence that is at least 95% identical to SEQ ID NO: 9, the targeted genetic modification introducing a modification decreasing expression or activity of the polypeptide.

5. The plant of claim 4, wherein the genetic modification is introduced by one or more gRNAs comprising a sequence selected from the group consisting of SEQ ID NOs: 56-66.

6. The plant of claim 1, wherein said plant is selected from the group consisting of rice, maize, soybean, sunflower, sorghum, canola, wheat, alfalfa, cotton, barley, millet, sugar cane and switchgrass.

7. A method of increasing drought tolerance in a plant, the method comprising:
(a) introducing into a regenerable plant cell a suppression DNA construct, the suppression DNA construct silencing a gene encoding a polypeptide comprising an amino acid sequence that is at least 95% identical to SEQ ID NO: 9; and
(b) regenerating a modified plant from the regenerable plant cell, wherein the plant comprises the suppression DNA construct and has increased drought tolerance as compared to a control plant not comprising the suppression DNA construct.

8. The method of claim 7, wherein the suppression DNA construct comprises at least one heterologous regulatory element operably linked to suppression elements, wherein the suppression elements comprise at least 100 contiguous base pairs of (a) a polynucleotide with nucleotide sequence of at least 98% identity to SEQ ID NO: 8; or (b) a polynucleotide encoding a polypeptide with amino acid sequence of at least 95% sequence identity to SEQ ID NO: 9; or (c) the full complement of the nucleotide sequence of (a) or (b).

9. The method of claim 7, wherein the suppression elements comprise a polynucleotide with the nucleotide sequence of SEQ ID NO: 51.

10. A method of increasing drought tolerance in a plant, the method comprising:
(a) introducing in a regenerable plant cell a targeted genetic modification at an endogenous genomic locus encoding a polypeptide comprising an amino acid sequence that is at least 95% identical to SEQ ID NO: 9, the targeted genetic modification introducing a modification decreasing expression or activity of the polypeptide; and
(b) generating the plant, wherein the plant comprises the targeted genetic modification and has increased drought tolerance as compared to a control plant not comprising the targeted genetic modification.

11. The method of claim 10, wherein the targeted genetic modification is introduced using a CRISPR-Cas endonuclease.

12. The method of claim 7, wherein said plant is selected from the group consisting of rice, maize, soybean, sunflower, sorghum, canola, wheat, alfalfa, cotton, barley, millet, sugar cane and switchgrass.

13. The method of claim 10, wherein said plant is selected from the group consisting of rice, maize, soybean, sunflower, sorghum, canola, wheat, alfalfa, cotton, barley, millet, sugar cane and switchgrass.

14. The method of claim 10, wherein the targeted genetic modification is introduced in (a) the coding region; (b) a non-coding region; (c) a regulatory sequence; (d) an untranslated region; or (e) any combination of (a)-(d) of the genomic locus encoding the polypeptide.

* * * * *

SEQUENCE LISTING

```
<160> NUMBER OF SEQ ID NOS: 139

<210> SEQ ID NO 1
<211> LENGTH: 1540
<212> TYPE: DNA
<213> ORGANISM: Oryza sativa

<400> SEQUENCE: 1
gttttcagag acgtaccaga gccaacagca gcagtaggct cgccggacgg ccagccagcc      60
atggcgtcct acgacaaggc catcgagtcg tacaagaggg ccgtcaccac ggcggcgtcc     120
ctggcggcgt cggcgatgct ggtgcgcggc gtcgtgaacg agctggtgcc gtacgaggtg     180
cgggacctgc tcttctccgg cgtcgggtac ctgcggtcgc gcatgtcgtc ccagcacatg     240
gtcatcatcg aggagaccga gggctggacc aacaaccagc tctacgacgc cgtcaggacg     300
tacctcgcca ccaggatcaa caccgacatg cagcgcctcc gggtcagccg cgtcgacgag     360
accaagagca tgatgttcag catggaggag ggcgaggaga tggccgacgt ccatgagggc     420
tccgagttca ggtggcgcct cgtctgccgc gacaactcca gcagcagcaa cggcaacggc     480
aacggccgtg gcgggaacgg caactaccgg ctcgaggtcc ggtccttcga gatgagcttc     540
cacaagaagc acaaggacaa ggccctcaac tcttacctcc ctcacatcct ggccactgca     600
aagaagatca aggatcagga caggacgctg aagatctaca tgaacgaagg tgagtcgtgg     660
ttcgccatcg acctccacca cccctcgacc ttcaccacgc tcgccatgga tcacaagcag     720
aagcagtcag ttatggatga tcttgagagg ttcatcaagc gaaaggaata ctacaagaag     780
attggcaaag catggaaacg ggggtacctt ctgtatggcc cacctggaac tggcaagtcc     840
agcttgattg cagccatggc caattacctc aagttcgacg tatatgatct cgagctgact     900
gaggtcaact ggaactcaac ccttcgacgg ttgctcatcg ggatgaccaa caggtcaatc     960
ctagttatag aagatatcga ctgcactcta gagctacaac aacgggagga aggtcaagag    1020
agttccaaat ccaatccttc agaggacaag gtaacactat ctgggctact caacttcgtg    1080
```

```
gatgggcttt ggtcaacaag tggggaggag agaataattg tcttcacgac aaactacaag    1140
gagaggctcg accctgcgct ctgcgtcct ggcaggatgg acatgcatgt ccatatgggt    1200
tactgctgcc cagagtcatt tagaattctg gcctctaact accactccat tgataaccat    1260
gccacatacc cagagataga agagttgatc aaggaggtca tggtgacacc agcagaggta    1320
gctgaggtgc tcatgaggaa tgatgacact gatgttgccc ttgaaggcct tattcagttc    1380
ctcaagagaa agaaagatgt tggcaaggaa ggcaaagctg aaaatgtgga gcaggtggtg    1440
aaggcagaag aaacagagaa agggatgatg aagaaaaatg atgtcccaga gaatcaagat    1500
ccccaagatg caagcaaata atgatgctta acagtgtgc                          1540
```

```
<210> SEQ ID NO 2
<211> LENGTH: 1461
<212> TYPE: DNA
<213> ORGANISM: Oryza sativa

<400> SEQUENCE: 2
```

```
atggcgtcct acgacaaggc catcgagtcg tacaagaggg ccgtcaccac ggcggcgtcc      60
ctggcggcgt cggcgatgct ggtgcgcggc gtcgtgaacg agctggtgcc gtacgaggtg    120
cgggacctgc tcttctccgg cgtcgggtac ctgcggtcgc gcatgtcgtc ccagcacatg    180
gtcatcatcg aggagaccga gggctggacc aacaaccagc tctacgacgc cgtcaggacg    240
tacctcgcca ccaggatcaa caccgacatg cagcgcctcc gggtcagccg cgtcgacgag    300
accaagagca tgatgttcag catggaggag ggcgaggaga tggccgacgt ccatgagggc    360
tccgagttca ggtggcgcct cgtctgccgc gacaactcca gcagcagcaa cggcaacggc    420
aacggccgtg gcgggaacgg caactaccgg ctcgaggtcc ggtccttcga gatgagcttc    480
cacaagaagc acaaggacaa ggccctcaac tcttacctcc ctcacatcct ggccactgca    540
aagaagatca aggatcagga caggacgctg aagatctaca tgaacgaagg tgagtcgtgg    600
ttcgccatcg acctccacca cccctcgacc ttcaccacgc tcgccatgga tcacaagcag    660
aagcagtcag ttatggatga tcttgagagg ttcatcaagc gaaaggaata ctacaagaag    720
attggcaaag catggaaacg ggggtacctt ctgtatggcc cacctggaac tggcaagtcc    780
agcttgattg cagccatggc caattcctc aagttcgacg tatatgatct cgagctgact    840
gaggtcaact ggaactcaac ccttcgacgg ttgctcatcg ggatgaccaa caggtcaatc    900
ctagttatag aagatatcga ctgcactcta gagctacaac aacgggagga aggtcaagag    960
agttccaaat ccaatccttc agaggacaag gtaacactat ctgggctact caacttcgtg    1020
gatgggcttt ggtcaacaag tggggaggag agaataattg tcttcacgac aaactacaag    1080
gagaggctcg accctgcgct ctgcgtcct ggcaggatgg acatgcatgt ccatatgggt    1140
tactgctgcc cagagtcatt tagaattctg gcctctaact accactccat tgataaccat    1200
gccacatacc cagagataga agagttgatc aaggaggtca tggtgacacc agcagaggta    1260
gctgaggtgc tcatgaggaa tgatgacact gatgttgccc ttgaaggcct tattcagttc    1320
ctcaagagaa agaaagatgt tggcaaggaa ggcaaagctg aaaatgtgga gcaggtggtg    1380
aaggcagaag aaacagagaa agggatgatg aagaaaaatg atgtcccaga gaatcaagat    1440
ccccaagatg caagcaaata a                                             1461
```

```
<210> SEQ ID NO 3
<211> LENGTH: 486
<212> TYPE: PRT
<213> ORGANISM: Oryza sativa
```

<400> SEQUENCE: 3

```
Met Ala Ser Tyr Asp Lys Ala Ile Glu Ser Tyr Lys Arg Ala Val Thr
1               5                   10                  15

Thr Ala Ala Ser Leu Ala Ala Ser Ala Met Leu Val Arg Gly Val Val
            20                  25                  30

Asn Glu Leu Val Pro Tyr Glu Val Arg Asp Leu Leu Phe Ser Gly Val
        35                  40                  45

Gly Tyr Leu Arg Ser Arg Met Ser Ser Gln His Met Val Ile Ile Glu
    50                  55                  60

Glu Thr Glu Gly Trp Thr Asn Asn Gln Leu Tyr Asp Ala Val Arg Thr
65                  70                  75                  80

Tyr Leu Ala Thr Arg Ile Asn Thr Asp Met Gln Arg Leu Arg Val Ser
                85                  90                  95

Arg Val Asp Glu Thr Lys Ser Met Met Phe Ser Met Glu Glu Gly Glu
            100                 105                 110

Glu Met Ala Asp Val His Glu Gly Ser Glu Phe Arg Trp Arg Leu Val
        115                 120                 125

Cys Arg Asp Asn Ser Ser Ser Asn Gly Asn Gly Asn Gly Arg Gly
130                 135                 140

Gly Asn Gly Asn Tyr Arg Leu Glu Val Arg Ser Phe Glu Met Ser Phe
145                 150                 155                 160

His Lys Lys His Lys Asp Lys Ala Leu Asn Ser Tyr Leu Pro His Ile
                165                 170                 175

Leu Ala Thr Ala Lys Lys Ile Lys Asp Gln Asp Arg Thr Leu Lys Ile
            180                 185                 190

Tyr Met Asn Glu Gly Glu Ser Trp Phe Ala Ile Asp Leu His His Pro
        195                 200                 205

Ser Thr Phe Thr Thr Leu Ala Met Asp His Lys Gln Lys Gln Ser Val
210                 215                 220

Met Asp Asp Leu Glu Arg Phe Ile Lys Arg Lys Glu Tyr Tyr Lys Lys
225                 230                 235                 240

Ile Gly Lys Ala Trp Lys Arg Gly Tyr Leu Leu Tyr Gly Pro Pro Gly
                245                 250                 255

Thr Gly Lys Ser Ser Leu Ile Ala Ala Met Ala Asn Tyr Leu Lys Phe
            260                 265                 270

Asp Val Tyr Asp Leu Glu Leu Thr Glu Val Asn Trp Asn Ser Thr Leu
        275                 280                 285

Arg Arg Leu Leu Ile Gly Met Thr Asn Arg Ser Ile Leu Val Ile Glu
290                 295                 300

Asp Ile Asp Cys Thr Leu Glu Leu Gln Gln Arg Glu Glu Gly Gln Glu
305                 310                 315                 320

Ser Ser Lys Ser Asn Pro Ser Glu Asp Lys Val Thr Leu Ser Gly Leu
                325                 330                 335

Leu Asn Phe Val Asp Gly Leu Trp Ser Thr Ser Gly Glu Glu Arg Ile
            340                 345                 350

Ile Val Phe Thr Thr Asn Tyr Lys Glu Arg Leu Asp Pro Ala Leu Leu
        355                 360                 365

Arg Pro Gly Arg Met Asp Met His Val His Met Gly Tyr Cys Cys Pro
370                 375                 380

Glu Ser Phe Arg Ile Leu Ala Ser Asn Tyr His Ser Ile Asp Asn His
385                 390                 395                 400

Ala Thr Tyr Pro Glu Ile Glu Glu Leu Ile Lys Glu Val Met Val Thr
```

```
                    405                 410                 415
Pro Ala Glu Val Ala Glu Val Leu Met Arg Asn Asp Thr Asp Val
            420                 425                 430

Ala Leu Glu Gly Leu Ile Gln Phe Leu Lys Arg Lys Asp Val Gly
            435                 440                 445

Lys Glu Gly Lys Ala Glu Asn Val Glu Gln Val Val Lys Ala Glu Glu
            450                 455                 460

Thr Glu Lys Gly Met Met Lys Lys Asn Asp Val Pro Glu Asn Gln Asp
465                 470                 475                 480

Pro Gln Asp Ala Ser Lys
                485

<210> SEQ ID NO 4
<211> LENGTH: 3391
<212> TYPE: DNA
<213> ORGANISM: Oryza sativa

<400> SEQUENCE: 4
```

| | | | | | |
|---|---|---|---|---|---|
| ctcctccaaa | aatattccca | ccccaacctc | gcaaccccgc | cgttcgttgc | cagccaggag | 60 |
| ccaacgcccg | cgctccctcg | tcctcgtcgt | gaccccttc | cccgcctccc | ggtgcgcgcg | 120 |
| ctcgccacga | cgcggcacga | cacaacggcc | ggagcgggcg | cgcggccgcg | gacgtcgccg | 180 |
| gtcgccatga | cggagtcgcg | ccgcccgccg | tccggctgcg | cgatgttcgg | catctacagc | 240 |
| ggcatgttcc | ggcgacgccg | gtcaaactcc | atgtcctcca | tcgcccgcat | caacggggtc | 300 |
| ccacccgcca | ccgccgagca | cgagcacgag | gccgaggcca | aggcggcctc | cgcgccggcg | 360 |
| aaccaggcgc | accggaaggg | cggcggcgtc | cacgacgact | cgtccctcgc | gcaccgcccg | 420 |
| gccaagccgc | tcccagggac | gaacaacggc | gcgcagcgtg | cccatgcacc | ggcaagcgac | 480 |
| agggccgtac | acgcgacgaa | ggcggcgaac | ggcggggcga | ggaatgcggc | gtcggcggca | 540 |
| ccggccgcgg | agtacaccgg | gatggcagcg | gagctcgaca | gatgatcct | cgatcaccag | 600 |
| agggtcaagg | gcaccacgca | gctggtgcgc | gcaacctccg | gcaacatgat | gctccaccgc | 660 |
| aacctcggca | acctcaatgc | cggcgtcccc | ggcgcgtcgg | cgcggagctc | gctggaacgc | 720 |
| aaccccgcca | acaagccggc | gaacgagcgg | aaggccacca | cgggtacgc | gttctccggc | 780 |
| ctcgggaaca | tcgtcaagga | gccgagggcg | ccgccggcgt | cgtccgagct | gtgccgcgcg | 840 |
| ctgtcgcacc | ggacgacccc | cgagaagctc | aaggagatgg | gcaacgagga | gtaccggcag | 900 |
| gggcattacg | cggaggcggt | ggcgctctac | gaccaggcca | tcatggtgga | tccaacgcgg | 960 |
| ccggcgtact | ggagcaacaa | ggccgccgcg | ctcgccgcgc | tcggccgcct | catcgaggcc | 1020 |
| gtcggcgact | gcagggaggc | tgtccggatc | gacccgtcgt | acggccgcgc | gcaccaccgc | 1080 |
| ctcggcgggc | tgtatctcag | gtacgcgcat | tccgcatttg | ggcgttcaga | ttgttcatca | 1140 |
| ccaatgtcat | tagtgcaatt | gaaatcttta | ggaatccggc | aaaagaaatg | aaattaacta | 1200 |
| gtatttgcac | aggaattctt | aaggacactg | atcaactgga | attaggtctt | tagtaaaaaa | 1260 |
| aaactggaat | taggtcagtt | catatcgtga | cttgatttgg | aaatcagatt | tgactagcac | 1320 |
| catagttata | gtagcatgat | ctaattctat | tggaaaaggg | atttgatcat | ggcttttgac | 1380 |
| aagacgacaa | ctgattgttc | aactttaccc | actaatattt | cgtaggcaat | tattttggcc | 1440 |
| gaaaataggt | gcaccaaatt | tagatgttgg | ggaattagtt | aatggaatgg | ctaatttgca | 1500 |
| tcagcattgg | ctcttttgtca | atgatgactt | attcattttt | ttttgaaaga | aatgaattca | 1560 |
| tggttgagta | ggggtactgc | tattctttct | tggaaatctc | aaactttcc | cttaagaaat | 1620 |

```
ggaattaccc attgtttgtg attaggcaat agtacaattt gatacatgtg ctcctttgga    1680
acatttgatc atttgatcat tggtttagca ggtcaagcaa gaccttctgc cgtaaattac    1740
tctagccatt tccgatcaca ttgatgattg gtaattccaa tagctaatca cttcctcgac    1800
aagcattctc acacttcttt ttgaagagaa tgattgcagc actagcttag tactagcttg    1860
ttgaattttg cgatctgtca gagaacaagt ccacacacac ttcattttc tactgcctac    1920 tctgtactga gtactgacat tgttttgttt acacaacacc acgatgattt ttatcgatag    1980
taaacttaca ccgttttag ttccaaaata attcttcaaa cttctaactt tttcatcaca    2040
tcaaaacttt cctacacaca taaactttca atttttctgt catatcgttc caatttcaac    2100
caaacttcta attttggtgt gaactaaaca cagccattgc tgttattgct cagattagga    2160
gaacctgaca aggcaatcca ccacttcaag caatcggcga acgactcgac gggcgcggac    2220
gtgtcgcgcg cacagtcggt caagagccgc gtcgccaagt gcggcgacgc gcgcaagctg    2280
aggaactgga tcacggtgct gcaggaatcg caggccgccg tcgccgacgg cgccgactgc    2340
gccccacagg tgagcgtccc tcgcgccacg tgaaagaaaa agaaaaagaa aaggaaagaa    2400
aacgtttacg cgacacgacc agcatccgat caaatgcagc gatctgatca tacgtctctg    2460
tcacgatgga atttttttct ggaaggtcat ggcgttgcaa gccgaggccc tggtgaagct    2520
gagccggcac gacgaggccg acgctgtgct gggcggcgcg ccgcggttcg gcgtcgacga    2580
atcgaccaag ttcttcggca ccgtcgccca tgcctacgtc ctcatgatcc gtgctcaggt    2640
cgacatggct gctgggaggt tcgttctcaa cgttgttttt tatttttttt cctcttcctc    2700
gatcaaatgg agatcagcag agatgagatg gctgtattct gatgccgtcg tgttcatgct    2760
ggatgtgtga aggtttgagg acgcggtggc gacggcgcag acggcgtgcc agctcgaccc    2820
gagcaaccgg gagatcgcga acgtgcaccg gcgggccaag gtggtggcgt cggcgaggct    2880
gcgcgggaac gacctcttca aggcgtccag gttcgccgag gcgtgcgccg cctactgcga    2940
gggcctcgac agggagaccg gcaacgccgt gctgctctgc aaccgcgccg cgtgccacgc    3000
gaggctcgcg cggtacgaga aggccgtcga ggactgcaac ggcgcgctcg ccatgcggcc    3060
ggcgtacagc aaggcgcgcc tcaggagggc cgactgcaac gtcaaggttc gctgcctccg    3120
ccgtgccgga atttttcatc gccataccctg acatgaatgc gcgatctcat ttttgtcaac    3180 gaacttttg tctgtgtttt tgtgatcagc tggagagatg ggaagcgtcg ttgcgagatt    3240
accaggtgct gatccaagaa ctcccggaga acgaggacat gaagaaggcg ctgtccgagg    3300
tcgaagccaa gctccggagc cagaggaatg ggggcattgc aagcagatca caacagtgac    3360
gccatgtaac cacagctagc cttaccaatt c                                   3391
```

<210> SEQ ID NO 5
<211> LENGTH: 1767
<212> TYPE: DNA
<213> ORGANISM: Oryza sativa

<400> SEQUENCE: 5

```
atgacggagt cgcgccgccc gccgtccggc tgcgcgatgt tcggcatcta cagcggcatg     60
ttccggcgac gccggtcaaa ctccatgtcc tccatcgccc gcatcaacgg ggtcccaccc    120
gccaccgccg agcacgagca cgaggccgag gccaaggcgg cctccgcgcc ggcgaaccag    180
gcgcaccgga agggcggcgg cgtccacgac gactcgtccc tcgcgcaccg cccggccaag    240
ccgctcccag ggacgaacaa cggcgcgcag cgtgcccatg caccggcaag cgacagggcc    300
gtacacgcga cgaaggcggc gaacggcggg gcgaggaatg cggcgtcggc ggcaccggcc    360
```

-continued

```
gcggagtaca ccgggatggc agcggagctc gacaagatga tcctcgatca ccagagggtc      420
aagggcacca cgcagctggt gcgcgcaacc tccggcaaca tgatgctcca ccgcaacctc      480
ggcaacctca atgccggcgt ccccggcgcg tcggcgcgga gctcgctgga acgcaacccc      540
gccaacaagc cggcgaacga gcggaaggcc accaacgggt acgcgttctc cggcctcggg      600
aacatcgtca aggagccgag ggcgccgccg gcgtcgtccg agctgtgccg cgcgctgtcg      660
caccggacgg accccgagaa gctcaaggag atgggcaacg aggagtaccg ggaggggcat      720
tacgcggagg cggtggcgct ctacgaccag gccatcatgg tggatccaac gcggccggcg      780
tactggagca caaggccgc cgcgctcgcc gcgctcggcc gcctcatcga ggccgtcggc       840
gactgcaggg aggctgtccg gatcgacccg tcgtacggcc gcgcgcacca ccgcctcggc      900
gggctgtatc tcagattagg agaacctgac aaggcaatcc accacttcaa gcaatcggcg      960
aacgactcga cgggcgcgga cgtgtcgcgc gcacagtcgg tcaagagccg cgtcgccaag     1020
tgcggcgacg cgcgcaagct gaggaactgg atcacggtgc tgcaggaatc gcaggccgcc     1080
gtcgccgacg cgccgactg cgccccacag gtcatggcgt tgcaagccga ggccctggtg      1140
aagctgagcc ggcacgacga ggccgacgct gtgctgggcg cgcgccgcg gttcggcgtc      1200 gacgaatcga ccaagttctt cggcaccgtc gcccatgcct acgtcctcat gatccgtgct     1260
caggtcgaca tggctgctgg gaggtttgag gacgcggtgg cgacggcgca gacggcgtgc     1320
cagctcgacc cgagcaaccg ggagatcgcg aacgtgcacc ggcgggccaa ggtggtggcg     1380
tcggcgaggc tgcgcgggaa cgacctcttc aaggcgtcca ggttcgccga ggcgtgcgcc     1440
gcctactgcg agggcctcga cagggagacc ggcaacgccg tgctgctctg caaccgcgcc     1500
gcgtgccacg cgaggctcgc gcggtacgag aaggccgtcg aggactgcaa cggcgcgctc     1560
gccatgcggc cggcgtacag caaggcgcgc ctcaggaggg ccgactgcaa cgtcaagctg     1620
gagagatggg aagcgtcgtt gcgagattac caggtgctga tccaagaact cccggagaac     1680
gaggacatga agaaggcgct gtccgaggtc gaagccaagc tccggagcca gaggaatggg     1740
ggcattgcaa gcagatcaca acagtga                                         1767
```

<210> SEQ ID NO 6
<211> LENGTH: 588
<212> TYPE: PRT
<213> ORGANISM: Oryza sativa

<400> SEQUENCE: 6

```
Met Thr Glu Ser Arg Arg Pro Pro Ser Gly Cys Ala Met Phe Gly Ile
1               5                   10                  15

Tyr Ser Gly Met Phe Arg Arg Arg Ser Asn Ser Met Ser Ser Ile
                20                  25                  30

Ala Arg Ile Asn Gly Val Pro Pro Ala Thr Ala Glu His Glu His Glu
            35                  40                  45

Ala Glu Ala Lys Ala Ala Ser Ala Pro Ala Asn Gln Ala His Arg Lys
        50                  55                  60

Gly Gly Val His Asp Asp Ser Ser Leu Ala His Arg Pro Ala Lys
65                  70                  75                  80

Pro Leu Pro Gly Thr Asn Asn Gly Ala Gln Arg Ala His Ala Pro Ala
                85                  90                  95

Ser Asp Arg Ala Val His Ala Thr Lys Ala Ala Asn Gly Gly Ala Arg
            100                 105                 110

Asn Ala Ala Ser Ala Ala Pro Ala Ala Glu Tyr Thr Gly Met Ala Ala
```

```
              115                 120                 125
Glu Leu Asp Lys Met Ile Leu Asp His Gln Arg Val Lys Gly Thr Thr
    130                 135                 140
Gln Leu Val Arg Ala Thr Ser Gly Asn Met Met Leu His Arg Asn Leu
145                 150                 155                 160
Gly Asn Leu Asn Ala Gly Val Pro Gly Ala Ser Ala Arg Ser Ser Leu
                165                 170                 175
Glu Arg Asn Pro Ala Asn Lys Pro Ala Asn Glu Arg Lys Ala Thr Asn
            180                 185                 190
Gly Tyr Ala Phe Ser Gly Leu Gly Asn Ile Val Lys Glu Pro Arg Ala
        195                 200                 205
Pro Pro Ala Ser Ser Glu Leu Cys Arg Ala Leu Ser His Arg Thr Asp
    210                 215                 220
Pro Glu Lys Leu Lys Glu Met Gly Asn Glu Glu Tyr Arg Glu Gly His
225                 230                 235                 240
Tyr Ala Glu Ala Val Ala Leu Tyr Asp Gln Ala Ile Met Val Asp Pro
                245                 250                 255
Thr Arg Pro Ala Tyr Trp Ser Asn Lys Ala Ala Leu Ala Ala Leu
            260                 265                 270
Gly Arg Leu Ile Glu Ala Val Gly Asp Cys Arg Glu Ala Val Arg Ile
        275                 280                 285
Asp Pro Ser Tyr Gly Arg Ala His His Arg Leu Gly Gly Leu Tyr Leu
    290                 295                 300
Arg Leu Gly Glu Pro Asp Lys Ala Ile His His Phe Lys Gln Ser Ala
305                 310                 315                 320
Asn Asp Ser Thr Gly Ala Asp Val Ser Arg Ala Gln Ser Val Lys Ser
                325                 330                 335
Arg Val Ala Lys Cys Gly Asp Ala Arg Lys Leu Arg Asn Trp Ile Thr
            340                 345                 350
Val Leu Gln Glu Ser Gln Ala Ala Val Ala Asp Gly Ala Asp Cys Ala
        355                 360                 365
Pro Gln Val Met Ala Leu Gln Ala Glu Ala Leu Val Lys Leu Ser Arg
    370                 375                 380
His Asp Glu Ala Asp Ala Val Leu Gly Gly Ala Pro Arg Phe Gly Val
385                 390                 395                 400
Asp Glu Ser Thr Lys Phe Phe Gly Thr Val Ala His Ala Tyr Val Leu
                405                 410                 415
Met Ile Arg Ala Gln Val Asp Met Ala Ala Gly Arg Phe Glu Asp Ala
            420                 425                 430
Val Ala Thr Ala Gln Thr Ala Cys Gln Leu Asp Pro Ser Asn Arg Glu
        435                 440                 445
Ile Ala Asn Val His Arg Arg Ala Lys Val Val Ser Ala Arg Leu
    450                 455                 460
Arg Gly Asn Asp Leu Phe Lys Ala Ser Arg Phe Ala Glu Ala Cys Ala
465                 470                 475                 480
Ala Tyr Cys Glu Gly Leu Asp Arg Glu Thr Gly Asn Ala Val Leu Leu
                485                 490                 495
Cys Asn Arg Ala Ala Cys His Ala Arg Leu Ala Arg Tyr Glu Lys Ala
            500                 505                 510
Val Glu Asp Cys Asn Gly Ala Leu Ala Met Arg Pro Ala Tyr Ser Lys
        515                 520                 525
Ala Arg Leu Arg Arg Ala Asp Cys Asn Val Lys Leu Glu Arg Trp Glu
    530                 535                 540
```

```
Ala Ser Leu Arg Asp Tyr Gln Val Leu Ile Gln Glu Leu Pro Glu Asn
        545                 550                 555                 560

Glu Asp Met Lys Lys Ala Leu Ser Glu Val Glu Ala Lys Leu Arg Ser
                565                 570                 575

Gln Arg Asn Gly Gly Ile Ala Ser Arg Ser Gln Gln
            580                 585
```

<210> SEQ ID NO 7
<211> LENGTH: 317
<212> TYPE: DNA
<213> ORGANISM: Oryza sativa

<400> SEQUENCE: 7

```
caactgagca agaactgaag aaaatagaga gagagaagcc atggagcagg ggtacggctg      60
ctacagctac taccagcagt acaagagcag cggcagtttc atcagtggca aggagaagag     120
gccgccgctg aagaggggc agctgaagcg gcagattgtg aggacgctca gcaacctcat      180
ggcgccggcg acgaggagca gcggcgacgc tgctgctgct gcagactcca agaagaaggc     240
agcggatcgc agcagcttca ggagagaagc cagctacaac tgaatcgatc caatcgaaca     300
gcaacatcat catcatc                                                    317
```

<210> SEQ ID NO 8
<211> LENGTH: 243
<212> TYPE: DNA
<213> ORGANISM: Oryza sativa

<400> SEQUENCE: 8

```
atggagcagg ggtacggctg ctacagctac taccagcagt acaagagcag cggcagtttc      60
atcagtggca aggagaagag gccgccgctg aagaggggc agctgaagcg gcagattgtg     120
aggacgctca gcaacctcat ggcgccggcg acgaggagca gcggcgacgc tgctgctgct     180
gcagactcca agaagaaggc agcggatcgc agcagcttca ggagagaagc cagctacaac     240
tga                                                                   243
```

<210> SEQ ID NO 9
<211> LENGTH: 80
<212> TYPE: PRT
<213> ORGANISM: Oryza sativa

<400> SEQUENCE: 9

```
Met Glu Gln Gly Tyr Gly Cys Tyr Ser Tyr Tyr Gln Gln Tyr Lys Ser
1               5                   10                  15

Ser Gly Ser Phe Ile Ser Gly Lys Glu Lys Arg Pro Pro Leu Lys Arg
            20                  25                  30

Gly Gln Leu Lys Arg Gln Ile Val Arg Thr Leu Ser Asn Leu Met Ala
        35                  40                  45

Pro Ala Thr Arg Ser Ser Gly Asp Ala Ala Ala Ala Asp Ser Lys
    50                  55                  60

Lys Lys Ala Ala Asp Arg Ser Ser Phe Arg Arg Glu Ala Ser Tyr Asn
65                  70                  75                  80
```

<210> SEQ ID NO 10
<211> LENGTH: 1115
<212> TYPE: DNA
<213> ORGANISM: Oryza sativa

<400> SEQUENCE: 10

-continued

```
gaggagtcgg aaaggagata cagttctcag atagtttctg ctacctttgc tgccgcgcgc      60
tgcagaagat cggcgagatg gatgctgtgt tggttaccgc cgccatcttc gggttgctgc     120
tctgcggctg ctcggtttca ggagtggaag gtatcggtgt gaactatggc atgatcggca     180
acaacctccc gtcgccggac aaggtcatcg ccctgtacag agccagcaac atcaccgaca     240
tccgcctctt ccacccggac accaccgtgc tcgccgcgct ccgcggctcg ggcctcggcg     300
tcgtgctcgg cacgctcaac gaggacctgg cacgcctcgc caccgacgcc tcgttcgcgg     360
cgtcgtgggt ccagtcgtac gtgcagccct tcgccggcgc cgtccgcttc cgctacatca     420
acgccggcaa cgaggtcatc cctggggacg aggcggcgag cgtcctcccg gccatgagga     480
acctccagtc ggcgctgcgc gccgcggggc tcggcgtgcc ggtcacgacg tcgtcgcga     540
cgtcggtgct gggctcctcg tacccgccgt cgcaggcgc gttctccgag ccgcgctgc      600
cgacggtggc gccgatcgtc tccttcctgg cgtcgagcgg gacgcccctg ctggtgaacg     660
tgtacccgta cttcgcctac tccgccgacc cgtcgtcggt gcggctcgac tacgcgctgc     720
tgtcgccgtc gacgtcggcg gccgtgacgg acggcggtgt cacgtacacc aacatgttcg     780
acgccatcct ggacgcggtg tacgcggcgc tggagaaggc gggcggggcag ggcctggagg     840
tggtggtgtc ggagaccggg tggccgtcgg gcggcggcgg ggccggcgcc agcgtggaga     900
acgcggcggc gtacagcaac aacctggtgc gccacgtcgg gcgcggcacg ccgcggcggc     960
ccgggaaggc cgtggagacg tacatcttcg ccatgttcaa cgagaaccag aagcccgagg    1020
gcgtggagca gaacttcggc ctgttccacc cggacatgag cgcggtctac cacgtcgact    1080
tctcggcgtg atcatcttaa tcaggcagcg acggc                              1115
```

<210> SEQ ID NO 11
<211> LENGTH: 1014
<212> TYPE: DNA
<213> ORGANISM: Oryza sativa

<400> SEQUENCE: 11

```
atggatgctg tgttggttac cgccgccatc ttcgggttgc tgctctgcgg ctgctcggtt      60
tcaggagtgg aaggtatcgg tgtgaactat ggcatgatcg gcaacaacct cccgtcgccg     120
gacaaggtca tcgccctgta cagagccagc aacatcaccg acatccgcct cttccacccg     180
gacaccaccg tgctcgccgc gctccgcggc tcgggcctcg gcgtcgtgct cggcacgctc     240
aacgaggacc tggcacgcct cgccaccgac gcctcgttcg cggcgtcgtg ggtccagtcg     300
tacgtgcagc ccttcgccgg cgccgtccgc ttccgctaca tcaacgccgg caacgaggtc     360
atccctgggg acgaggcggc gagcgtcctc ccggccatga ggaacctcca gtcggcgctg     420
cgcgccgcgg ggctcggcgt gccggtcacg acgtcgtcg cgacgtcggt gctgggctcc     480
tcgtacccgc cgtcgcaggg cgcgttctcc gaggccgcgc tgccgacggt ggcgccgatc     540
gtctccttcc tggcgtcgag cgggacgccc ctgctggtga acgtgtaccc gtacttcgcc     600
tactccgcca ccgtcgtc ggtgcggctc gactacgcgc tgctgtcgcc gtcgacgtcg     660
gcggccgtga cggacggcgg tgtcacgtac accaacatgt tcgacgccat cctggacgcg     720
gtgtacgcgg cgctggagaa ggcgggcggg cagggcctgg aggtggtggt gtcggagacc     780
gggtggccgt cgggcggcgg cggggccggc gccagcgtgg agaacgcggc ggcgtacagc     840
aacaacctgg tgcgccacgt cgggcgcggc acgccgcggc ggcccgggaa ggccgtggag     900
acgtacatct tcgccatgtt caacgagaac cagaagcccg agggcgtgga gcagaacttc     960
ggcctgttcc acccggacat gagcgcggtc taccacgtcg acttctcggc gtga         1014
```

<210> SEQ ID NO 12
<211> LENGTH: 337
<212> TYPE: PRT
<213> ORGANISM: Oryza sativa

<400> SEQUENCE: 12

```
Met Asp Ala Val Leu Val Thr Ala Ala Ile Phe Gly Leu Leu Leu Cys
1               5                   10                  15

Gly Cys Ser Val Ser Gly Val Glu Gly Ile Gly Val Asn Tyr Gly Met
            20                  25                  30

Ile Gly Asn Asn Leu Pro Ser Pro Asp Lys Val Ile Ala Leu Tyr Arg
        35                  40                  45

Ala Ser Asn Ile Thr Asp Ile Arg Leu Phe His Pro Asp Thr Thr Val
    50                  55                  60

Leu Ala Ala Leu Arg Gly Ser Gly Leu Gly Val Val Leu Gly Thr Leu
65                  70                  75                  80

Asn Glu Asp Leu Ala Arg Leu Ala Thr Asp Ala Ser Phe Ala Ala Ser
                85                  90                  95

Trp Val Gln Ser Tyr Val Gln Pro Phe Ala Gly Ala Val Arg Phe Arg
            100                 105                 110

Tyr Ile Asn Ala Gly Asn Glu Val Ile Pro Gly Asp Glu Ala Ala Ser
        115                 120                 125

Val Leu Pro Ala Met Arg Asn Leu Gln Ser Ala Leu Arg Ala Ala Gly
    130                 135                 140

Leu Gly Val Pro Val Thr Thr Val Val Ala Thr Ser Val Leu Gly Ser
145                 150                 155                 160

Ser Tyr Pro Pro Ser Gln Gly Ala Phe Ser Glu Ala Ala Leu Pro Thr
                165                 170                 175

Val Ala Pro Ile Val Ser Phe Leu Ala Ser Ser Gly Thr Pro Leu Leu
            180                 185                 190

Val Asn Val Tyr Pro Tyr Phe Ala Tyr Ser Ala Asp Pro Ser Ser Val
        195                 200                 205

Arg Leu Asp Tyr Ala Leu Leu Ser Pro Ser Thr Ser Ala Ala Val Thr
    210                 215                 220

Asp Gly Gly Val Thr Tyr Thr Asn Met Phe Asp Ala Ile Leu Asp Ala
225                 230                 235                 240

Val Tyr Ala Ala Leu Glu Lys Ala Gly Gly Gln Gly Leu Glu Val Val
                245                 250                 255

Val Ser Glu Thr Gly Trp Pro Ser Gly Gly Gly Ala Gly Ala Ser
            260                 265                 270

Val Glu Asn Ala Ala Tyr Ser Asn Asn Leu Val Arg His Val Gly
        275                 280                 285

Arg Gly Thr Pro Arg Arg Pro Gly Lys Ala Val Glu Thr Tyr Ile Phe
    290                 295                 300

Ala Met Phe Asn Glu Asn Gln Lys Pro Glu Gly Val Glu Gln Asn Phe
305                 310                 315                 320

Gly Leu Phe His Pro Asp Met Ser Ala Val Tyr His Val Asp Phe Ser
                325                 330                 335

Ala
```

<210> SEQ ID NO 13
<211> LENGTH: 661
<212> TYPE: DNA
<213> ORGANISM: Oryza sativa

<400> SEQUENCE: 13

```
gattgatccg tggctgctcc gtggggggcg atggcgatgc cgcggtcgcc gggcgcgggc    60
tcgctccggt ttcttggcct cctgaagcag ccggagtcgg ggcccgacgg cgcggcgccg   120
ccgttcgagc tcgacgagag cgacgtggtg tggccggccg cggtgtcgg ggacgacggt   180
tactgctgcc cggcgccgcc acacccggag ggcccaccgc gcgcgccccg ccgcgcccac   240
acggtgccgc agagcttcgg gctgtcgtcg ctgctcgcca acggggggcg cggcggcggc   300
agcgacgacg gcgtcagga tggagtggcc gtgcccgtga gggccgcggc ggcgccgggt   360
ggaggcgccg cggcaccgag gcggtcggca ccggtgaggg tcccgatgtg gccgggcaag   420
ggcgccgccg ccaacaacgt cgtcggcggc gaggagtccg acgacaacga ggacgacgag   480
atggtgccgc cgcacgtggt ggcggcgcgg cggcacgcgc ggtcgtcgtc ggtgctggag   540
ggcgccggga ggacgctcaa ggggcgcgac ctccgccgcg tccgcaacgc cgtgctccgg   600
cagaccggat cctcgacct ctgaagaatc aaagcatcc catcgccatc atcatatctt   660
g                                                                 661
```

<210> SEQ ID NO 14
<211> LENGTH: 594
<212> TYPE: DNA
<213> ORGANISM: Oryza sativa

<400> SEQUENCE: 14

```
atggcgatgc cgcggtcgcc gggcgcgggc tcgctccggt ttcttggcct cctgaagcag    60
ccggagtcgg ggcccgacgg cgcggcgccg ccgttcgagc tcgacgagag cgacgtggtg   120
tggccggccg cggtgtcgg ggacgacggt tactgctgcc cggcgccgcc acacccggag   180
ggcccaccgc gcgcgccccg ccgcgcccac acggtgccgc agagcttcgg gctgtcgtcg   240
ctgctcgcca acggggggcg cggcggcggc agcgacgacg gcgtcagga tggagtggcc   300
gtgcccgtga gggccgcggc ggcgccgggt ggaggcgccg cggcaccgag gcggtcggca   360
ccggtgaggg tcccgatgtg gccgggcaag ggcgccgccg ccaacaacgt cgtcggcggc   420
gaggagtccg acgacaacga ggacgacgag atggtgccgc cgcacgtggt ggcggcgcgg   480
cggcacgcgc ggtcgtcgtc ggtgctggag ggcgccggga ggacgctcaa ggggcgcgac   540
ctccgccgcg tccgcaacgc cgtgctccgg cagaccggat cctcgacct ctga          594
```

<210> SEQ ID NO 15
<211> LENGTH: 197
<212> TYPE: PRT
<213> ORGANISM: Oryza sativa

<400> SEQUENCE: 15

```
Met Ala Met Pro Arg Ser Pro Gly Ala Gly Ser Leu Arg Phe Leu Gly
1               5                   10                  15

Leu Leu Lys Gln Pro Glu Ser Gly Pro Asp Gly Ala Ala Pro Phe
            20                  25                  30

Glu Leu Asp Glu Ser Asp Val Val Trp Pro Ala Gly Val Gly Asp
        35                  40                  45

Asp Gly Tyr Cys Cys Pro Ala Pro His Pro Glu Gly Pro Pro Arg
    50                  55                  60

Ala Pro Arg Arg Ala His Thr Val Pro Gln Ser Phe Gly Leu Ser Ser
65                  70                  75                  80

Leu Leu Ala Asn Gly Gly Arg Gly Gly Gly Ser Asp Asp Gly Arg Gln
```

```
                    85                  90                  95
Asp Gly Val Ala Val Pro Val Arg Ala Ala Ala Pro Gly Gly
            100                 105                 110

Ala Ala Ala Pro Arg Arg Ser Ala Pro Val Arg Val Pro Met Trp Pro
            115                 120                 125

Gly Lys Gly Ala Ala Ala Asn Asn Val Val Gly Glu Glu Ser Asp
        130                 135                 140

Asp Asn Glu Asp Asp Glu Met Val Pro Pro His Val Val Ala Ala Arg
145                 150                 155                 160

Arg His Ala Arg Ser Ser Ser Val Leu Glu Gly Ala Gly Arg Thr Leu
                165                 170                 175

Lys Gly Arg Asp Leu Arg Arg Val Arg Asn Ala Val Leu Arg Gln Thr
        180                 185                 190

Gly Phe Leu Asp Leu
        195

<210> SEQ ID NO 16
<211> LENGTH: 1819
<212> TYPE: DNA
<213> ORGANISM: Oryza sativa

<400> SEQUENCE: 16
cgacgcgaca cggggagcaag cagcgcgcgc gcgctactcc gaaccgaagg cccacgcggc    60
gccatgctgc tgggtgccat gagcggcggc ggcgtcgtcg tcgccgtcgc cgtcgcctac   120
gccgccctgg ccgtggtggc gctgcggatg gcgctgtcgt acaagtcggc gctgtacgcg   180
gtgcggcggc tgtggcggtg ggccgacgag tgggcgcagg cgtaccagta ccacgaggtg   240
ccacgcttcg cgtgcgacgg cggcggcgcc gagaacccgc tgttccgcaa ggcggcgcag   300
tacgtggcgg tgctgccgtc gctcgaggac gccgacgccg cctccgtgct gtcgtccgcg   360
tcgaggacca acggcggctt ctccctgcag cttgggccag ccacaccgc gcgcgacgcc    420 ttcctcggcg cgcgcctcgc gtggacaaac cggggcgacg tgctggttct gcgcgtgcgc   480
cgccatgacc ggacgcgcgt gctgcggccc tacctgcagc acgtcgagtc cgttgccgat   540
gagatggagc tccggcgacg cgagctgcgg ctgttcgcca acaccggcgt ggacgggagc   600
accgggacgc cgaggtgggc gtcggcgccg ttcacccacc cggcgacgct tgacacggtg   660
gccatggacc ccgacctcaa ggctcgcgtc cgcgccgacc tcgagaactt cctcaagggc   720
cgcgcctact accaccgcct cgggcgggtg tggcgccgga gctacctcct ctacggcccg   780
ctgggcaccg gcaagtcgac cttcgcggcg gccatggctc ggttcttggg ctacgacatc   840
tacgacgtcg atctctcccg cgccggcagc gacgacctcc gcgcgctgct cctgcacacc   900 acccgcggt ccctcatcct cgtggaggac ctcgaccggt tcctccaggg cggcggggcc    960
ggggacgcgg aggcgagggc ggcgagggtg ctgagcttca tggacggcgt cgcgtcgtgc  1020
tgtggcgagg agcgggtgat ggtgttcacg atgcgcggcg gcaaggaggg cgtggacgcg  1080
gcggtggtgc ggccggggag gctggacgtg cacatccact tcacgctctg cgacttcgag  1140
gcgttcaagg cgctggccag caactacctc ggcctcaagg accacaagct gtacccgcag  1200
gtggaggaga gcttccatgg cggcgcgcgc ctcagccccg ccgagctcgg cgagatcatg  1260
ctcgccaacc gctcgtcgcc gagccgcgcg ctgcgcaacg tcatcacgaa gctccagcac  1320
gtgtccgggg cggcggcggc gccgcggccg ccgcacaggc ggaacacgag ctggtccggc  1380
gcgggcgggc catgggagga gcaggccgcg cgcgccagcg cggacgcggc ggacggcggc  1440
```

| | |
|---|---|
| gaggaggcga tcacggcgac ggcggcgtgc ggggtgttcg cgaaggacgc gccgatgagg | 1500 |
| gagttcaaga agctgtacgg gctgatcaag atcaggagcc ggaaggaggg ctccagcggg | 1560 |
| ttcatgccct gcacggcgg cgaagcgccg tcgccggcaa acgggcgggg cagcgagcac | 1620 |
| gacaaggagc ggtgattaat taggcgatgg tagtagaccc cgtcaaacaa gaaaaatatt | 1680 |
| tttgatttt tgtccgtgct tttttacttc gtgttaggct agtaggagta ctacgtagtt | 1740 |
| gtagttagtt cacttttaa ttgtggatgg aagaaatcaa acacgaaatg gaggatgata | 1800 |
| atgggattgg gtgatgtac | 1819 |

<210> SEQ ID NO 17
<211> LENGTH: 1572
<212> TYPE: DNA
<213> ORGANISM: Oryza sativa

<400> SEQUENCE: 17

| | |
|---|---|
| atgctgctgg gtgccatgag cggcggcggc gtcgtcgtcg ccgtcgccgt cgcctacgcc | 60 |
| gccctggccg tggtggcgct gcggatggcg ctgtcgtaca agtcgcgct gtacgcggtg | 120 |
| cggcggctgt ggcggtgggc cgacgagtgg gcgcaggcgt accagtacca cgaggtgcca | 180 |
| cgcttcgcgt cgacggcgg cggcgccgag aacccgctgt tccgcaaggc ggcgcagtac | 240 |
| gtggcggtgc tgccgtcgct cgaggacgcc gacgccgcct ccgtgctgtc gtccgcgtcg | 300 |
| aggaccaacg gcggcttctc cctgcagctt gggccaggcc acaccgcgcg cgacgccttc | 360 |
| ctcggcgcgc gcctcgcgtg gacaaaccgg ggcgacgtgc tggttctgcg cgtgcgccgc | 420 |
| catgaccgga cgcgcgtgct gcggccctac ctgcagcacg tcgagtccgt tgccgatgag | 480 |
| atggagctcc ggcgacgcga gctgcggctg ttcgccaaca ccggcgtgga cgggagcacc | 540 |
| gggacgccga ggtgggcgtc ggccgcgttc acccacccgg cgacgcttga cacggtggcc | 600 |
| atggaccccg acctcaaggc tcgcgtccgc gccgacctcg agaacttcct caagggccgc | 660 |
| gcctactacc accgcctcgg gcgggtgtgg cgccggagct acctcctcta cggcccgctg | 720 |
| ggcaccggca gtcgaccctt cgcggcggcc atggctcggt tcttgggcta cgacatctac | 780 |
| gacgtcgatc tctcccgcgc cggcagcgac gacctccgcg cgctgctcct gcacaccacc | 840 |
| ccgcggtccc tcatcctcgt ggaggacctc gaccggttcc tccagggcgg cggggccggg | 900 |
| gacgcggagg cgagggcggc gagggtgctg agcttcatgg acggcgtcgc gtcgtgctgt | 960 |
| ggcgaggagc gggtgatggt gttcacgatg cgcggcggca aggagggcgt ggacgcggcg | 1020 |
| gtggtgcggc cggggaggct ggacgtgcac atccacttca cgctctgcga cttcgaggcg | 1080 |
| ttcaaggcgc tggccagcaa ctacctcggc ctcaaggacc acaagctgta cccgcaggtg | 1140 |
| gaggagagct tccatggcgg cgcgcgcctc agccccgccg agctcggcga gatcatgctc | 1200 |
| gccaaccgct cgtcgccgag ccgcgcgctg cgcaacgtca tcacgaagct ccagcacgtg | 1260 |
| tccggggcgg cggcggcgcc gcggccgccg cacaggcgga acacgagctg gtccggcgcg | 1320 |
| ggcgggccat gggaggagca ggccgcgcgc gccagcgcgg acgcggcgga cggcggcgag | 1380 |
| gaggcgatca cggcgacggc ggcgtgcggg gtgttcgcga aggacgcgcc gatgagggag | 1440 |
| ttcaagaagc tgtacgggct gatcaagatc aggagccgga aggagggctc cagcgggttc | 1500 |
| atgcccttgc acggcggcga agcgccgtcg ccggcaaacg ggcggggcag cgagcacgac | 1560 |
| aaggagcggt ga | 1572 |

<210> SEQ ID NO 18
<211> LENGTH: 523

<212> TYPE: PRT
<213> ORGANISM: Oryza sativa

<400> SEQUENCE: 18

```
Met Leu Leu Gly Ala Met Ser Gly Gly Val Val Ala Val Ala
1               5                   10                  15

Val Ala Tyr Ala Ala Leu Ala Val Val Ala Leu Arg Met Ala Leu Ser
                20                  25                  30

Tyr Lys Ser Ala Leu Tyr Ala Val Arg Arg Leu Trp Arg Trp Ala Asp
            35                  40                  45

Glu Trp Ala Gln Ala Tyr Gln Tyr His Glu Val Pro Arg Phe Ala Cys
        50                  55                  60

Asp Gly Gly Gly Ala Glu Asn Pro Leu Phe Arg Lys Ala Ala Gln Tyr
65                  70                  75                  80

Val Ala Val Leu Pro Ser Leu Glu Asp Ala Asp Ala Ala Ser Val Leu
                85                  90                  95

Ser Ser Ala Ser Arg Thr Asn Gly Gly Phe Ser Leu Gln Leu Gly Pro
            100                 105                 110

Gly His Thr Ala Arg Asp Ala Phe Leu Gly Ala Arg Leu Ala Trp Thr
        115                 120                 125

Asn Arg Gly Asp Val Leu Val Leu Arg Val Arg Arg His Asp Arg Thr
130                 135                 140

Arg Val Leu Arg Pro Tyr Leu Gln His Val Glu Ser Val Ala Asp Glu
                150                 155                 160
145

Met Glu Leu Arg Arg Glu Leu Arg Leu Phe Ala Asn Thr Gly Val
            165                 170                 175

Asp Gly Ser Thr Gly Thr Pro Arg Trp Ala Ser Ala Pro Phe Thr His
        180                 185                 190

Pro Ala Thr Leu Asp Thr Val Ala Met Asp Pro Asp Leu Lys Ala Arg
                195                 200                 205

Val Arg Ala Asp Leu Glu Asn Phe Leu Lys Gly Arg Ala Tyr Tyr His
    210                 215                 220

Arg Leu Gly Arg Val Trp Arg Arg Ser Tyr Leu Leu Tyr Gly Pro Leu
225                 230                 235                 240

Gly Thr Gly Lys Ser Thr Phe Ala Ala Ala Met Ala Arg Phe Leu Gly
                245                 250                 255

Tyr Asp Ile Tyr Asp Val Asp Leu Ser Arg Ala Gly Ser Asp Asp Leu
            260                 265                 270

Arg Ala Leu Leu Leu His Thr Thr Pro Arg Ser Leu Ile Leu Val Glu
        275                 280                 285

Asp Leu Asp Arg Phe Leu Gln Gly Gly Gly Ala Gly Asp Ala Glu Ala
    290                 295                 300

Arg Ala Ala Arg Val Leu Ser Phe Met Asp Gly Val Ala Ser Cys Cys
305                 310                 315                 320

Gly Glu Glu Arg Val Met Val Phe Thr Met Arg Gly Gly Lys Glu Gly
                325                 330                 335

Val Asp Ala Ala Val Val Arg Pro Gly Arg Leu Asp Val His Ile His
            340                 345                 350

Phe Thr Leu Cys Asp Phe Glu Ala Phe Lys Ala Leu Ala Ser Asn Tyr
        355                 360                 365

Leu Gly Leu Lys Asp His Lys Leu Tyr Pro Gln Val Glu Glu Ser Phe
    370                 375                 380

His Gly Gly Ala Arg Leu Ser Pro Ala Glu Leu Gly Glu Ile Met Leu
385                 390                 395                 400
```

Ala Asn Arg Ser Ser Pro Ser Arg Ala Leu Arg Asn Val Ile Thr Lys
            405                 410                 415

Leu Gln His Val Ser Gly Ala Ala Ala Ala Pro Arg Pro His Arg
        420                 425                 430

Arg Asn Thr Ser Trp Ser Gly Ala Gly Gly Pro Trp Glu Glu Gln Ala
        435                 440                 445

Ala Arg Ala Ser Ala Asp Ala Ala Asp Gly Gly Glu Glu Ala Ile Thr
450                 455                 460

Ala Thr Ala Ala Cys Gly Val Phe Ala Lys Asp Ala Pro Met Arg Glu
465                 470                 475                 480

Phe Lys Lys Leu Tyr Gly Leu Ile Lys Ile Arg Ser Arg Lys Glu Gly
            485                 490                 495

Ser Ser Gly Phe Met Pro Leu His Gly Gly Glu Ala Pro Ser Pro Ala
                500                 505                 510

Asn Gly Arg Gly Ser Glu His Asp Lys Glu Arg
            515                 520

<210> SEQ ID NO 19
<211> LENGTH: 869
<212> TYPE: DNA
<213> ORGANISM: Oryza sativa

<400> SEQUENCE: 19

```
cgagagctaa gcgaggaagg atgcgtgggg cgtcggcatt ggcatctctc gtcgccgcgg      60
cggcggtggc gctgctcctc ctcatcgacg gctgcggcgg cgccatgtac aaggttggcg     120
acctcgacgc ctggggcatc ccgccgccgt ccaagcccga cgtctactcg cgctgggcca     180
aatccatcca cttcgcgctc ggcgactcca tctgtaagca ctggatcatc gcgattagag     240
gcctcgtctt tttcttatgt ttgtacttat caaccgaaat ttaaattttt caacttcaga     300
tttaaagctg attttaaaat ttttttcatc gaaatttatt tttcagactt tgtttttagc     360
tgattataaa aattttactc ttaaattatt tttcgtttgt aaatacgccg taactcatct     420
tcttcactgg gtatgattca cgcagggttt ctgtacccgc cgagccagga ctcggtggtg     480
caggtgacgc cggtggcgtt cgccgcctgc caggcgtcgg accggtgct gaagctcgac      540
gacggcaact ccgtcttcaa cctcaccacg cccggccgcg tctactacat cagcgccgcg     600
ctgggacact gccggaaggg ccagaggctg ccgtcgacg tgcccatggc aacggcacc      660
tacctgccgc ccaccgccaa cgacctcgcc gccttcgcgc cgatgccggc cgaggcgccg     720
gcggggttcg agtcggcggc gctcggcccc gccggagcgc gacagtcggc ggcgccccga     780
gccgccgccg ccggcggagc tggatccgtc cttcttgctg ctcttgcctt cgccgtcttc     840
ttgctgtgag agcatcttgt tgattgtgg                                        869
```

<210> SEQ ID NO 20
<211> LENGTH: 597
<212> TYPE: DNA
<213> ORGANISM: Oryza sativa

<400> SEQUENCE: 20

```
atgcgtgggg cgtcggcatt ggcatctctc gtcgccgcgg cggcggtggc gctgctcctc      60
ctcatcgacg gctgcggcgg cgccatgtac aaggttggcg acctcgacgc ctggggcatc     120
ccgccgccgt ccaagcccga cgtctactcg cgctgggcca aatccatcca cttcgcgctc     180
ggcgactcca tctggtttct gtacccgccg agccaggact cggtggtgca ggtgacgccg     240
```

```
gtggcgttcg ccgcctgcca ggcgtcggac ccggtgctga agctcgacga cggcaactcc    300
gtcttcaacc tcaccacgcc cggccgcgtc tactacatca cgccgcgct gggacactgc     360 cggaagggcc agaggctggc cgtcgacgtg cccatggcca acggcaccta cctgccgccc    420
accgccaacg acctcgccgc cttcgcgccg atgccggccg aggcgccggc ggggttcgag    480
tcggcggcgc tcggccccgc cggagcgcga cagtcggcgg cgccccgagc cgccgccgcc    540
ggcggagctg gatccgtcct tcttgctgct cttgccttcg ccgtcttctt gctgtga       597
```

<210> SEQ ID NO 21
<211> LENGTH: 198
<212> TYPE: PRT
<213> ORGANISM: Oryza sativa

<400> SEQUENCE: 21

```
Met Arg Gly Ala Ser Ala Leu Ala Ser Leu Val Ala Ala Ala Val
1               5                   10                  15

Ala Leu Leu Leu Leu Ile Asp Gly Cys Gly Gly Ala Met Tyr Lys Val
            20                  25                  30

Gly Asp Leu Asp Ala Trp Gly Ile Pro Pro Ser Lys Pro Asp Val
        35                  40                  45

Tyr Ser Arg Trp Ala Lys Ser Ile His Phe Ala Leu Gly Asp Ser Ile
    50                  55                  60

Trp Phe Leu Tyr Pro Pro Ser Gln Asp Ser Val Gln Val Thr Pro
65                  70                  75                  80

Val Ala Phe Ala Ala Cys Gln Ala Ser Asp Pro Val Leu Lys Leu Asp
                85                  90                  95

Asp Gly Asn Ser Val Phe Asn Leu Thr Thr Pro Gly Arg Val Tyr Tyr
            100                 105                 110

Ile Ser Ala Ala Leu Gly His Cys Arg Lys Gly Gln Arg Leu Ala Val
            115                 120                 125

Asp Val Pro Met Ala Asn Gly Thr Tyr Leu Pro Pro Thr Ala Asn Asp
            130                 135                 140

Leu Ala Ala Phe Ala Pro Met Pro Ala Glu Pro Ala Gly Phe Glu
145                 150                 155                 160

Ser Ala Ala Leu Gly Pro Ala Gly Ala Arg Gln Ser Ala Ala Pro Arg
                165                 170                 175

Ala Ala Ala Ala Gly Gly Ala Gly Ser Val Leu Leu Ala Ala Leu Ala
            180                 185                 190

Phe Ala Val Phe Leu Leu
        195
```

<210> SEQ ID NO 22
<211> LENGTH: 26
<212> TYPE: DNA
<213> ORGANISM: Artificial Sequence
<220> FEATURE:
<223> OTHER INFORMATION: Forward primer for cloning cDNA of OsBCS1-2
      gene

<400> SEQUENCE: 22
gttttcagag acgtaccaga gccaac                                          26

<210> SEQ ID NO 23
<211> LENGTH: 26
<212> TYPE: DNA
<213> ORGANISM: Artificial Sequence
<220> FEATURE:
<223> OTHER INFORMATION: Reverse primer for cloning cDNA of OsBCS1-2

```
                             gene

<400> SEQUENCE: 23
gcacactgtt taagcatcat tatttg                                        26

<210> SEQ ID NO 24
<211> LENGTH: 30
<212> TYPE: DNA
<213> ORGANISM: Artificial Sequence
<220> FEATURE:
<223> OTHER INFORMATION: Forward primer for cloning gDNA of OsDnaJ7
      gene

<400> SEQUENCE: 24
ctcctccaaa aatattccca ccccaacctc                                    30

<210> SEQ ID NO 25
<211> LENGTH: 26
<212> TYPE: DNA
<213> ORGANISM: Artificial Sequence
<220> FEATURE:
<223> OTHER INFORMATION: Reverse primer for cloning gDNA of OsDnaJ7
      gene

<400> SEQUENCE: 25
gaattggtaa ggctagctgt ggttac                                        26

<210> SEQ ID NO 26
<211> LENGTH: 29
<212> TYPE: DNA
<213> ORGANISM: Artificial Sequence
<220> FEATURE:
<223> OTHER INFORMATION: Forward primer for cloning gDNA of OsLNTP10
      gene

<400> SEQUENCE: 26
caactgagca agaactgaag aaaatagag                                     29

<210> SEQ ID NO 27
<211> LENGTH: 27
<212> TYPE: DNA
<213> ORGANISM: Artificial Sequence
<220> FEATURE:
<223> OTHER INFORMATION: Reverse primer for cloning gDNA of OsLNTP10
      gene

<400> SEQUENCE: 27
gatgatgatg atgttgctgt tcgattg                                       27

<210> SEQ ID NO 28
<211> LENGTH: 26
<212> TYPE: DNA
<213> ORGANISM: Artificial Sequence
<220> FEATURE:
<223> OTHER INFORMATION: Forward primer for cloning cDNA of OsGH17.2
      gene

<400> SEQUENCE: 28
gaggagtcgg aaaggagata cagttc                                        26

<210> SEQ ID NO 29
<211> LENGTH: 23
<212> TYPE: DNA
<213> ORGANISM: Artificial Sequence
<220> FEATURE:
<223> OTHER INFORMATION: Reverse primer for cloning cDNA of OsGH17.2
      gene
```

<400> SEQUENCE: 29
gccgtcgctg cctgattaag atg                                   23

<210> SEQ ID NO 30
<211> LENGTH: 23
<212> TYPE: DNA
<213> ORGANISM: Artificial Sequence
<220> FEATURE:
<223> OTHER INFORMATION: Forward primer for cloning gDNA of OsDUF6 gene

<400> SEQUENCE: 30
gattgatccg tggctgctcc gtg                                   23

<210> SEQ ID NO 31
<211> LENGTH: 27
<212> TYPE: DNA
<213> ORGANISM: Artificial Sequence
<220> FEATURE:
<223> OTHER INFORMATION: Reverse primer for cloning gDNA of OsDUF6 gene

<400> SEQUENCE: 31
caagatatga tgatggcgat gggatgc                               27

<210> SEQ ID NO 32
<211> LENGTH: 23
<212> TYPE: DNA
<213> ORGANISM: Artificial Sequence
<220> FEATURE:
<223> OTHER INFORMATION: Forward primer for cloning cDNA of OsATAP1 gene

<400> SEQUENCE: 32
cgacgcgaca cgggagcaag cag                                   23

<210> SEQ ID NO 33
<211> LENGTH: 30
<212> TYPE: DNA
<213> ORGANISM: Artificial Sequence
<220> FEATURE:
<223> OTHER INFORMATION: Reverse primer for cloning cDNA of OsATAP1 gene

<400> SEQUENCE: 33
gtacatcacc caatcccatt atcatcctcc                            30

<210> SEQ ID NO 34
<211> LENGTH: 24
<212> TYPE: DNA
<213> ORGANISM: Artificial Sequence
<220> FEATURE:
<223> OTHER INFORMATION: Forward primer for cloning gDNA of OsPCL1 gene

<400> SEQUENCE: 34
cgagagctaa gcgaggaagg atgc                                  24

<210> SEQ ID NO 35
<211> LENGTH: 26
<212> TYPE: DNA
<213> ORGANISM: Artificial Sequence
<220> FEATURE:
<223> OTHER INFORMATION: Reverse primer for cloning gDNA of OsPCL1 gene

<400> SEQUENCE: 35
ccacaatcaa caagatgctc tcacag                                26

<210> SEQ ID NO 36

```
<211> LENGTH: 21
<212> TYPE: DNA
<213> ORGANISM: Artificial Sequence
<220> FEATURE:
<223> OTHER INFORMATION: Forward primer for real-time PCR analysis of
      OsBCS1-2 gene

<400> SEQUENCE: 36
ggcaaagctg aaaatgtgga g                                              21

<210> SEQ ID NO 37
<211> LENGTH: 21
<212> TYPE: DNA
<213> ORGANISM: Artificial Sequence
<220> FEATURE:
<223> OTHER INFORMATION: Reverse primer for real-time PCR analysis of
      OsBCS1-2 gene

<400> SEQUENCE: 37
gggatcttga ttctctggga c                                              21

<210> SEQ ID NO 38
<211> LENGTH: 18
<212> TYPE: DNA
<213> ORGANISM: Artificial Sequence
<220> FEATURE:
<223> OTHER INFORMATION: Forward primer for real-time PCR analysis of
      OsDnaJ7 gene

<400> SEQUENCE: 38
agatgggaag cgtcgttg                                                  18

<210> SEQ ID NO 39
<211> LENGTH: 22
<212> TYPE: DNA
<213> ORGANISM: Artificial Sequence
<220> FEATURE:
<223> OTHER INFORMATION: Reverse primer for real-time PCR analysis of
      OsDnaJ7 gene

<400> SEQUENCE: 39
cttcttcatg tcctcgttct cc                                             22

<210> SEQ ID NO 40
<211> LENGTH: 20
<212> TYPE: DNA
<213> ORGANISM: Artificial Sequence
<220> FEATURE:
<223> OTHER INFORMATION: Forward primer for real-time PCR analysis of
      OsLNTP10 gene

<400> SEQUENCE: 40
cagtggcaag gagaagaggc                                                20

<210> SEQ ID NO 41
<211> LENGTH: 22
<212> TYPE: DNA
<213> ORGANISM: Artificial Sequence
<220> FEATURE:
<223> OTHER INFORMATION: Reverse primer for real-time PCR analysis of
      OsLNTP10 gene

<400> SEQUENCE: 41
gttgtagctg gcttctctcc tg                                             22

<210> SEQ ID NO 42
<211> LENGTH: 20
```

```
<212> TYPE: DNA
<213> ORGANISM: Artificial Sequence
<220> FEATURE:
<223> OTHER INFORMATION: Forward primer for real-time PCR analysis of
      OsGH17.2 gene

<400> SEQUENCE: 42
catcttcgcc atgttcaacg                                                20

<210> SEQ ID NO 43
<211> LENGTH: 18
<212> TYPE: DNA
<213> ORGANISM: Artificial Sequence
<220> FEATURE:
<223> OTHER INFORMATION: Reverse primer for real-time PCR analysis of
      OsGH17.2 gene

<400> SEQUENCE: 43
catgtccggg tggaacag                                                  18

<210> SEQ ID NO 44
<211> LENGTH: 19
<212> TYPE: DNA
<213> ORGANISM: Artificial Sequence
<220> FEATURE:
<223> OTHER INFORMATION: Forward primer for real-time PCR analysis of
      OsDUF6 gene

<400> SEQUENCE: 44
cacggtgccg cagagcttc                                                 19

<210> SEQ ID NO 45
<211> LENGTH: 20
<212> TYPE: DNA
<213> ORGANISM: Artificial Sequence
<220> FEATURE:
<223> OTHER INFORMATION: Reverse primer for real-time PCR analysis of
      OsDUF6 gene

<400> SEQUENCE: 45
ggcaccatct cgtcgtcctc                                                20

<210> SEQ ID NO 46
<211> LENGTH: 20
<212> TYPE: DNA
<213> ORGANISM: Artificial Sequence
<220> FEATURE:
<223> OTHER INFORMATION: Forward primer for real-time PCR analysis of
      OsATAP1 gene

<400> SEQUENCE: 46
tcaaggacca caagctgtac                                                20

<210> SEQ ID NO 47
<211> LENGTH: 19
<212> TYPE: DNA
<213> ORGANISM: Artificial Sequence
<220> FEATURE:
<223> OTHER INFORMATION: Reverse primer for real-time PCR analysis of
      OsATAP1 gene

<400> SEQUENCE: 47
ggttggcgag catgatctc                                                 19

<210> SEQ ID NO 48
<211> LENGTH: 18
<212> TYPE: DNA
```

```
<213> ORGANISM: Artificial Sequence
<220> FEATURE:
<223> OTHER INFORMATION: Forward primer for real-time PCR analysis of
      OsPCL1 gene

<400> SEQUENCE: 48
gtttctgtac cgccgag                                                    18

<210> SEQ ID NO 49
<211> LENGTH: 20
<212> TYPE: DNA
<213> ORGANISM: Artificial Sequence
<220> FEATURE:
<223> OTHER INFORMATION: Reverse primer for real-time PCR analysis of
      OsPCL1 gene

<400> SEQUENCE: 49
tgaggttgaa gacggagttg                                                 20

<210> SEQ ID NO 50
<211> LENGTH: 199
<212> TYPE: DNA
<213> ORGANISM: Artificial Sequence
<220> FEATURE:
<223> OTHER INFORMATION: The nucleotide sequence of intron used for
      constructing RNAi construct

<400> SEQUENCE: 50
gtacggaccg tactactcta ttcgtttcaa tatatttatt tgtttcagct gactgcaaga     60
ttcaaaaatt tctttattat tttaaatttt gtgtcactca aaaccagata aacaatttga    120
tatagaggca ctatatatat acatattctc gattatatat gtaaatgagt taaccttttt    180
ttccacttaa attatatag                                                 199

<210> SEQ ID NO 51
<211> LENGTH: 177
<212> TYPE: DNA
<213> ORGANISM: Oryza sativa

<400> SEQUENCE: 51
cattggcatc tctcgtcgcc gcggcggcgg tggcgctgct cctcctcatc gacggctgcg     60
gcggcgccat gtacaaggtt ggcgacctcg acgcctgggg catcccgccg ccgtccaagc    120
ccgacgtcta ctcgcgctgg gccaaatcca tccacttcgc gctcggcgac tccatct      177

<210> SEQ ID NO 52
<211> LENGTH: 28
<212> TYPE: DNA
<213> ORGANISM: Artificial Sequence
<220> FEATURE:
<223> OTHER INFORMATION: Forward primer for cloning sense strand cDNA of
      OsPCL1 gene for constructing RNAi construct

<400> SEQUENCE: 52
ctgctgaggc attggcatct ctcgtcgc                                        28

<210> SEQ ID NO 53
<211> LENGTH: 28
<212> TYPE: DNA
<213> ORGANISM: Artificial Sequence
<220> FEATURE:
<223> OTHER INFORMATION: Reverse primer for cloning sense strand cDNA of
      OsPCL1 gene for constructing RNAi construct

<400> SEQUENCE: 53
```

```
gcttgctgag gagatggagt cgccgagc                                              28

<210> SEQ ID NO 54
<211> LENGTH: 28
<212> TYPE: DNA
<213> ORGANISM: Artificial Sequence
<220> FEATURE:
<223> OTHER INFORMATION: Forward primer for cloning antisense strand
      cDNA of OsPCL1 gene for constructing RNAi construct

<400> SEQUENCE: 54
ccgctgaggc attggcatct ctcgtcgc                                              28

<210> SEQ ID NO 55
<211> LENGTH: 28
<212> TYPE: DNA
<213> ORGANISM: Artificial Sequence
<220> FEATURE:
<223> OTHER INFORMATION: Reverse primer for cloning antisense strand
      cDNA of OsPCL1 gene for constructing RNAi construct

<400> SEQUENCE: 55
gcctgctgag gagatggagt cgccgagc                                              28

<210> SEQ ID NO 56
<211> LENGTH: 20
<212> TYPE: DNA
<213> ORGANISM: Artificial Sequence
<220> FEATURE:
<223> OTHER INFORMATION: Nucleotide sequence of gRNA1 for target site
      sequence for OsBCS1-2 gene

<400> SEQUENCE: 56
acctgaactc ggagccctca                                                       20

<210> SEQ ID NO 57
<211> LENGTH: 20
<212> TYPE: DNA
<213> ORGANISM: Artificial Sequence
<220> FEATURE:
<223> OTHER INFORMATION: Nucleotide sequence of gRNA3 for target site
      sequence for OsBCS1-2 gene

<400> SEQUENCE: 57
atctgggcta ctcaacttcg                                                       20

<210> SEQ ID NO 58
<211> LENGTH: 20
<212> TYPE: DNA
<213> ORGANISM: Artificial Sequence
<220> FEATURE:
<223> OTHER INFORMATION: Nucleotide sequence of gRNA3 for target site
      sequence for OsDnaJ7 gene

<400> SEQUENCE: 58
agcgtcgttg cgagattacc                                                       20

<210> SEQ ID NO 59
<211> LENGTH: 20
<212> TYPE: DNA
<213> ORGANISM: Artificial Sequence
<220> FEATURE:
<223> OTHER INFORMATION: Nucleotide sequence of gRNA4 for target site
      sequence for OsDnaJ7 gene

<400> SEQUENCE: 59
tcgcgatctc ccggttgctc                                                       20
```

<210> SEQ ID NO 60
<211> LENGTH: 20
<212> TYPE: DNA
<213> ORGANISM: Artificial Sequence
<220> FEATURE:
<223> OTHER INFORMATION: Nucleotide sequence of gRNA9 for target site sequence for OsLNTP10 gene

<400> SEQUENCE: 60
taccagcagt acaagagcag                                         20

<210> SEQ ID NO 61
<211> LENGTH: 20
<212> TYPE: DNA
<213> ORGANISM: Artificial Sequence
<220> FEATURE:
<223> OTHER INFORMATION: Nucleotide sequence of gRNA6 for target site sequence for OsLNTP10 gene

<400> SEQUENCE: 61
caaacctccc ggcccagaag                                         20

<210> SEQ ID NO 62
<211> LENGTH: 20
<212> TYPE: DNA
<213> ORGANISM: Artificial Sequence
<220> FEATURE:
<223> OTHER INFORMATION: Nucleotide sequence of gRNA8 for target site sequence for OsLNTP10 gene

<400> SEQUENCE: 62
gcaggttcta gtttagtgtg                                         20

<210> SEQ ID NO 63
<211> LENGTH: 20
<212> TYPE: DNA
<213> ORGANISM: Artificial Sequence
<220> FEATURE:
<223> OTHER INFORMATION: Nucleotide sequence of gRNA10 for target site sequence for OsLNTP10 gene

<400> SEQUENCE: 63
tgccgctgct cttgtactgc                                         20

<210> SEQ ID NO 64
<211> LENGTH: 20
<212> TYPE: DNA
<213> ORGANISM: Artificial Sequence
<220> FEATURE:
<223> OTHER INFORMATION: Nucleotide sequence of gRNA1 for target site sequence for OsGH17.2 gene

<400> SEQUENCE: 64
tcggcgtgat catcttaatc                                         20

<210> SEQ ID NO 65
<211> LENGTH: 20
<212> TYPE: DNA
<213> ORGANISM: Artificial Sequence
<220> FEATURE:
<223> OTHER INFORMATION: Nucleotide sequence of gRNA3 for target site sequence for OsDUF6 gene

<400> SEQUENCE: 65
ggtcgaggaa tccggtctgc                                         20

<210> SEQ ID NO 66
<211> LENGTH: 20
<212> TYPE: DNA
<213> ORGANISM: Artificial Sequence
<220> FEATURE:
<223> OTHER INFORMATION: Nucleotide sequence of gRNA4 for target site
      sequence for OsDUF6 gene

<400> SEQUENCE: 66
aaccggagcg agcccgcgcc                                                   20

<210> SEQ ID NO 67
<211> LENGTH: 1934
<212> TYPE: DNA
<213> ORGANISM: Zea mays

<400> SEQUENCE: 67
cagtgcagcg tgacccggtc gtgcccctct ctagagataa tgagcattgc atgtctaagt       60
tataaaaaat taccacatat ttttttttgtc acacttgttt gaagtgcagt ttatctatct     120
ttatacatat atttaaactt tactctacga ataatataat ctatagtact acaataatat     180
cagtgtttta gagaatcata taaatgaaca gttagacatg gtctaaagga caattgagta     240
ttttgacaac aggactctac agttttatct ttttagtgtg catgtgttct cctttttttt     300
tgcaaatagc ttcacctata taatacttca tccatttttat tagtacatcc atttagggtt     360
tagggttaat ggttttttata gactaatttt tttagtacat ctattttatt ctattttagc     420
ctctaaatta agaaaactaa aactctattt tagttttttt atttaataat ttagatataa     480
aatagaataa aataaagtga ctaaaaatta aacaaatacc ctttaagaaa ttaaaaaaac     540
taaggaaaca tttttcttgt ttcgagtaga taatgccagc ctgttaaacg ccgtcgacga     600
gtctaacgga caccaaccag cgaaccagca gcgtcgcgtc gggccaagcg aagcagacgg     660
cacggcatct ctgtcgctgc ctctggaccc ctctcgagag ttccgctcca ccgttggact     720
tgctccgctg tcggcatcca gaaattgcgt ggcggagcgg cagacgtgag ccggcacggc     780
aggcggcctc ctcctcctct cacggcaccg gcagctacgg gggattcctt tcccaccgct     840
ccttcgcttt cccttcctcg cccgccgtaa taaatagaca cccccctccac accctctttc     900 cccaacctcg tgttgttcgg agcgcacaca cacacaacca gatctccccc aaatccaccc     960
gtcggcacct ccgcttcaag gtacgccgct cgtcctcccc ccccccctc tctaccttct    1020 ctagatcggc gttccggtcc atggttaggg cccggtagtt ctacttctgt tcatgttgt    1080 gttagatccg tgtttgtgtt agatccgtgc tgctagcgtt cgtacacgga tgcgacctgt    1140
acgtcagaca cgttctgatt gctaacttgc cagtgtttct cttggggaat cctgggatgg    1200
ctctagccgt tccgcagacg ggatcgattt catgattttt tttgtttcgt tgcatagggt    1260
ttggtttgcc ctttttccttt atttcaatat atgccgtgca cttgtttgtc gggtcatctt    1320
ttcatgcttt tttttgtctt ggttgtgatg atgtggtctg gttgggcggt cgttctagat    1380
cggagtagaa ttctgtttca aactacctgg tggatttatt aattttggat ctgtatgtgt    1440
gtgccataca tattcatagt tacgaattga agatgatgga tggaaaatatc gatctaggat    1500 aggtatacat gttgatgcgg gttttactga tgcatataca gagatgcttt ttgttcgctt    1560
ggttgtgatg atgtggtgtg gttgggcggt cgttcattcg ttctagatcg gagtagaata    1620
ctgtttcaaa ctacctggtg tatttattaa ttttggaact gtatgtgtgt gtcatacatc    1680
ttcatagtta cgagtttaag atggatggaa atatcgatct aggataggta tacatgttga    1740

```
tgtgggtttt actgatgcat atacatgatg gcatatgcag catctattca tatgctctaa    1800
ccttgagtac ctatctatta taataaacaa gtatgtttta taattatttt gatcttgata    1860
tacttggatg atggcatatg cagcagctat atgtggattt ttttagccct gccttcatac    1920
gctatttatt tgct                                                      1934

<210> SEQ ID NO 68
<211> LENGTH: 4206
<212> TYPE: DNA
<213> ORGANISM: Artificial Sequence
<220> FEATURE:
<223> OTHER INFORMATION: The nucleotide sequence of nuclear localization
      sequence and Cas9 gene

<400> SEQUENCE: 68 atggcccta agaagaagag aaaggtcggt attcacggcg ttcctgcggc gatggacaag      60
aagtatagta ttggtctgga cattgggacg aattccgttg gctgggccgt gatcaccgat     120
gagtacaagg tccttccaa gaagtttaag gttctgggga acaccgatcg gcacagcatc     180
aagaagaatc tcattggagc cctcctgttc gactcaggcg agaccgccga agcaacaagg     240
ctcaagagaa ccgcaaggag acggtataca agaaggaaga ataggatctg ctacctgcag     300
gagattttca gcaacgaaat ggcgaaggtg gacgattcgt tctttcatag attggaggag     360
agtttcctcg tcgaggaaga taagaagcac gagaggcatc ctatctttgg caacattgtc     420
gacgaggttg cctatcacga aaagtacccc acaatctatc atctgcggaa gaagcttgtg     480
gactcgactg ataaggcgga ccttagattg atctacctcg ctctggcaca catgattaag     540
ttcaggggcc attttctgat cgaggggat cttaacccgg acaatagcga tgtggacaag     600
ttgttcatcc agctcgtcca aacctacaat cagctctttg aggaaaaccc aattaatgct     660
tcaggcgtcg acgccaaggc gatcctgtct gcacgccttt caaagtctcg ccggcttgag     720
aacttgatcg ctcaactccc gggcgaaaag aagaacggct tgttcgggaa tctcattgca     780
ctttcgttgg ggctcacacc aaacttcaag agtaattttg atctcgctga ggacgcaaag     840
ctgcagcttt ccaaggacac ttatgacgat gacctggata acctttggc ccaaatcggc     900 gatcagtacg cggacttgtt cctcgccgcg aagaatttgt cggacgcgat cctcctgagt     960
gatattctcc gcgtgaacac cgagattaca aaggccccgc tctcggcgag tatgatcaag    1020
cgctatgacg agcaccatca ggatctgacc cttttgaagg ctttggtccg gcagcaactc    1080
ccagagaagt acaaggaaat cttctttgat caatccaaga acggctacgc tggttatatt    1140
gacggcgggg catcgcagga ggaattctac aagtttatca agccaattct ggagaagatg    1200
gatggcacag aggaactcct ggtgaagctc aatagggagg accttttgcg gaagcaaaga    1260
actttcgata acggcagcat ccctcaccag attcatctcg gggagctgca cgccatcctg    1320
agaaggcagg aagacttcta ccccttctct aaggataacc gggagaagat cgaaaagatt    1380
ctgacgttca gaattccgta ctatgtcgga ccactcgccc ggggtaattc cagatttgcg    1440
tggatgacca gaaagagcga ggaaaccatc acaccttgga acttcgagga gtggtcgat     1500 aagggcgctt ccgcacagag cttcattgag cgcatgacaa attttgacaa gaacctgcct    1560
aatgagaagg tccttcccaa gcattccctc tgtacgagt atttcactgt ttataacgaa    1620
ctcacgaagg tgaagtatgt gaccgaggga atgcgcaagc ccgccttcct gagcggcgag    1680
caaaagaagg cgatcgtgga ccttttgttt aagaccaatc ggaaggtcac agttaagcag    1740
ctcaaggagg actacttcaa gaagattgaa tgcttcgatt ccgttgagat cagcggcgtg    1800
```

```
gaagacaggt ttaacgcgtc actggggact taccacgatc tcctgaagat cattaaggat    1860
aaggacttct tggacaacga ggaaaatgag gatatcctcg aagacattgt cctgactctt    1920
acgttgtttg aggataggga aatgatcgag gaacgcttga agacgtatgc ccatctcttc    1980
gatgacaagg ttatgaagca gctcaagaga agaagataca ccggatgggg aaggctgtcc    2040
cgcaagctta tcaatggcat tagagacaag caatcaggga agacaatcct tgactttttg    2100
aagtctgatg gcttcgcgaa caggaatttt atgcagctga ttcacgatga ctcacttact    2160
ttcaaggagg atatccagaa ggctcaagtg tcgggacaag gtgacagtct gcacgagcat    2220
atcgccaacc ttgcgggatc tcctgcaatc aagaagggta ttctgcagac agtcaaggtt    2280
gtggatgagc ttgtgaaggt catgggacgg cataagcccg agaacatcgt tattgagatg    2340
gccagagaaa atcagaccac acaaaagggt cagaagaact cgagggagcg catgaagcgc    2400
atcgaggaag gcattaagga gctggggagt cagatcctta aggagcaccc ggtggaaaac    2460
acgcagttgc aaaatgagaa gctctatctg tactatctgc aaaatggcag ggatatgtat    2520
gtggaccagg agttggatat taaccgcctc tcggattacg acgtcgatca tatcgttcct    2580
cagtccttcc ttaaggatga cagcattgac aataaggttc tcaccaggtc gacaagaac     2640 cgcgggaagt ccgataatgt gcccagcgag gaagtcgtta agaagatgaa gaactactgg    2700
aggcaacttt tgaatgccaa gttgatcaca cagaggaagt ttgataacct cactaaggcc    2760
gagcgcggag gtctcagcga actggacaag gcgggcttca ttaagcggca actggttgag    2820
actagacaga tcacgaagca cgtggcgcag attctcgatt cacgcatgaa cacgaagtac    2880
gatgagaatg acaagctgat ccgggaagtg aaggtcatca ccttgaagtc aaagctcgtt    2940
tctgacttca ggaaggattt ccaattttat aaggtgcgcg agatcaacaa ttatcaccat    3000
gctcatgacg catacctcaa cgctgtggtc ggaacagcat tgattaagaa gtacccgaag    3060
ctcgagtccg aattcgtgta cggtgactat aaggtttacg atgtgcgcaa gatgatcgcc    3120
aagtcagagc aggaaattgg caaggccact gcgaagtatt tcttttactc taacattatg    3180
aatttctttt agactgagat cacgctggct aatggcgaaa tccggaagag accacttatt    3240
gagaccaacg gcgagacagg ggaaatcgtg tgggacaagg ggagggattt cgccacagtc    3300
cgcaaggttc tctctatgcc tcaagtgaat attgtcaaga agactgaagt ccagacgggc    3360
gggttctcaa aggaatctat tctgcccaag cggaactcgg ataagcttat cgccagaaag    3420
aaggactggg acccgaagaa gtatggaggt ttcgactcac caacggtggc ttactctgtc    3480
ctggttgtgg caaaggtgga gaagggaaag tcaaagaagc tcaagtctgt caaggagctc    3540
ctgggtatca ccattatgga gaggtccagc ttcgaaaaga atccgatcga ttttctcgag    3600
gcgaagggat ataaggaagt gaagaaggac ctgatcatta agcttccaaa gtacagtctt    3660
ttcgagttgg aaaacggcag gaagcgcatg ttggcttccg caggagagct ccagaagggt    3720
aacgagcttg ctttgccgtc caagtatgtg aacttcctct atctggcatc ccactacgag    3780
aagctcaagg gcagcccaga ggataacgaa cagaagcaac tgtttgtgga gcaacacaag    3840
cattatcttg acgagatcat tgaacagatt tcggagttca gtaagcgcgt catcctcgcc    3900
gacgcgaatt tggataaggt tctctcagcc tacaacaagc accgggacaa gcctatcaga    3960
gagcaggcgg aaaatatcat tcatctcttc accctgacaa accttggggc tcccgctgca    4020
ttcaagtatt ttgacactac gattgatcgg aagagatcaa cttctacgaa ggaggtgctg    4080
gatgcaaccc ttatccacca atcgattact ggcctctacg agacgcggat cgacttgagt    4140
cagctcgggg gggataagag accagcggca accaagaagg caggacaagc gaagaagaag    4200
```

-continued

| | |
|---|---|
| aagtag | 4206 |

<210> SEQ ID NO 69
<211> LENGTH: 367
<212> TYPE: DNA
<213> ORGANISM: Cauliflower mosaic virus

<400> SEQUENCE: 69

| | |
|---|---|
| cggtacgctg aaatcaccag tctctctcta caaatctatc tctctctatt ttctccataa | 60 |
| ataatgtgtg agtagtttcc cgataaggga aattagggtt cttataggt ttcgctcatg | 120 |
| tgttgagcat ataagaaacc cttagtatgt atttgtattt gtaaatact tctatcaata | 180 |
| aaatttctaa ttcctaaaac caaaatccag tactaaaatc cagatctcct aaagtccta | 240 |
| tagatctttg tcgtgaatat aaaccagaca cgagacgact aaacctggag cccagacgcc | 300 |
| gttcgaagct agaagtaccg cttaggcagg aggccgttag ggaaaagatg ctaaggcagg | 360 |
| gttggtt | 367 |

<210> SEQ ID NO 70
<211> LENGTH: 742
<212> TYPE: DNA
<213> ORGANISM: Oryza sativa

<400> SEQUENCE: 70

| | |
|---|---|
| ctcattagcg gtatgcatgt tggtagaagt cggagatgta ataatttc attatataaa | 60 |
| aaaggtactt cgagaaaaat aaatgcatac gaattaattc ttttatgtt ttttaaacca | 120 |
| agtatataga atttattgat ggttaaaatt tcaaaaatat gacgagagaa aggttaaacg | 180 |
| tacggcatat acttctgaac agagagggaa tatgggtttt ttgttgctcc caacaattct | 240 |
| taagcacgta aaggaaaaaa gcacattatc cacattgtac ttccagagat atgtacagca | 300 |
| ttacgtaggt acgttttctt tttcttcccg gagagatgat acaataatca tgtaaaccca | 360 |
| gaatttaaaa aatattcttt actataaaaa ttttaattag ggaacgtatt attttttaca | 420 |
| tgacaccttt tgagaaagag ggacttgtaa tatgggacaa atgaacaatt tctaagaaat | 480 |
| gggcatatga ctctcagtac aatggaccaa attccctcca gtcggcccag caatacaaag | 540 |
| ggaaagaaat gagggggccc acaggccacg gcccactttt ctccgtggtg gggagatcca | 600 |
| gctagaggtc cggcccacaa gtgggccttg ccccgtggga cggtgggatt gcagagcgcg | 660 |
| tgggcggaaa caacagttta gtaccacctc gctcacgcaa cgacgcgacc acttgcttat | 720 |
| aagctgctgc gctgaggctc ag | 742 |

<210> SEQ ID NO 71
<211> LENGTH: 83
<212> TYPE: DNA
<213> ORGANISM: Artificial Sequence
<220> FEATURE:
<223> OTHER INFORMATION: The nucleotide sequence of gRNA scaffold

<400> SEQUENCE: 71

| | |
|---|---|
| gttttagagc tagaaatagc aagttaaaat aaggctagtc cgttatcaac ttgaaaaagt | 60 |
| ggcaccgagt cggtgctttt ttt | 83 |

<210> SEQ ID NO 72
<211> LENGTH: 3378
<212> TYPE: DNA
<213> ORGANISM: Artificial Sequence
<220> FEATURE:

<223> OTHER INFORMATION: The nucleotide sequence of pMD19GW-Adv.BstX vector

<400> SEQUENCE: 72

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagaga ttcaaataat gattttattt tgactgatag tgacctgttc gttgcaacaa     480
attgataagc aatgcttttt tataatgcca actttgtaca aaaaagcagg ctgccacgat     540
tccatctgct tggctcgacg gagcctgaca tttatattcc ccagaacatc aggttaatgg     600
cgtttttgat gtcattttcg cggtggctga gatcagccac ttcttccccg ataacggaga     660
ccggcacact ggccatatcg gtggtcatca tgcgccagct ttcatccccg atatgcacca     720
ccgggtaaag ttcacgggag actttatctg acagcagacg tgcactggcc aggggggatca     780
ccatccgtcg cccgggcgtg tcaataatat cactctgtac atccacaaac agacgataac     840
ggctctctct tttataggtg taaaccttaa actgcatctc gagagcatac ctcttttttga    900
catacttcgg gtatacatat cagtatatat tcttataccg caaaaatcag cgcgcaaata     960
cgcatactgt tatctggctt ttagtaagcc ggatctccaa gcggctggaa tcttggaccc    1020
agctttcttg tacaaagttg gcattataag aaagcattgc ttatcaattt gttgcaacga    1080
acaggtcact atcagtcaaa ataaaatcat tatttgaatc gtcgacctgc aggcatgcaa    1140
gcttggcgta atcatggtca tagctgtttc ctgtgtgaaa ttgttatccg ctcacaattc    1200
cacacaacat acgagccgga agcataaagt gtaaagcctg cggtgcctaa tgagtgagct    1260
aactcacatt aattgcgttg cgctcactgc ccgctttcca gtcgggaaac ctgtcgtgcc    1320
agctgcatta atgaatcggc caacgcgcgg ggagaggcgg tttgcgtatt gggcgctctt    1380
ccgcttcctc gctcactgac tcgctgcgct cggtcgttcg gctgcggcga gcggtatcag    1440
ctcactcaaa ggcggtaata cggttatcca cagaatcagg gataacgca ggaaagaaca     1500
tgtgagcaaa aggccagcaa aaggccagga accgtaaaaa ggccgcgttg ctggcgtttt    1560
tccataggct ccgcccccct gacgagcatc acaaaaatcg acgctcaagt cagaggtggc    1620
gaaacccgac aggactataa agataccagg cgtttccccc tggaagctcc ctcgtgcgct    1680
ctcctgttcc gaccctgccg cttaccggat acctgtccgc ctttctccct cgggaagcg     1740
tggcgctttc tcatagctca cgctgtaggt atctcagttc ggtgtaggtc gttcgctcca    1800
agctgggctg tgtgcacgaa ccccccgttc agcccgaccg ctgcgcctta ccggtaact     1860
atcgtcttga gtccaacccg gtaagacacg acttatcgcc actggcagca gccactggta    1920
acaggattag cagagcgagg tatgtaggcg gtgctacaga gttcttgaag tggtggccta    1980
actacggcta cactagaaga acagtatttg gtatctgcgc tctgctgaag ccagttacct    2040
tcggaaaaag agttggtagc tcttgatccg gcaaacaaac caccgctggt agcggtggtt    2100
tttttgtttg caagcagcag attacgcgca gaaaaaaagg atctcaagaa gatcctttga    2160
tcttttctac ggggtctgac gctcagtgga acgaaaactc acgttaaggg attttggtca    2220
```

```
tgagattatc aaaaaggatc ttcacctaga tccttttaaa ttaaaaatga agttttaaat    2280
caatctaaag tatatatgag taaacttggt ctgacagtta ccaatgctta atcagtgagg    2340
cacctatctc agcgatctgt ctatttcgtt catccatagt tgcctgactc cccgtcgtgt    2400
agataactac gatacgggag ggcttaccat ctggccccag tgctgcaatg ataccgcgag    2460
acccacgctc accggctcca gatttatcag caataaacca gccagccgga agggccgagc    2520
gcagaagtgg tcctgcaact ttatccgcct ccatccagtc tattaattgt tgccgggaag    2580
ctagagtaag tagttcgcca gttaatagtt tgcgcaacgt tgttgccatt gctacaggca    2640
tcgtggtgtc acgctcgtcg tttggtatgg cttcattcag ctccggttcc caacgatcaa    2700
ggcgagttac atgatccccc atgttgtgca aaaaagcggt tagctccttc ggtcctccga    2760
tcgttgtcag aagtaagttg gccgcagtgt tatcactcat ggttatggca gcactgcata    2820
attctcttac tgtcatgcca tccgtaagat gcttttctgt gactggtgag tactcaacca    2880
agtcattctg agaatagtgt atgcggcgac cgagttgctc ttgcccggcg tcaatacggg    2940
ataataccgc gccacatagc agaactttaa aagtgctcat cattggaaaa cgttcttcgg    3000
ggcgaaaact ctcaaggatc ttaccgctgt tgagatccag ttcgatgtaa cccactcgtg    3060
cacccaactg atcttcagca tcttttactt tcaccagcgt ttctgggtga gcaaaaacag    3120
gaaggcaaaa tgccgcaaaa aagggaataa gggcgacacg gaaatgttga atactcatac    3180
tcttcctttt tcaatattat tgaagcattt atcagggtta ttgtctcatg agcggataca    3240
tatttgaatg tatttagaaa aataaacaaa tgggggttcc gcgcacattt ccccgaaaag    3300
tgccacctga cgtctaagaa accattatta tcatgacatt aacctataaa aataggcgta    3360
tcacgaggcc ctttcgtc                                                  3378

<210> SEQ ID NO 73
<211> LENGTH: 12705
<212> TYPE: DNA
<213> ORGANISM: Artificial Sequence
<220> FEATURE:
<223> OTHER INFORMATION: The nucleotide sequence of pCAMBIA1300DsRed-
      35S-GW vector

<400> SEQUENCE: 73
gatctggtac cgagctcaca agtttgtaca aaaaagctga cgagaaacg taaaatgata      60 taaatatcaa tatattaaat tagattttgc ataaaaaaca gactacataa tactgtaaaa    120
cacaacatat ccagtcacta tggcggccgc attaggcacc ccaggcttta cactttatgc    180
ttccggctcg tataatgtgt ggattttgag ttaggatccg gcttactaaa agccagataa    240
cagtatgcgt atttgcgcgc tgattttttgc ggtataagaa tatatactga tatgtatacc    300
cgaagtatgt caaaaagagg tatgctctcg agatgcagtt taaggtttac acctataaaa    360
gagagagccg ttatcgtctg tttgtggatg tacagagtga tattattgac acgcccgggc    420
gacggatggt gatcccctg ccagtgcac gtctgctgtc agataaagtc tcccgtgaac    480
tttacccggt ggtgcatatc ggggatgaaa gctggcgcat gatgaccacc gatatggcca    540
gtgtgccggt ctccgttatc ggggaagaag tggctgatct cagccaccgc gaaaatgaca    600
tcaaaaacgc cattaacctg atgttctggg aatataaat gtcaggctcc gtcgaccata    660
gtgactggat atgttgtgtt ttacagtatt atgtagtctg ttttttatgc aaaatctaat    720
ttaatatatt gatatttata tcattttacg tttctcgttc agctttcttg tacaaagtgg    780
tgcctcgacc tccaagctgg gccacaactg aagcggccgc gtttcttaag attgaatcct    840
```

```
gttgccggtc ttgcgatgat tatcatataa tttctgttga attacgttaa gcatgtaata    900
attaacatgt aatgcatgac gttatttatg agatgggttt ttatgattag agtcccgcaa    960
ttatacattt aatacgcgat agaaaacaaa atatagcgcg caaactagga taaattatcg   1020
cgcgcggtgt catctatgtt actagatcgg gactagagaa ttcgtaatca tgtcatagct   1080
gtttcctgtg tgaaattgtt atccgctcac aattccacac aacatacgag ccggaagcat   1140
aaagtgtaaa gcctggggtg cctaatgagt gagctaactc acattaattg cgttgcgctc   1200
actgcccgct ttccagtcgg gaaacctgtc gtgccagctg cattaatgaa tcggccaacg   1260
cgcggggaga ggcggtttgc gtattggcta gagcagcttg ccaacatggt ggagcacgac   1320
actctcgtct actccaagaa tatcaaagat acagtctcag aagaccaaag ggctattgag   1380
acttttcaac aaagggtaat atcgggaaac ctcctcggat tccattgccc agctatctgt   1440
cacttcatca aaaggacagt agaaaaggaa ggtggcacct acaaatgcca tcattgcgat   1500
aaaggaaagg ctatcgttca agatgcctct gccgacagtg gtcccaaaga tggaccccca   1560
cccacgagga gcatcgtgga aaagaagac gttccaacca cgtcttcaaa gcaagtggat   1620
tgatgtgata acatggtgga gcacgacact ctcgtctact ccaagaatat caaagataca   1680
gtctcagaag accaaagggc tattgagact tttcaacaaa gggtaatatc gggaaacctc   1740
ctcggattcc attgcccagc tatctgtcac ttcatcaaaa ggacagtaga aaaggaaggt   1800
ggcacctaca aatgccatca ttgcgataaa ggaaaggcta tcgttcaaga tgcctctgcc   1860
gacagtggtc ccaaagatgg accccaccc acgaggagca tcgtggaaaa agaagacgtt   1920
ccaaccacgt cttcaaagca gtggattga tgtgatatct ccactgacgt aagggatgac   1980
gcacaatccc actatccttc gcaagacctt cctctatata aggaagttca tttcatttgg   2040
agaggacacg ctgaaatcac cagtctctct ctacaaatct atctctctcg agctttcgca   2100
gatcccgggg ggcaatgaga tatgaaaaag cctgaactca ccgcgacgtc tgtcgagaag   2160
tttctgatcg aaaagttcga cagcgtctcc gacctgatgc agctctcgga gggcgaagaa   2220
tctcgtgctt tcagcttcga tgtaggaggg cgtggatatg tcctgcgggt aaatagctgc   2280
gccgatggtt tctacaaaga tcgttatgtt tatcggcact ttgcatcggc cgcgctcccg   2340
attccggaag tgcttgacat tggggagttt agcgagagcc tgacctattg catctcccgc   2400
cgttcacagg gtgtcacgtt gcaagacctg cctgaaaccg aactgcccgc tgttctacaa   2460
ccggtcgcgg aggctatgga tgcgatcgct gcggccgatc ttagccagac gagcgggttc   2520
ggcccattcg gaccgcaagg aatcggtcaa tacactacat ggcgtgattt catatgcgcg   2580
attgctgatc cccatgtgta tcactggcaa actgtgatgg acgacaccgt cagtgcgtcc   2640
gtcgcgcagg ctctcgatga gctgatgctt tgggccgagg actgccccga agtccggcac   2700
ctcgtgcacg cggatttcgg ctccaacaat gtcctgacgg acaatggccg cataacagcg   2760
gtcattgact ggagcgaggc gatgttcggg gattcccaat acgaggtcgc caacatcttc   2820
ttctggaggc cgtggttggc ttgtatggag cagcagacgc gctacttcga gcggaggcat   2880
ccggagcttg caggatcgcc acgactccgg gcgtatatgc tccgcattgg tcttgaccaa   2940
ctctatcaga gcttggttga cggcaatttc gatgatgcag cttgggcgca gggtcgatgc   3000
gacgcaatcg tccgatccgg agccgggact gtcgggcgta cacaaatcgc ccgcagaagc   3060
gcggccgtct ggaccgatgg ctgtgtagaa gtactcgccg atagtggaaa ccgacgcccc   3120
agcactcgtc cgagggcaaa gaaatagagt agatgccgac cggatctgtc gatcgacaag   3180
ctcgagtttc tccataataa tgtgtgagta gttcccagat aagggaatta gggttcctat   3240
```

```
agggtttcgc tcatgtgttg agcatataag aaacccttag tatgtatttg tatttgtaaa   3300
atacttctat caataaaatt tctaattcct aaaaccaaaa tccagtacta aaatccagat   3360
cccccgaatt aattcggcgt taattcagta cattaaaaac gtccgcaatg tgttattaag   3420
ttgtctaagc gtcaatttgt ttacaccaca atatatcctg ccaccagcca gccaacagct   3480
ccccgaccgg cagctcggca caaaatcacc actcgataca ggcagcccat cagtccggga   3540
cggcgtcagc gggagagccg ttgtaaggcg gcagactttg ctcatgttac cgatgctatt   3600
cggaagaacg gcaactaagc tgccgggttt gaaacacgga tgatctcgcg gagggtagca   3660
tgttgattgt aacgatgaca gagcgttgct gcctgtgatc accgcggttt caaaatcggc   3720
tccgtcgata ctatgttata cgccaacttt gaaaacaact ttgaaaaagc tgttttctgg   3780
tatttaaggt tttagaatgc aaggaacagt gaattggagt tcgtcttgtt ataattagct   3840 tcttgggta tctttaaata ctgtagaaaa gaggaaggaa ataataaatg gctaaaatga   3900
gaatatcacc ggaattgaaa aaactgatcg aaaaataccg ctgcgtaaaa gatacggaag   3960
gaatgtctcc tgctaaggta tataagctgg tgggagaaaa tgaaaaccta tatttaaaaa   4020
tgacggacag ccggtatata gggaccacct atgatgtgga acgggaaaag gacatgatgc   4080
tatggctgga aggaaagctg cctgttccaa aggtcctgca ctttgaacgg catgatggct   4140
ggagcaatct gctcatgagt gaggccgatg gcgtcctttg ctcggaagag tatgaagatg   4200
aacaaagccc tgaaaagatt atcgagctgt atgcggagtg catcaggctc tttcactcca   4260
tcgacatatc ggattgtccc tatacgaata gcttagacag ccgcttagcc gaattggatt   4320
acttactgaa taacgatctg gccgatgtgg attgcgaaaa ctgggaagaa gacactccat   4380
ttaaagatcc gcgcgagctg tatgattttt taaagacgga aaagcccgaa gaggaacttg   4440
tcttttccca cggcgacctg ggagacagca acatctttgt gaaagatggc aaagtaagtg   4500
gctttattga tcttgggaga agcggcaggg cggacaagtg gtatgacatt gccttctgcg   4560
tccggtcgat cagggaggat atcggggaag aacagtatgt cgagctattt tttgacttac   4620
tggggatcaa gcctgattgg gagaaaataa aatattatat tttactggat gaattgttt   4680 agtacctaga atgcatgacc aaaatccctt aacgtgagtt ttcgttccac tgagcgtcag   4740
accccgtaga aagatcaaa ggatcttctt gagatccttt ttttctgcgc gtaatctgct   4800
gcttgcaaac aaaaaaacca ccgctaccag cggtggtttg tttgccggat caagagctac   4860
caactctttt tccgaaggta actggcttca gcagagcgca gataccaaat actgtccttc   4920
tagtgtagcc gtagttaggc caccacttca agaactctgt agcaccgcct acatacctcg   4980
ctctgctaat cctgttacca gtggctgctg ccagtggcga taagtcgtgt cttaccgggt   5040
tggactcaag acgatagtta ccggataagg cgcagcggtc gggctgaacg gggggttcgt   5100
gcacacagcc cagcttggag cgaacgacct acaccgaact gagatacctca gcgtgagc   5160 tatgagaaag cgccacgctt cccgaaggga gaaaggcgga caggtatccg gtaagcggca   5220
gggtcggaac aggagagcgc acgagggagc ttccaggggg aaacgcctgg tatctttata   5280
gtcctgtcgg gtttcgccac ctctgacttg agcgtcgatt tttgtgatgc tcgtcagggg   5340
ggcggagcct atgaaaaaac gccagcaacg cggccttttt acggttcctg gcctttgct   5400 ggccttttgc tcacatgttc tttcctgcgt tatcccctga ttctgtggat aaccgtatta   5460
ccgcctttga gtgagctgat accgctcgcc gcagccgaac gaccgagcgc agcgagtcag   5520
tgagcgagga agcggaagag cgcctgatgc ggtattttct ccttacgcat ctgtgcggta   5580
```

```
tttcacaccg catatggtgc actctcagta caatctgctc tgatgccgca tagttaagcc    5640
agtatacact ccgctatcgc tacgtgactg ggtcatggct gcgccccgac acccgccaac    5700
acccgctgac gcgccctgac gggcttgtct gctcccggca tccgcttaca gacaagctgt    5760
gaccgtctcc gggagctgca tgtgtcagag gttttcaccg tcatcaccga aacgcgcgag    5820
gcagggtgcc ttgatgtggg cgccggcggt cgagtggcga cggcgcggct tgtccgcgcc    5880
ctggtagatt gcctggccgt aggccagcca tttttgagcg gccagcggcc gcgataggcc    5940
gacgcgaagc ggcggggcgt agggagcgca gcgaccgaag ggtaggcgct ttttgcagct    6000
cttcggctgt gcgctggcca gacagttatg cacaggccag gcgggtttta agagttttaa    6060
taagttttaa agagttttag gcggaaaaat cgccttttt ctcttttata tcagtcactt     6120
acatgtgtga ccggttccca atgtacggct ttgggttccc aatgtacggg ttccggttcc    6180
caatgtacgg ctttgggttc ccaatgtacg tgctatccac aggaaagaga ccttttcgac    6240
cttttttccc tgctagggca atttgcccta gcatctgctc cgtacattag gaaccggcgg    6300
atgcttcgcc ctcgatcagg ttgcggtagc gcatgactag gatcgggcca gcctgccccg    6360
cctcctcctt caaatcgtac tccggcaggt catttgaccc gatcagcttg cgcacggtga    6420
aacagaactt cttgaactct ccggcgctgc cactgcgttc gtagatcgtc ttgaacaacc    6480
atctggcttc tgccttgcct gcggcgcggc gtgccaggcg gtagagaaaa cggccgatgc    6540
cgggatcgat caaaaagtaa tcggggtgaa ccgtcagcac gtccgggttc ttgccttctg    6600
tgatctcgcg gtacatccaa tcagctagct cgatctcgat gtactccggc cgcccggttt    6660
cgctctttac gatcttgtag cggctaatca aggcttcacc ctcggatacc gtcaccaggc    6720
ggccgttctt ggccttcttc gtacgctgca tggcaacgtg cgtggtgttt aaccgaatgc    6780
aggtttctac caggtcgtct ttctgctttc cgccatcggc tcgccggcag aacttgagta    6840
cgtccgcaac gtgtggacgg aacacgcggc cgggcttgtc tcccttccct tcccggtatc    6900
ggttcatgga ttcggttaga tgggaaaccg ccatcagtac caggtcgtaa tcccacacac    6960
tggccatgcc ggccggccct gcggaaacct ctacgtgccc gtctggaagc tcgtagcgga    7020
tcacctcgcc agctcgtcgg tcacgcttcg acagacggaa aacggccacg tccatgatgc    7080
tgcgactatc gcgggtgccc acgtcataga gcatcggaac gaaaaaatct ggttgctcgt    7140
cgcccttggg cggcttccta atcgacgcg caccggctgc cggcggttgc cgggattctt     7200
tgcggattcg atcagcggcc gcttgccacg attcaccggg gcgtgcttct gcctcgatgc    7260
gttgccgctg ggcggcctgc gcggccttca acttctccac caggtcatca cccagcgccg    7320
cgccgatttg taccgggccg gatggtttgc gaccgtcacg ccgattcctc gggcttgggg    7380
gttccagtgc cattgcaggg ccggcagaca acccagccgc ttacgcctgg ccaaccgccc    7440
gttcctccac acatggggca ttccacggcg tcggtgcctg gttgttcttg attttccatg    7500
ccgcctcctt tagccgctaa aattcatcta ctcatttatt catttgctca tttactctgg    7560
tagctgcgcg atgtattcag atagcagctc ggtaatggtc ttgccttggc gtaccgcgta    7620
catcttcagc ttggtgtgat cctccgccgg caactgaaag ttgacccgct tcatggctgg    7680
cgtgtctgcc aggctggcca acgttgcagc cttgctgctg cgtgcgctcg acggccggc    7740 acttagcgtg tttgtgcttt tgctcatttt ctctttacct cattaactca aatgagtttt    7800
gatttaattt cagcggccag cgcctggacc tcgcgggcag cgtcgccctc gggttctgat    7860
tcaagaacgg ttgtgccggc ggcggcagtg cctgggtagc tcacgcgctg cgtgatacgg    7920
gactcaagaa tgggcagctc gtacccggcc agcgcctcgg caacctcacc gccgatgcgc    7980
```

```
gtgcctttga tcgcccgcga cacgacaaag gccgcttgta gccttccatc cgtgacctca    8040
atgcgctgct taaccagctc caccaggtcg gcggtggccc atatgtcgta agggcttggc    8100
tgcaccggaa tcagcacgaa gtcggctgcc ttgatcgcgg acacagccaa gtccgccgcc    8160
tggggcgctc cgtcgatcac tacgaagtcg cgccggccga tggccttcac gtcgcggtca    8220
atcgtcgggc ggtcgatgcc gacaacggtt agcggttgat cttcccgcac ggccgcccaa    8280
tcgcgggcac tgccctgggg atcggaatcg actaacagaa catcggcccc ggcgagttgc    8340
agggcgcggg ctagatgggt tgcgatggtc gtcttgcctg acccgccttt ctggttaagt    8400
acagcgataa ccttcatgcg ttccccttgc gtatttgttt atttactcat cgcatcatat    8460
acgcagcgac cgcatgacgc aagctgtttt actcaaatac acatcacctt tttagacggc    8520
ggcgctcggt ttcttcagcg gccaagctgg ccggccaggc cgccagcttg gcatcagaca    8580
aaccggccag gatttcatgc agccgcacgg ttgagacgtg cgcgggcggc tcgaacacgt    8640
acccggccgc gatcatctcc gcctcgatct cttcggtaat gaaaaacggt tcgtcctggc    8700
cgtcctggtg cggtttcatg cttgttcctc ttggcgttca ttctcggcgg ccgccagggc    8760
gtcggcctcg gtcaatgcgt cctcacggaa ggcaccgcgc cgcctggcct cggtgggcgt    8820
cacttcctcg ctgcgctcaa gtgcgcggta cagggtcgag cgatgcacgc caagcagtgc    8880
agccgcctct ttcacggtgc ggccttcctg gtcgatcagc tcgcgggcgt gcgcgatctg    8940
tgccggggtg agggtagggc gggggccaaa cttcacgcct cgggccttgg cggcctcgcg    9000
cccgctccgg gtgcggtcga tgattaggga acgctcgaac tcggcaatgc cggcgaacac    9060
ggtcaacacc atgcggccgg ccggcgtggt ggtgtcggcc cacggctctg ccaggctacg    9120
caggcccgcg ccggcctcct ggatgcgctc ggcaatgtcc agtaggtcgc gggtgctgcg    9180
ggccaggcgg tctagcctgg tcactgtcac aacgtcgcca gggcgtaggt ggtcaagcat    9240
cctggccagc tccgggcggt cgcgcctggt gccggtgatc ttctcggaaa acagcttggt    9300
gcagccggcc gcgtgcagtt cggcccgttg gttggtcaag tcctggtcgt cggtgctgac    9360
gcgggcatag cccagcaggc cagcggcggc gctcttgttc atggcgtaat gtctccggtt    9420
ctagtcgcaa gtattctact ttatgcgact aaaacacgcg acaagaaaac gccaggaaaa    9480
gggcagggcg gcagcctgtc gcgtaactta ggacttgtgc gacatgtcgt tttcagaaga    9540
cggctgcact gaacgtcaga agccgactgc actatagcag cggaggggtt ggatcaaagt    9600
actttgatcc cgaggggaac cctgtggttg gcatgcacat acaaatggac gaacggataa    9660
accttttcac gcccttttaa atatccgatt attctaataa acgctctttt ctcttaggtt    9720
tacccgccaa tatatcctgt caaacactga tagtttaaac tgaaggcggg aaacgacaat    9780
ctgatccaag ctcaagctgc tctagcattc gccattcagg ctgcgcaact gttgggaagg    9840
gcgatcggtg cgggcctctt cgctattacg ccagctggcg aaaggggat gtgctgcaag     9900 gcgattaagt tgggtaacgc cagggttttc ccagtcacga cgttgtaaaa cgacggccag    9960
tgccaagctt cgaagctggc cgctctagaa ctagtggatc tcgatgtgta gtctacgaga    10020
agggttaacc gtctcttcgt gagaataacc gtggcctaaa aataagccga tgaggataaa    10080
taaaatgtgg tggtacagta cttcaagagg tttactcatc aagaggatgc ttttccgatg    10140
agctctagta gtacatcgga cctcacatac ctccattgtg gtgaaatatt ttgtgctcat    10200
ttagtgatgg gtaaattttg tttatgtcac tctaggtttt gacatttcag ttttgccact    10260
cttaggtttt gacaaataat ttccattccg cggcaaaagc aaaacaattt tattttactt    10320
```

```
ttaccactct tagctttcac aatgtatcac aaatgccact ctagaaattc tgtttatgcc    10380
acagaatgtg aaaaaaaaca ctcacttatt tgaagccaag gtgttcatgg catggaaatg    10440
tgacataaag taacgttcgt gtataagaaa aaattgtact cctcgtaaca agagacggaa    10500
acatcatgag acaatcgcgt ttggaaggct ttgcatcacc tttggatgat gcgcatgaat    10560
ggagtcgtct gcttgctagc cttcgcctac cgcccactga gtccgggcgg caactaccat    10620
cggcgaacga cccagctgac ctctaccgac cggacttgaa tgcgctacct tcgtcagcga    10680
cgatggccgc gtacgctggc gacgtgcccc cgcatgcatg gcggcacatg gcgagctcag    10740
accgtgcgtg gctggctaca aatacgtacc ccgtgagtgc cctagctaga aacttacacc    10800
tgcaactgcg agagcgagcg tgtgagtgta gccgagtaga tcctcgccac catggcctcc    10860
tccgagaacg tcatcaccga gttcatgcgc ttcaaggtgc gcatggaggg caccgtgaac    10920
ggccacgagt tcgagatcga gggcgagggc gagggccgcc cctacgaggg ccacaacacc    10980
gtgaagctga aggtgacgaa gggcggcccc ctgcccttcg cctgggacat cctgtccccc    11040
cagttccagt acggctccaa ggtgtacgtg aagcaccccg ccgacatccc cgactacaag    11100
aagctgtcct tccccgaggg cttcaagtgg gagcgcgtga tgaacttcga ggacggcggc    11160
gtggcgaccg tgacccagga ctcctccctg caggacggct gcttcatcta caaggtgaag    11220
ttcatcggcg tgaacttccc ctccgacggc cccgtgatgc agaagaagac catgggctgg    11280
gaggcctcca ccgagcgcct gtaccccgcg acggcgtgc tgaagggcga gacccacaag    11340
gccctgaagc tgaaggacgg cggccactac ctggtggagt tcaagtccat ctacatggcc    11400
aagaagcccg tgcagctgcc cggctactac tacgtggacg ccaagctgga catcacctcc    11460
cacaacgagg actacaccat cgtggagcag tacgagcgca ccgagggccg ccaccacctg    11520
ttcctgtagc ggcccatgga tattcgaacg cgtaggtacc acatggttaa cctagacttg    11580
tccatcttct ggattggcca acttaattaa tgtatgaaat aaaaggatgc acacatagtg    11640
acatgctaat cactataatg tgggcatcaa agttgtgtgt tatgtgtaat tactagttat    11700
ctgaataaaa gagaaagaga tcatccatat ttcttatcct aaatgaatgt cacgtgtctt    11760
tataattctt tgatgaacca gatgcatttc attaaccaaa tccatataca tataaatatt    11820
aatcatatat aattaatatc aattgggtta gcaaacaaa tctagtctag gtgtgttttg    11880
cgaatgcggc ccgccaaagc ttagagcagc ttggcaacat ggtggagcac gacactctcg    11940
tctactccaa gaatatcaaa gatacagtct cagaagacca aagggctatt gagacttttc    12000
aacaaagggt aatatcggga aacctcctcg gattccattg cccagctatc tgtcacttca    12060
tcaaaaggac agtagaaaag gaaggtggca cctacaaatg ccatcattgc gataaaggaa    12120
aggctatcgt tcaagatgcc tctgccgaca gtggtcccaa agatggaccc cacccacga    12180 ggagcatcgt ggaaaaagaa gacgttccaa ccacgtcttc aaagcaagtg gattgatgtg    12240
aacatggtgg agcacgacac tctcgtctac tccaagaata tcaaagatac agtctcagaa    12300
gaccaaaggg ctattgagac ttttcaacaa agggtaatat cgggaaacct cctcggattc    12360
cattgcccag ctatctgtca cttcatcaaa aggacagtag aaaggaagg tggcacctac    12420 aaatgccatc attgcgataa aggaaaggct atcgttcaag atgcctctgc cgacagtggt    12480
cccaaagatg gacccccacc cacgaggagc atcgtggaaa agaagacgt tccaaccacg    12540 tcttcaaagc aagtggattg atgtgatatc tccactgacg taaggatga cgcacaatcc    12600 cactatcctt cgcaagaccc ttcctctata taaggaagtt catttcattt ggagaggaca    12660
cgctgaaatc accagtctct ctctacaaat ctatctctct gcaga                   12705
```

<210> SEQ ID NO 74
<211> LENGTH: 2003
<212> TYPE: DNA
<213> ORGANISM: Oryza sativa

<400> SEQUENCE: 74

| | | | | | |
|---|---|---|---|---|---|
| tctgcttgcc | gccgcccggc | accatgaggt | tgctcaaggt | cctcgcgatc | tgccgcttga | 60 |
| gctgacctct | cctcggtggc | ggcctcttct | ccttcatgct | gttggtgtac | tggtggtggc | 120 |
| actccaccat | ggtctcttaa | ttactatctt | taattaagag | ctcttctttt | tttttccttc | 180 |
| cagaaactcc | ctcttaatta | tgatttgctc | tgccataact | atatcagtat | atatgttctt | 240 |
| tgtgatggaa | agtaggatgg | aattttagg | tgagggctct | tgcagtctag | tgcaagtttc | 300 |
| actagctata | gcctgcaggt | taatttgatg | catgcatgc | gttaattttt | ttcttgtttt | 360 |
| tcctttgcag | gagaataaat | tgactgcttt | aaggtcagta | cttaaagacc | gggtcccatg | 420 |
| atgtttatgg | gtgtgaaacc | tgggaatttt | acgcccaaaa | actcacggct | gcaatgagtt | 480 |
| tggtcactaa | tacgagcatc | attagctata | taggcaagtt | gggcgtgtgg | atcagggagg | 540 |
| gtactgtgta | tcactcagca | aaagcatatg | tgaaaactaa | caaattatat | tacagtgtgc | 600 |
| tagaatgtat | agatgctgtg | atgtctctct | tattagagtc | ttattatata | gagagagagc | 660 |
| gcagtgcttt | acttttgtta | gttactgaga | atgtcttttc | aaccaacaaa | atgctatacc | 720 |
| tatctttccc | aaaagtataa | catagataat | taattaagct | agttcattag | gcagaactca | 780 |
| ttaactcaag | gctttgaacg | gtggatagat | cgccagaaac | atctatggca | tctgatcttt | 840 |
| ctcctagata | tccagagttt | tgagtgacat | cgacatcatg | taaaagtaaa | catgttattc | 900 |
| ctgaatccct | ctctttaatt | tgttcatctt | cagacaatgc | ctttgcaact | agctcttttc | 960 |
| tctaaaaaaa | acagaaaaca | ttaattacat | gacaaaacga | ttatcaatca | caattctttt | 1020 |
| ccgataatga | tcaacatgca | tcacatggat | aataggtgca | caagctagct | cgtcagaaga | 1080 |
| agcatgcgat | aaggtcaaag | caatcaaagc | aaagccaaag | ctatttcggc | cggcggattg | 1140 |
| ctgatcaagg | tgtccatcgt | tgagcgggtt | gcatgctgcg | agagagccag | tgacactgac | 1200 |
| acctcaagct | cgatcgtcag | agtccccct | caggtcaaac | agtgaccaca | ttctctgaac | 1260 |
| cttgaagcta | agctagctgc | tgctaccgct | cttaattcgt | cagaagaagc | agccgtcagt | 1320 |
| tattgatcag | cacgtgttct | tcttcttctt | aacccagctt | aatcaagatg | tcaatcgatt | 1380 |
| aatcgatctg | tcactcgatg | atagagcaaa | tgaaatggca | aatcgactcc | tattttgac | 1440 |
| agcaatgtct | cggagagact | gtttggtcag | ttggtcacgt | ccatgatgag | cacgaacaga | 1500 |
| aagaagcaaa | tatgtgcgga | cagtggtaga | catcaggtag | aaattttgc | ctgatataat | 1560 |
| taagcacgtt | aaccttgccc | tccaggtagt | agtaatcaat | tgtcatttct | gtcgttttca | 1620 |
| gggcatagat | gcccttatta | gtgccatgat | cacatcacaa | acctcccggc | ccagaagtgg | 1680 |
| tcaagttgtt | ccttcaaaga | atagtaaaaa | aacacacacc | cgcccggct | gatgcaaagt | 1740 |
| tacaaccgag | attaaattaa | ttaacatgtg | cggcaacaga | acagcatgac | acttcagatc | 1800 |
| actccgccta | taaatacttc | ttgccttctc | aatttctcaa | atcatctcca | cacactaaac | 1860 |
| tagaacctgc | ttcacaacac | aacacaacta | ctacctgttc | aactgctact | actgcaacga | 1920 |
| gagagaaaaa | acaatttcag | tttcagaaga | gagaaaggag | caactgagca | agaactgaag | 1980 |
| aaaatagaga | gagagaagcc | atg | | | | 2003 |

<210> SEQ ID NO 75

```
<211> LENGTH: 225
<212> TYPE: DNA
<213> ORGANISM: Oryza sativa

<400> SEQUENCE: 75
cggtctacca cgtcgacttc tcggcgtgat catcttaatc aggcagcgac ggcgggggcg    60
acgctccatg gatttggact catcgtgtgc atgagttact taagtaccaa ttttaggaag   120
ttagtagtat gattacaata ttggacaaag atatttgaca tcgatatgta tatgattccg   180
ctgcatttct gattaattac cagcattcac ctgtttctct gattc                  225

<210> SEQ ID NO 76
<211> LENGTH: 1602
<212> TYPE: DNA
<213> ORGANISM: Oryza sativa

<400> SEQUENCE: 76
atggctgcca cggcggcgga gaccgccgcc gccgccaccg ccaccgccgg cggctgcagg    60
gtcgtgcggt ggcggcgctg gacgttcgcc agcctgggcg cgctgctgtc caacctcggc   120
ccggtgtggt tcctcatcgc gccgctgctc gccgcgtacg cgccgcggcg gctgctcctg   180
acctacttca acctcgtcct ccgccgccgg gcgccgccgc tgctcgccgc cgtcgacccc   240
tacgtcaccg tcgacatccc cgaccccggc gccgccgacg cgcaccagca gtactaccac   300
caccgctcca ggctcggcgg ccgccgcgcc ggcgacaacg cgtacgagga ggtgaaggcg   360
tacctgagcg ccgcgtgctc gtcggaggcc cgcgagctcc gcgccgaggc cgcggcggag   420
ggccgcggcc tcgtcgtcag catgcgcgac gggcaggacg tcgccgacga gttccgcggc   480
gccaccatgt ggtggtcgtc ggtggacgag gagcagcagg gcggcggcgc gcggcggcgc   540
agccagcggc tcacgttcca ccagctccac cggcggctcg tcgtcgacga gtacctcccc   600
cacgtccgcc gccgcggccg cgagctcctc ttccacaacc gccgccgccg cctctacacc   660
aacaacaaga gcctcagcta cagcagcgta ccacaaggg cgtggagcta cgtcaacttc   720
gaccacccga ccacgttcga cgctggcc atggagccgg ccaagaaggc ggcgatcatg   780
gacgacctcg acgcgttccg gcgaagcggg gagttctacc gccgcgccgg caagccgtgg   840
aagagggggt acctcctgca cggcccgccc ggcaccggca agtccaccat gatcgcctcc   900
atggccaact acctcgacta cgacatctac gacgtcgagc tcaccatggt gagcgacaac   960
aacgacctcc gcaagctgct gatcgagacg acgagcaagt ccatcgtcgt catcgaggac  1020
atcgactgct ccctcgacct caccggagac cgcgccacgc ggcgtcccgg cgagatccgc  1080
ggcggcggca gcatggtcac cctctccggc ctgctcaact tcatcgacgg gctctggtcg  1140
gcgagcggcg gcgagcgcgt cgtcgtgttc accaccaacc acgtcgagaa gctgacccg  1200 gcgctcatcc gccgcggccg catggacatg cacatcgaga tgtcctactg ccgcgccgcc  1260
gcgttcagga cgctggccaa gaactacctc gacgtcgacg cccaccacct gttcgacgcc  1320
gtggacgaca tactggacaa ggaggacatc acgccggccg acgtcgccga gtgcctcatg  1380
gcggccaagc gctcctccga ctccgacgtg acctcctccc tcgagttctt ggtcgacgag  1440
ctcaacaaga gagcaatgga gaacgccaag gcggtggccg aagcgaaggc gagggcggag  1500
gcggaggcgg aagccaaggc aatggctgac gacgactcgg aggaagacga cgaccattat  1560
tcggatgatt acactgacga cgacgactac gacgacgatt ga                    1602

<210> SEQ ID NO 77
<211> LENGTH: 533
```

<212> TYPE: PRT
<213> ORGANISM: Oryza sativa

<400> SEQUENCE: 77

```
Met Ala Thr Ala Ala Glu Thr Ala Ala Ala Thr Ala Thr Ala
1               5                   10                  15

Gly Gly Cys Arg Val Val Arg Trp Arg Arg Trp Thr Phe Ala Ser Leu
                20                  25                  30

Gly Ala Leu Leu Ser Asn Leu Gly Pro Val Trp Phe Leu Ile Ala Pro
            35                  40                  45

Leu Leu Ala Ala Tyr Ala Pro Arg Arg Leu Leu Leu Thr Tyr Phe Asn
        50                  55                  60

Leu Val Leu Arg Arg Arg Ala Arg Arg Leu Leu Ala Ala Val Asp Pro
65                  70                  75                  80

Tyr Val Thr Val Asp Ile Pro Asp Pro Gly Ala Ala Asp Ala His Gln
                85                  90                  95

Gln Tyr Tyr His His Arg Ser Arg Leu Gly Gly Arg Arg Ala Gly Asp
                100                 105                 110

Asn Ala Tyr Glu Glu Val Lys Ala Tyr Leu Ser Ala Ala Cys Ser Ser
            115                 120                 125

Glu Ala Arg Glu Leu Arg Ala Glu Ala Ala Glu Gly Arg Gly Leu
        130                 135                 140

Val Val Ser Met Arg Asp Gly Gln Asp Val Ala Asp Glu Phe Arg Gly
145                 150                 155                 160

Ala Thr Met Trp Trp Ser Ser Val Asp Glu Glu Gln Gln Gly Gly Gly
                165                 170                 175

Ala Arg Arg Arg Ser Gln Arg Leu Thr Phe His Gln Leu His Arg Arg
            180                 185                 190

Leu Val Val Asp Glu Tyr Leu Pro His Val Arg Arg Gly Arg Glu
        195                 200                 205

Leu Leu Phe His Asn Arg Arg Arg Leu Tyr Thr Asn Asn Lys Ser
        210                 215                 220

Leu Ser Tyr Ser Ser Val Tyr His Lys Ala Trp Ser Tyr Val Asn Phe
225                 230                 235                 240

Asp His Pro Thr Thr Phe Glu Thr Leu Ala Met Glu Pro Ala Lys Lys
                245                 250                 255

Ala Ala Ile Met Asp Asp Leu Asp Ala Phe Arg Arg Ser Gly Glu Phe
            260                 265                 270

Tyr Arg Arg Ala Gly Lys Pro Trp Lys Arg Gly Tyr Leu Leu His Gly
        275                 280                 285

Pro Pro Gly Thr Gly Lys Ser Thr Met Ile Ala Ser Met Ala Asn Tyr
290                 295                 300

Leu Asp Tyr Asp Ile Tyr Asp Val Glu Leu Thr Met Val Ser Asp Asn
305                 310                 315                 320

Asn Asp Leu Arg Lys Leu Leu Ile Glu Thr Thr Ser Lys Ser Ile Val
                325                 330                 335

Val Ile Glu Asp Ile Asp Cys Ser Leu Asp Leu Thr Gly Asp Arg Ala
            340                 345                 350

Thr Arg Arg Pro Gly Glu Ile Arg Gly Gly Ser Met Val Thr Leu
        355                 360                 365

Ser Gly Leu Leu Asn Phe Ile Asp Gly Leu Trp Ser Ala Ser Gly Gly
        370                 375                 380

Glu Arg Val Val Val Phe Thr Thr Asn His Val Glu Lys Leu Asp Pro
385                 390                 395                 400
```

Ala Leu Ile Arg Arg Gly Arg Met Asp Met His Ile Glu Met Ser Tyr
            405                 410                 415

Cys Arg Ala Ala Ala Phe Arg Thr Leu Ala Lys Asn Tyr Leu Asp Val
            420                 425                 430

Asp Ala His His Leu Phe Asp Ala Val Asp Asp Ile Leu Asp Lys Glu
            435                 440                 445

Asp Ile Thr Pro Ala Asp Val Ala Glu Cys Leu Met Ala Ala Lys Arg
    450                 455                 460

Ser Ser Asp Ser Asp Val Thr Ser Ser Leu Glu Phe Leu Val Asp Glu
465                 470                 475                 480

Leu Asn Lys Arg Ala Met Glu Asn Ala Lys Ala Val Ala Glu Ala Lys
            485                 490                 495

Ala Arg Ala Glu Ala Glu Ala Glu Ala Lys Ala Met Ala Asp Asp Asp
            500                 505                 510

Ser Glu Glu Asp Asp Asp His Tyr Ser Asp Asp Tyr Thr Asp Asp Asp
        515                 520                 525

Asp Tyr Asp Asp Asp
        530

<210> SEQ ID NO 78
<211> LENGTH: 1392
<212> TYPE: DNA
<213> ORGANISM: Zea mays

<400> SEQUENCE: 78

```
atggcgacct acgacaaggc gatcgagtcc tacaagaagg cggtgaccac ggcggcgtcg      60
ctggcggcgt cggcgatgct ggtgcgcggc gtggtgaacg agctggtccc ctacgaggtg     120
cgggacctgc tcttctccgg cctgggctac ctgcggtcgc gcatgtcgtc gcggcacacg     180
gtggtgatcg aggagacgga ggggtggacc agcaaccagc tgtacgacgc ggcgcgcacg     240
tacctggcca cccggatcaa caccgacatg cagcgcctcc gcgtcagccg cgtcgacgag     300
ggcaagagcc tcatgttcag catggaggag ggcgaggaga tggccgacgt gcacgccggc     360
gccgagttca ggtggcgcct cgtctgccgc gacggagccg gcaacggcgt gggcaacggc     420
ggcggcaacg gccacggcca cggccacgcc cgcggcggca gctaccgcgt cgaggtccgc     480
tccttcgaga tgagcttcca caggcggcac aaggagaagg ccatcgcgtc ctacctcccg     540
cacatcctcg ccgaggccaa gaagatcaag gaccaggacc ggacgctcaa gatctacatg     600
aacgagggcg agtcctggtt cgccatcgac ctccaccacc cgtccacctt caccacgctc     660
gccatggacc gcaagatgaa gcgggccgtc atggacgacc tcgagaggtt cgtcaggagg     720
aaggagtact acaggcggat cggcaaggcc tggaaacggg gctacctgct ctacggcccg     780
cccgggaccg gcaagtccag cctcattgcc gccatggcca actacctcaa gttcgacgtc     840
tacgatctcg agctcaccga ggtcaactgg aactccacgc tccggaggtt gctcatcggg     900
atgaccaacc gctccatcct cgtcatcgag gacatcgact gctcgctcga tctgcaacaa     960
cgtgcagacg aagctcagga tgctggtacc aaatccaatc cttcagagga caaggtgaca    1020
ctctctgggc tgctcaactt cgtggacggc ctctggtcaa caagcggaga ggagaggatc    1080
atcatcttca cgaccaacta caaggagcgg ctcgacccgg cgctgcttcg gcccggcagg    1140
atggacatgc acatccacat ggggtactgc tgcccagagt cgttcaggat cctggcctcc    1200
aactaccact ccatcaccga ccacgacacg tacctgaga tagaagccct gatcacggag    1260
gtgatggtga ccccagcaga ggtcgctgaa gtgctcatga ggaatgaaga caccgacgtc    1320
```

```
gcgcttgagg gcctcatcca gttcctcaat gggaagaaag accacgccaa ggatgatagt   1380
cgtcaaggtt aa                                                       1392
```

<210> SEQ ID NO 79
<211> LENGTH: 463
<212> TYPE: PRT
<213> ORGANISM: Zea mays

<400> SEQUENCE: 79

```
Met Ala Thr Tyr Asp Lys Ala Ile Glu Ser Tyr Lys Lys Ala Val Thr
1               5                   10                  15

Thr Ala Ala Ser Leu Ala Ala Ser Ala Met Leu Val Arg Gly Val Val
            20                  25                  30

Asn Glu Leu Val Pro Tyr Glu Val Arg Asp Leu Leu Phe Ser Gly Leu
        35                  40                  45

Gly Tyr Leu Arg Ser Arg Met Ser Ser Arg His Thr Val Val Ile Glu
    50                  55                  60

Glu Thr Glu Gly Trp Thr Ser Asn Gln Leu Tyr Asp Ala Ala Arg Thr
65                  70                  75                  80

Tyr Leu Ala Thr Arg Ile Asn Thr Asp Met Gln Arg Leu Arg Val Ser
                85                  90                  95

Arg Val Asp Glu Gly Lys Ser Leu Met Phe Ser Met Glu Glu Gly Glu
            100                 105                 110

Glu Met Ala Asp Val His Ala Gly Ala Glu Phe Arg Trp Arg Leu Val
        115                 120                 125

Cys Arg Asp Gly Ala Gly Asn Gly Val Gly Asn Gly Gly Asn Gly
    130                 135                 140

His Gly His Gly His Ala Arg Gly Gly Ser Tyr Arg Val Glu Val Arg
145                 150                 155                 160

Ser Phe Glu Met Ser Phe His Arg Arg His Lys Glu Lys Ala Ile Ala
                165                 170                 175

Ser Tyr Leu Pro His Ile Leu Ala Glu Ala Lys Lys Ile Lys Asp Gln
            180                 185                 190

Asp Arg Thr Leu Lys Ile Tyr Met Asn Glu Gly Glu Ser Trp Phe Ala
        195                 200                 205

Ile Asp Leu His His Pro Ser Thr Phe Thr Thr Leu Ala Met Asp Arg
    210                 215                 220

Lys Met Lys Arg Ala Val Met Asp Asp Leu Glu Arg Phe Val Arg Arg
225                 230                 235                 240

Lys Glu Tyr Tyr Arg Arg Ile Gly Lys Ala Trp Lys Arg Gly Tyr Leu
                245                 250                 255

Leu Tyr Gly Pro Pro Gly Thr Gly Lys Ser Ser Leu Ile Ala Ala Met
            260                 265                 270

Ala Asn Tyr Leu Lys Phe Asp Val Tyr Asp Leu Glu Leu Thr Glu Val
        275                 280                 285

Asn Trp Asn Ser Thr Leu Arg Arg Leu Leu Ile Gly Met Thr Asn Arg
    290                 295                 300

Ser Ile Leu Val Ile Glu Asp Ile Asp Cys Ser Leu Asp Leu Gln Gln
305                 310                 315                 320

Arg Ala Asp Glu Ala Gln Asp Ala Gly Thr Lys Ser Asn Pro Ser Glu
                325                 330                 335

Asp Lys Val Thr Leu Ser Gly Leu Leu Asn Phe Val Asp Gly Leu Trp
            340                 345                 350
```

```
Ser Thr Ser Gly Glu Glu Arg Ile Ile Phe Thr Thr Asn Tyr Lys
        355                 360                 365

Glu Arg Leu Asp Pro Ala Leu Leu Arg Pro Gly Arg Met Asp Met His
    370                 375                 380

Ile His Met Gly Tyr Cys Cys Pro Glu Ser Phe Arg Ile Leu Ala Ser
385                 390                 395                 400

Asn Tyr His Ser Ile Thr Asp His Asp Thr Tyr Pro Glu Ile Glu Ala
                405                 410                 415

Leu Ile Thr Glu Val Met Val Thr Pro Ala Glu Val Ala Glu Val Leu
                420                 425                 430

Met Arg Asn Glu Asp Thr Asp Val Ala Leu Glu Gly Leu Ile Gln Phe
        435                 440                 445

Leu Asn Gly Lys Lys Asp His Ala Lys Asp Asp Ser Arg Gln Gly
    450                 455                 460

<210> SEQ ID NO 80
<211> LENGTH: 1494
<212> TYPE: DNA
<213> ORGANISM: Sorghum bicolor

<400> SEQUENCE: 80
```

| | |
|---|---|
| atggcgacct acgacaaggc gatggagtcg tacaagaagg cggtgacgac ggtggcgtcg | 60 |
| ctggcggcgt cggcgatgct ggtgcgcggc gtggtgaacg agctggtccc ctacgaggtg | 120 |
| cgggagttcc tcttctccgg cctgggctac ctccggtcgc gcatgtcgtc gcagcacacg | 180 |
| gtggtgatcg aggagacgga agggtgggcg agcaaccagc tgtacgacgc ggcgcgcacg | 240 |
| tacctggcga cgcggatcaa caccgacatg cagcgcctcc gcgtgagccg cgtcgacgag | 300 |
| ggcaagagcc tcatgttcag catggaggaa ggcgaggaga tggccgacgt ccacgccggc | 360 |
| gccgagttca ggtggcgcct cgtctgccgc gacgcgggcg gcgccggcgc cggcaacggc | 420 |
| ggccacgccc acgcccacgc ccgcggcggc ggcggcggcg gcagctaccg cttcgaggtc | 480 |
| cgctccttcg agatgagctt ccacaggcgg cacaaggaca aggccatcgc ctcctacctc | 540 |
| ccgcacatcc tcgccgaggc caagaagatc aaggaccagg acaggacgct caagatctac | 600 |
| atgaacgaag gcgagtcctg gttcgccatc gacctccacc cccttccac cttcaccacg | 660 |
| ctcgccatgg accgcgacat gaagcgctcc gtcatggacg acctcgagag gttcgtcagg | 720 |
| aggaaagagt actacaagag gatcggcaag gcctggaagc gagggtacct gctccacggc | 780 |
| ccgcctggga ccggcaagtc cagcctcatt gccgccatgg ccaactacct caagttcgac | 840 |
| gtctacgatc tcgagctcac agaggtgaac tggaattcca cgctgaggag gctgctcatc | 900 |
| gggatgacca caggtccat cctcgtcatc gaggacatcg actgctccgt cgatctgcag | 960 |
| cagcgtgcag aggaaggtca ggatggtggt acaaaatcca gtcctcctcc ttcagaggac | 1020 |
| aaggtgacat tatctgggct actcaacttc gtggatggtc tgtggtcaac aagtggggag | 1080 |
| gagaggatca tcatcttcac gacgaactac aaggagcggc tcgacccggc gctgcttcgg | 1140 |
| ccaggcagga tggacatgca catccacatg ggttactgct gcccggagtc attcagaatc | 1200 |
| ctggcctcca actaccactc catcactgac cacgacacat accctgagat agaagcactg | 1260 |
| atcaaggagg cgatggtgac tccagcagag gtcgcggagg tgctcatgag gaacgacgac | 1320 |
| accgacatcg cgctccaggg ccttattcgg ttcctcaagg gaaagaaggg tgatgccaag | 1380 |
| aacagccaag gcgaaaacgt ggagcacgtg accaaagagg aggagaaaga gatgatgccg | 1440 |
| acaaaaaaag atgacccagt cgatcaaaat ctcaatgatg caggcaagca atga | 1494 |

<210> SEQ ID NO 81
<211> LENGTH: 497
<212> TYPE: PRT
<213> ORGANISM: Sorghum bicolor

<400> SEQUENCE: 81

Met Ala Thr Tyr Asp Lys Ala Met Glu Ser Tyr Lys Lys Ala Val Thr
1               5                   10                  15

Thr Val Ala Ser Leu Ala Ala Ser Ala Met Leu Val Arg Gly Val Val
            20                  25                  30

Asn Glu Leu Val Pro Tyr Glu Val Arg Glu Phe Leu Phe Ser Gly Leu
        35                  40                  45

Gly Tyr Leu Arg Ser Arg Met Ser Ser Gln His Thr Val Val Ile Glu
    50                  55                  60

Glu Thr Glu Gly Trp Ala Ser Asn Gln Leu Tyr Asp Ala Ala Arg Thr
65                  70                  75                  80

Tyr Leu Ala Thr Arg Ile Asn Thr Asp Met Gln Arg Leu Arg Val Ser
                85                  90                  95

Arg Val Asp Glu Gly Lys Ser Leu Met Phe Ser Met Glu Glu Gly Glu
            100                 105                 110

Glu Met Ala Asp Val His Ala Gly Ala Glu Phe Arg Trp Arg Leu Val
        115                 120                 125

Cys Arg Asp Gly Gly Ala Gly Ala Gly Asn Gly Gly His Ala His
    130                 135                 140

Ala His Ala Arg Gly Gly Gly Gly Gly Ser Tyr Arg Phe Glu Val
145                 150                 155                 160

Arg Ser Phe Glu Met Ser Phe His Arg Arg His Lys Asp Lys Ala Ile
                165                 170                 175

Ala Ser Tyr Leu Pro His Ile Leu Ala Glu Ala Lys Lys Ile Lys Asp
            180                 185                 190

Gln Asp Arg Thr Leu Lys Ile Tyr Met Asn Glu Gly Glu Ser Trp Phe
        195                 200                 205

Ala Ile Asp Leu His His Pro Ser Thr Phe Thr Thr Leu Ala Met Asp
    210                 215                 220

Arg Asp Met Lys Arg Ser Val Met Asp Asp Leu Glu Arg Phe Val Arg
225                 230                 235                 240

Arg Lys Glu Tyr Tyr Lys Arg Ile Gly Lys Ala Trp Lys Arg Gly Tyr
                245                 250                 255

Leu Leu His Gly Pro Pro Gly Thr Gly Lys Ser Ser Leu Ile Ala Ala
            260                 265                 270

Met Ala Asn Tyr Leu Lys Phe Asp Val Tyr Asp Leu Glu Leu Thr Glu
        275                 280                 285

Val Asn Trp Asn Ser Thr Leu Arg Arg Leu Leu Ile Gly Met Thr Asn
    290                 295                 300

Arg Ser Ile Leu Val Ile Glu Asp Ile Asp Cys Ser Val Asp Leu Gln
305                 310                 315                 320

Gln Arg Ala Glu Glu Gly Gln Asp Gly Gly Thr Lys Ser Ser Pro Pro
                325                 330                 335

Pro Ser Glu Asp Lys Val Thr Leu Ser Gly Leu Leu Asn Phe Val Asp
            340                 345                 350

Gly Leu Trp Ser Thr Ser Gly Glu Glu Arg Ile Ile Ile Phe Thr Thr
        355                 360                 365

Asn Tyr Lys Glu Arg Leu Asp Pro Ala Leu Leu Arg Pro Gly Arg Met
    370                 375                 380

| Asp | Met | His | Ile | His | Met | Gly | Tyr | Cys | Cys | Pro | Glu | Ser | Phe | Arg | Ile |
| 385 | | | | 390 | | | | | 395 | | | | | 400 | |

| Leu | Ala | Ser | Asn | Tyr | His | Ser | Ile | Thr | Asp | His | Asp | Thr | Tyr | Pro | Glu |
| | | | | 405 | | | | | 410 | | | | | 415 | |

| Ile | Glu | Ala | Leu | Ile | Lys | Glu | Ala | Met | Val | Thr | Pro | Ala | Glu | Val | Ala |
| | | | 420 | | | | | 425 | | | | | 430 | | |

| Glu | Val | Leu | Met | Arg | Asn | Asp | Asp | Thr | Asp | Ile | Ala | Leu | Gln | Gly | Leu |
| | | | 435 | | | | | 440 | | | | | 445 | | |

| Ile | Arg | Phe | Leu | Lys | Gly | Lys | Lys | Gly | Asp | Ala | Lys | Asn | Ser | Gln | Gly |
| | 450 | | | | | 455 | | | | | 460 | | | | |

| Glu | Asn | Val | Glu | His | Val | Thr | Lys | Glu | Glu | Lys | Glu | Met | Met | Pro |
| 465 | | | | | 470 | | | | | 475 | | | | | 480 |

| Thr | Lys | Lys | Asp | Asp | Pro | Val | Asp | Gln | Asn | Leu | Asn | Asp | Ala | Gly | Lys |
| | | | | 485 | | | | | 490 | | | | | 495 | |

Gln

<210> SEQ ID NO 82
<211> LENGTH: 1518
<212> TYPE: DNA
<213> ORGANISM: Arabidopsis thaliana

<400> SEQUENCE: 82

```
atgtttttct ctaaggatct tccttcacct acttcggttt tcacagctta cgcatcaatg     60
gcgggttaca tgatgatgat aagatcaatg gctcacgagc taatcccagc tcccctccaa    120
gatttcatct acaggactct ccggtctctc ttcttccgtt cttcttcctc cactttgacg    180
ctaaccatcg atgacgacaa catgggtatg aacaacgaga tctaccgagc tgctcagact    240
tatctctcca ccaagatcag tcctgatgca gtcaggctca gaataagtaa aggccataag    300
gataaacatg tcaacttgta tctcagcgac ggagaaatcg tcaacgatgt gtacgaagat    360
gtgcagctag tatggaggtt tgttactgac ggtggagaca agaaggagg cggcggagga     420
gtaggaggaa gaggaggagg aggaggaaga agaggtggta tggacgatga cggtaaaagc    480
gagtacttcg agctgagttt cgacaagaaa cataaagatt tgatattgaa ctcttatgtg    540
ccttacatcg agagtaaagc taagagata agagacgaga gaagaatctt gatgctgcat    600
tctctcaaca gtcttagatg ggaatcagtt attcttgaac cccttcgac ctttgagaca     660
atggctatgg aagatgatct caaacgtgac gtcatcgagg atcttgatcg gttcataaga    720
aggaaagagt tttacaagag agtagggaaa gcttggaaga ggggttactt gttgtacggt    780
ccaccgggta cggggaagtc tagtcttgtt gcagccatgg ctaattacct caagtttgat    840
gtttatgatc ttcagcttgc gagtgtgatg cgtgactctg atctaaggag gctcttacta    900
gctacacgta accggtcgat tcttgtcata gaagatatcg attgtgcagt ggatttaccc    960
aacagaattg agcagcctgt tgaaggcaag aaccgtggcg agtctcaggg accattgacg   1020
ttatcggggc tgctgaattt catagacgga ctatggtcaa gctgtggaga cgagcggatt   1080
ataatattca caacaaacca taaagatagg cttgacccgg cattgcttag accaggacgt   1140
atggatatgc acatttacat gggacattgc tcttttcaag gattcaagac tttagcttct   1200
aactacttgg gtttgagtga tgctgcgatg ccacaccgtc tatttccgga gattgagcgt   1260
ttgattgacg ggaagtaat gacgccggca caagtagcag aggagctgat gaagagtgag   1320
gatgctgacg tggcgctaga gggtttggtg aatgttttag agaaaatgag gctaaaatct   1380
aaggaatcga atccggtgat gatgaagcag aaagagagta gactggagat ggaggagatg   1440
```

```
agactaaaga gtgatactga gggttctccg aggaagaaca gcaaaagatt taagaagctt    1500
gtattgtttt ggacataa                                                 1518
```

<210> SEQ ID NO 83
<211> LENGTH: 505
<212> TYPE: PRT
<213> ORGANISM: Arabidopsis thaliana

<400> SEQUENCE: 83

```
Met Phe Phe Ser Lys Asp Leu Pro Ser Pro Thr Ser Val Phe Thr Ala
1               5                   10                  15

Tyr Ala Ser Met Ala Gly Tyr Met Met Met Ile Arg Ser Met Ala His
            20                  25                  30

Glu Leu Ile Pro Ala Pro Leu Gln Asp Phe Ile Tyr Arg Thr Leu Arg
        35                  40                  45

Ser Leu Phe Phe Arg Ser Ser Ser Ser Thr Leu Thr Leu Thr Ile Asp
    50                  55                  60

Asp Asp Asn Met Gly Met Asn Asn Glu Ile Tyr Arg Ala Ala Gln Thr
65                  70                  75                  80

Tyr Leu Ser Thr Lys Ile Ser Pro Asp Ala Val Arg Leu Arg Ile Ser
                85                  90                  95

Lys Gly His Lys Asp Lys His Val Asn Leu Tyr Leu Ser Asp Gly Glu
            100                 105                 110

Ile Val Asn Asp Val Tyr Glu Asp Val Gln Leu Val Trp Arg Phe Val
        115                 120                 125

Thr Asp Gly Gly Asp Lys Lys Gly Gly Gly Gly Val Gly Gly Arg
    130                 135                 140

Gly Gly Gly Gly Arg Arg Gly Gly Met Asp Asp Asp Gly Lys Ser
145                 150                 155                 160

Glu Tyr Phe Glu Leu Ser Phe Asp Lys Lys His Lys Asp Leu Ile Leu
                165                 170                 175

Asn Ser Tyr Val Pro Tyr Ile Glu Ser Lys Ala Lys Glu Ile Arg Asp
            180                 185                 190

Glu Arg Arg Ile Leu Met Leu His Ser Leu Asn Ser Leu Arg Trp Glu
        195                 200                 205

Ser Val Ile Leu Glu His Pro Ser Thr Phe Glu Thr Met Ala Met Glu
    210                 215                 220

Asp Asp Leu Lys Arg Asp Val Ile Glu Asp Leu Asp Arg Phe Ile Arg
225                 230                 235                 240

Arg Lys Glu Phe Tyr Lys Arg Val Gly Lys Ala Trp Lys Arg Gly Tyr
                245                 250                 255

Leu Leu Tyr Gly Pro Pro Gly Thr Gly Lys Ser Ser Leu Val Ala Ala
            260                 265                 270

Met Ala Asn Tyr Leu Lys Phe Asp Val Tyr Asp Leu Gln Leu Ala Ser
        275                 280                 285

Val Met Arg Asp Ser Asp Leu Arg Arg Leu Leu Ala Thr Arg Asn
    290                 295                 300

Arg Ser Ile Leu Val Ile Glu Asp Ile Asp Cys Ala Val Asp Leu Pro
305                 310                 315                 320

Asn Arg Ile Glu Gln Pro Val Glu Gly Lys Asn Arg Gly Glu Ser Gln
                325                 330                 335

Gly Pro Leu Thr Leu Ser Gly Leu Leu Asn Phe Ile Asp Gly Leu Trp
            340                 345                 350
```

```
Ser Ser Cys Gly Asp Glu Arg Ile Ile Phe Thr Thr Asn His Lys
        355                 360                 365

Asp Arg Leu Asp Pro Ala Leu Leu Arg Pro Gly Arg Met Asp Met His
370                 375                 380

Ile Tyr Met Gly His Cys Ser Phe Gln Gly Phe Lys Thr Leu Ala Ser
385                 390                 395                 400

Asn Tyr Leu Gly Leu Ser Asp Ala Ala Met Pro His Arg Leu Phe Pro
                405                 410                 415

Glu Ile Glu Arg Leu Ile Asp Gly Val Met Thr Pro Ala Gln Val
                420                 425                 430

Ala Glu Glu Leu Met Lys Ser Glu Asp Ala Asp Val Ala Leu Glu Gly
        435                 440                 445

Leu Val Asn Val Leu Glu Lys Met Arg Leu Lys Ser Lys Glu Ser Asn
        450                 455                 460

Pro Val Met Met Lys Gln Lys Glu Ser Arg Leu Glu Met Glu Glu Met
465                 470                 475                 480

Arg Leu Lys Ser Asp Thr Glu Gly Ser Pro Arg Lys Asn Ser Lys Arg
                485                 490                 495

Phe Lys Lys Leu Val Leu Phe Trp Thr
                500                 505

<210> SEQ ID NO 84
<211> LENGTH: 1497
<212> TYPE: DNA
<213> ORGANISM: Glycine max

<400> SEQUENCE: 84
atgtccttct tttcctcctc caacctggcc accgccaaga cggtgctctc ggcggcggcc      60
tcggtggctg ccaccgcaat ggtggtccgc tccgtggcga cgacctcct tccgtcggag      120 ctccggtcct acatcaccaa cggcatccac agcatgttct ggcgcttctc ctccgagata     180
accctggtca tcgacgagtt cgacggcctc tcaacaacc aaatctacga ggccgccgaa      240
acctacctcg cgccaaaat ctctcccaac acacgcagac ttaaagtcag caagcccgag      300
acagacacaa ccttcgccct cacaatggag cgcaacgagt ccttaaccga cgttttcaga     360
agcatgaaat ttaactgggt tctcgtctgc cgtcaggtcg agtccagagg cttccacaac     420
cctcgcgacc tcaacgccac catgaaatcc gaggttcgct ccctcgaact cactttttaac   480 aagaagcata agacatggt gctccaaacc tatcttccct atatcctcaa cgaagccaag     540
tccatgaaac aagctacaaa agcgcttaag atcttcacag tcgactacca gaacatgtac    600
ggcaacatca gcgacgcgtg ggtggggatg aagctggacc atcccgccac gttcgacacg   660
ctggcgatgg agcgtggcgc gaaggagttt gtcatgaggg acttggagag gttcgtaaag   720
aggaaggagt attataggag agttgggaag gcgtggaaga gagggtattt gctgtatggt    780
cctcccggca ccgggaaatc gagcttgatt gctgccatgg cgaattactt gaagtttgat    840
gtgtatgatt tggagctgac ggagctgaat gctaactcgg agctcaggag gttgctcatt    900
gcaatggcga ataggtccat tcttgttgtg gaggacattg attgcactgt tgagtttcat   960
gatcggagag ctgaggccag agctgcttct ggacataaca acgacagaca ggttacacta    1020
tcgggtttgc ttaatttcat tgatgggtta tggtcaagtt gtggggatga ggatcata      1080 gtgttcacaa caaccacaa ggacaagctt gaccctgcat tgctgcgccc tggtcgaatg    1140
gatgttcaca ttcacatgtc ctattgcact ccctgtggtt tcaggcagct agcttccaat   1200
tacctcggaa tcaaagagca ttctctcttc gaaaagatcg aggaagagat gcagaaaacc    1260
```

```
caggtgactc ctgctgaggt agcagaacag cttctgaaga gcagccacat cgaaactagc    1320
ctcgaacagc ttatagattt catgagaaag aagaaagaaa ctcagaaatt ggaggctaaa    1380
aagaaggaac aagaggccaa agaggaacag cagaggaagg aaattgatga tggtggtaaa    1440
ggagaaaaag ttgacagtga tgataacaat aatgaaagaa aagtattac tacctag       1497
```

<210> SEQ ID NO 85
<211> LENGTH: 498
<212> TYPE: PRT
<213> ORGANISM: Glycine max

<400> SEQUENCE: 85

```
Met Ser Phe Phe Ser Ser Asn Leu Ala Thr Ala Lys Thr Val Leu
1               5                   10                  15

Ser Ala Ala Ala Ser Val Ala Ala Thr Ala Met Val Val Arg Ser Val
                20                  25                  30

Ala Ser Asp Leu Leu Pro Ser Glu Leu Arg Ser Tyr Ile Thr Asn Gly
            35                  40                  45

Ile His Ser Met Phe Trp Arg Phe Ser Ser Glu Ile Thr Leu Val Ile
        50                  55                  60

Asp Glu Phe Asp Gly Leu Leu Asn Asn Gln Ile Tyr Glu Ala Ala Glu
65                  70                  75                  80

Thr Tyr Leu Gly Ala Lys Ile Ser Pro Asn Thr Arg Arg Leu Lys Val
                85                  90                  95

Ser Lys Pro Glu Thr Asp Thr Thr Phe Ala Leu Thr Met Glu Arg Asn
            100                 105                 110

Glu Ser Leu Thr Asp Val Phe Arg Ser Met Lys Phe Asn Trp Val Leu
        115                 120                 125

Val Cys Arg Gln Val Glu Ser Arg Gly Phe His Asn Pro Arg Asp Leu
130                 135                 140

Asn Ala Thr Met Lys Ser Glu Val Arg Ser Leu Glu Leu Thr Phe Asn
145                 150                 155                 160

Lys Lys His Lys Asp Met Val Leu Gln Thr Tyr Leu Pro Tyr Ile Leu
                165                 170                 175

Asn Glu Ala Lys Ser Met Lys Gln Ala Thr Lys Ala Leu Lys Ile Phe
            180                 185                 190

Thr Val Asp Tyr Gln Asn Met Tyr Gly Asn Ile Ser Asp Ala Trp Val
        195                 200                 205

Gly Met Lys Leu Asp His Pro Ala Thr Phe Asp Thr Leu Ala Met Glu
210                 215                 220

Arg Gly Ala Lys Glu Phe Val Met Arg Asp Leu Glu Arg Phe Val Lys
225                 230                 235                 240

Arg Lys Glu Tyr Tyr Arg Arg Val Gly Lys Ala Trp Lys Arg Gly Tyr
                245                 250                 255

Leu Leu Tyr Gly Pro Pro Gly Thr Gly Lys Ser Ser Leu Ile Ala Ala
            260                 265                 270

Met Ala Asn Tyr Leu Lys Phe Asp Val Tyr Asp Leu Glu Leu Thr Glu
        275                 280                 285

Leu Asn Ala Asn Ser Glu Leu Arg Arg Leu Leu Ile Ala Met Ala Asn
        290                 295                 300

Arg Ser Ile Leu Val Val Glu Asp Ile Asp Cys Thr Val Glu Phe His
305                 310                 315                 320

Asp Arg Arg Ala Glu Ala Arg Ala Ala Ser Gly His Asn Asn Asp Arg
                325                 330                 335
```

Gln Val Thr Leu Ser Gly Leu Leu Asn Phe Ile Asp Gly Leu Trp Ser
        340                 345                 350

Ser Cys Gly Asp Glu Arg Ile Ile Val Phe Thr Thr Asn His Lys Asp
            355                 360                 365

Lys Leu Asp Pro Ala Leu Leu Arg Pro Gly Arg Met Asp Val His Ile
    370                 375                 380

His Met Ser Tyr Cys Thr Pro Cys Gly Phe Arg Gln Leu Ala Ser Asn
385                 390                 395                 400

Tyr Leu Gly Ile Lys Glu His Ser Leu Phe Glu Lys Ile Glu Glu Glu
                405                 410                 415

Met Gln Lys Thr Gln Val Thr Pro Ala Glu Val Ala Glu Gln Leu Leu
            420                 425                 430

Lys Ser Ser His Ile Glu Thr Ser Leu Glu Gln Leu Ile Asp Phe Met
        435                 440                 445

Arg Lys Lys Lys Glu Thr Gln Lys Leu Glu Ala Lys Lys Lys Glu Gln
    450                 455                 460

Glu Ala Lys Glu Gln Gln Arg Lys Glu Ile Asp Asp Gly Gly Lys
465                 470                 475                 480

Gly Glu Lys Val Asp Ser Asp Asp Asn Asn Glu Lys Lys Ser Ile
                485                 490                 495

Thr Thr

<210> SEQ ID NO 86
<211> LENGTH: 2079
<212> TYPE: DNA
<213> ORGANISM: Oryza sativa

<400> SEQUENCE: 86

| | | | | | |
|---|---|---|---|---|---|
| atgtcggagg | cggaccggat | acgggtgcgc | gcggcggcgc | tggcgctgga | cggcggcggc | 60 |
| ggcggcgcgg | tgcgggacaa | gccggacgcg | aaggcggacg | tgttcgccga | tcttggctcg | 120 |
| ccggtgtccc | cgctgcgggc | gcgggcgagc | gtggcgacgt | cgtcgtcgtc | gtcgtccggg | 180 |
| tcggctaagt | cgccggcgcc | gtcgaatgcc | ggggcgctgg | cgctggcggg | cgggaggagc | 240 |
| cactccggcg | agctgacggc | ggagagcacg | ccccgcgcg | tgcccgggca | ccggcggtgc | 300 |
| ggatctggcc | cgttgatatt | ctccggtggg | agcagcggcg | ggagcggcgg | cggcggcggg | 360 |
| gaccgcggga | gcacggcgag | ctcgccgatg | actaatgcgc | tccccgcagg | taacatctgc | 420 |
| ccgtccgggc | gcgtccccgt | cgcggcggcc | gcgccgcccc | cgccgcgctc | ccgcccggac | 480 |
| gtgctcggat | ccggcaccgg | caactacggc | cacgggagca | tcatgcgcgg | cggcggcggc | 540 |
| atggccccg | cgaggagcag | cattgactcc | tcgtcgtttc | ttggacacgc | tccgagatct | 600 |
| ccggcgacct | tccggcggc | gtcgtcggcg | agcagcggga | gcctccagga | tgtgaccccgc | 660 |
| ctgggcaacg | agtggtacaa | gaagggcaag | cacgccgagg | cgctgcggca | ctacgaccgc | 720 |
| gccgtggccc | tctgccccga | gagcgccgcg | tgccgcggga | accgccgcc | cgcgctcgcc | 780 |
| ggcctcggcc | gcctcgccga | cgcgctccgc | gactgcgagg | aggcagtccg | cctcgatccg | 840 |
| gccaacggcc | gcgcccacag | ccgcctcgcc | ggcctctgcc | tccggttggg | gatgattagc | 900 |
| aaggcgagga | ggcacttaac | gcaggctggg | catctccatc | aatctgatcc | ttcggagtgg | 960 |
| gagaagctgc | aggaggtgga | gatgcatcag | ggaagaagca | tagatgccag | gaaagtcggg | 1020 |
| gattggaaga | gcgcgctgag | ggaagctgat | gctgccattg | ctgctggagc | tgactcctct | 1080 |
| cggctgcttc | ttgcgataag | gtcagaagca | cttctccgtc | tccacaagtt | ggaggaggct | 1140 |

```
gactcgactc ttgcaagttt gctgaaattg acagcgtgt tgctgtatcg gatgggagcc   1200
aacccgtcag gcatgctagc tgagtcatat gtctctattg tccgagccca agtcgacatg   1260
gcattgggaa ggtttgatgc tgctgtggag gcagctgata atgctagatt tattgatcct   1320
ggaaatgcgg aagttggaat gattctaaat aatgtcaaat tagttgcaaa ggctcgagcc   1380
caaggaaatg agctctataa agctgccaag ttttctgatg catctatagc atatagtgaa   1440
gggctcaaat atgagccctc aaatccagtg ctctattgca atcgagcagc atgctgggg    1500 aagctagagc ggtgggaaaa ggctgttgat gactgtaacg aagcattaag aatacaacct   1560
aattacacaa aggcgctttt aaggcgagct tcatcctatg ccaagctcga gcgttgggct   1620
gattgtgtgc gggactatga ggtgcttcat aaagagcttc ctgctgatac agaggttgca   1680
gaagcactgt tccatgctca agttgcattg aagacaactc gtggtgagga tgtatcgaat   1740
atgaaatttg aggagaggt tgagatggta accagtgtag aacaactccg tgctgccata   1800
ggatcaccag gggtgtctgt tgtttacttc atgtcaatca tgaatcagca gtgcacacta   1860
attacacctt cggtgaactc cctttgcagc gaatgcccct cgctgaattt cctaaaggta   1920
aatgttgaag atagccctat ggtcgcgaag gcggagaacg tgcggatagt cccaacattc   1980
aagatataca aagatggggt gaaggtgaag gaaatgatct gcccaagctt gcatgttctg   2040
cgctactcag taaggcacta tgccgtatct agttcttga                         2079
```

<210> SEQ ID NO 87
<211> LENGTH: 692
<212> TYPE: PRT
<213> ORGANISM: Oryza sativa

<400> SEQUENCE: 87

```
Met Ser Glu Ala Asp Arg Ile Arg Val Arg Ala Ala Leu Ala Leu
1               5                   10                  15

Asp Gly Gly Gly Gly Ala Val Arg Asp Lys Pro Asp Ala Lys Ala
                20                  25                  30

Asp Val Phe Ala Asp Leu Gly Ser Pro Val Ser Pro Leu Arg Ala Arg
                35                  40                  45

Ala Ser Val Ala Thr Ser Ser Ser Ser Gly Ser Ala Lys Ser
        50                  55                  60

Pro Ala Pro Ser Asn Ala Gly Ala Leu Ala Leu Ala Gly Gly Arg Ser
65                  70                  75                  80

His Ser Gly Glu Leu Thr Ala Glu Ser Thr Pro Pro Arg Leu Pro Gly
                85                  90                  95

His Arg Arg Cys Gly Ser Gly Pro Leu Ile Phe Ser Gly Ser Ser
                100                 105                 110

Gly Gly Ser Gly Gly Gly Gly Asp Arg Gly Ser Thr Ala Ser Ser
            115                 120                 125

Pro Met Thr Asn Ala Leu Pro Ala Gly Asn Ile Cys Pro Ser Gly Arg
        130                 135                 140

Val Pro Val Ala Ala Ala Pro Pro Pro Arg Ser Arg Pro Asp
145                 150                 155                 160

Val Leu Gly Ser Gly Thr Gly Asn Tyr Gly His Gly Ser Ile Met Arg
                165                 170                 175

Gly Gly Gly Gly Met Ala Pro Ala Arg Ser Ser Ile Asp Ser Ser Ser
            180                 185                 190

Phe Leu Gly His Ala Pro Arg Ser Pro Ala Thr Phe Pro Ala Ala Ser
        195                 200                 205
```

```
Ser Ala Ser Ser Gly Ser Leu Gln Asp Val Thr Arg Leu Gly Asn Glu
    210             215                 220

Trp Tyr Lys Lys Gly Lys His Ala Glu Ala Leu Arg His Tyr Asp Arg
225             230                 235                 240

Ala Val Ala Leu Cys Pro Glu Ser Ala Ala Cys Arg Gly Asn Arg Ala
                245                 250                 255

Ala Ala Leu Ala Gly Leu Gly Arg Leu Ala Asp Ala Leu Arg Asp Cys
            260                 265                 270

Glu Glu Ala Val Arg Leu Asp Pro Ala Asn Gly Arg Ala His Ser Arg
                275                 280                 285

Leu Ala Gly Leu Cys Leu Arg Leu Gly Met Ile Ser Lys Ala Arg Arg
    290                 295                 300

His Leu Thr Gln Ala Gly His Leu His Gln Ser Asp Pro Ser Glu Trp
305                 310                 315                 320

Glu Lys Leu Gln Glu Val Glu Met His Gln Gly Arg Ser Ile Asp Ala
                325                 330                 335

Arg Lys Val Gly Asp Trp Lys Ser Ala Leu Arg Glu Ala Asp Ala Ala
            340                 345                 350

Ile Ala Ala Gly Ala Asp Ser Ser Arg Leu Leu Ala Ile Arg Ser
            355                 360                 365

Glu Ala Leu Leu Arg Leu His Lys Leu Glu Glu Ala Asp Ser Thr Leu
    370                 375                 380

Ala Ser Leu Leu Lys Leu Asp Ser Val Leu Leu Tyr Arg Met Gly Ala
385                 390                 395                 400

Asn Pro Ser Gly Met Leu Ala Glu Ser Tyr Val Ser Ile Val Arg Ala
                405                 410                 415

Gln Val Asp Met Ala Leu Gly Arg Phe Asp Ala Ala Val Glu Ala Ala
            420                 425                 430

Asp Asn Ala Arg Phe Ile Asp Pro Gly Asn Ala Glu Val Gly Met Ile
            435                 440                 445

Leu Asn Asn Val Lys Leu Val Ala Lys Ala Arg Ala Gln Gly Asn Glu
    450                 455                 460

Leu Tyr Lys Ala Ala Lys Phe Ser Asp Ala Ser Ile Ala Tyr Ser Glu
465                 470                 475                 480

Gly Leu Lys Tyr Glu Pro Ser Asn Pro Val Leu Tyr Cys Asn Arg Ala
                485                 490                 495

Ala Cys Trp Gly Lys Leu Glu Arg Trp Glu Lys Ala Val Asp Asp Cys
            500                 505                 510

Asn Glu Ala Leu Arg Ile Gln Pro Asn Tyr Thr Lys Ala Leu Leu Arg
    515                 520                 525

Arg Ala Ser Ser Tyr Ala Lys Leu Glu Arg Trp Ala Asp Cys Val Arg
    530                 535                 540

Asp Tyr Glu Val Leu His Lys Glu Leu Pro Ala Asp Thr Glu Val Ala
545                 550                 555                 560

Glu Ala Leu Phe His Ala Gln Val Ala Leu Lys Thr Thr Arg Gly Glu
                565                 570                 575

Asp Val Ser Asn Met Lys Phe Gly Gly Glu Val Glu Met Val Thr Ser
            580                 585                 590

Val Glu Gln Leu Arg Ala Ala Ile Gly Ser Pro Gly Val Ser Val Val
                595                 600                 605

Tyr Phe Met Ser Ile Met Asn Gln Gln Cys Thr Leu Ile Thr Pro Ser
    610                 615                 620

Val Asn Ser Leu Cys Ser Glu Cys Pro Ser Leu Asn Phe Leu Lys Val
```

625           630           635           640

Asn Val Glu Asp Ser Pro Met Val Ala Lys Ala Glu Asn Val Arg Ile
                    645                 650                 655

Val Pro Thr Phe Lys Ile Tyr Lys Asp Gly Val Lys Val Lys Glu Met
                660                 665                 670

Ile Cys Pro Ser Leu His Val Leu Arg Tyr Ser Val Arg His Tyr Ala
            675                 680                 685

Val Ser Ser Ser
        690

<210> SEQ ID NO 88
<211> LENGTH: 828
<212> TYPE: DNA
<213> ORGANISM: Zea mays

<400> SEQUENCE: 88

```
atgaagcaat cctccaacga atccgcgggc gcagacgttt cccgtgcgca atcggtgaag     60
agccgcatcg ccaggagcaa cgacgcgcgc aggctcaaga actggatcac ggtgctccag    120
gaagcgcagg ccgccgtggc cgacggcgcc gactgtgctc cgcaggtgat ggcgttgcaa    180
gccgaggcgt tgctgaggct gcaacggcac gacgaagccg actcgcttct cagcggcgcc    240
ggcgcgccaa ggttcggggt cgacgagtcg accaagttct tcggcacctt cggccacgcc    300
tacttcctca tcgtgcgagc tcaggtcgac atggctgctg aaggttcga ggacgcggtg     360
gcgacggcgc agacggcgtt tcagctggac ccaagcaacc gggaggtctc ggtcgttcag    420
aggagggcca aggcggcggc cgcggcgcgg ctgcgtggca acgacctctt caaggccgcc    480
aagttcgcgg aggcgtgcgc cgcgtacggc gagggcctcg acagggagcc cggcaacgcc    540
gtgctgctct gcaaccgcgc ggcgtgccac gccaagctcg gcggcacga aaggccgtc     600
gaggactgca gcgccgcgct cgacgtgcgc ccctcgtaca gcaaggcgcg gctcaggagg    660
gcggactgca acgtcaagct ggagaggtgg aagcgtcct tgagagatta ccaggtgctg     720
gtccaagaac tgccggagaa tgaggacgtg aagaaggctc tctctgaggt cgaagccaag    780
ctcaagggcc aaaggcatgg ggccgcagca gccagatctc agcactga                828
```

<210> SEQ ID NO 89
<211> LENGTH: 275
<212> TYPE: PRT
<213> ORGANISM: Zea mays

<400> SEQUENCE: 89

Met Lys Gln Ser Ser Asn Glu Ser Ala Gly Ala Asp Val Ser Arg Ala
1               5                   10                  15

Gln Ser Val Lys Ser Arg Ile Ala Arg Ser Asn Asp Ala Arg Arg Leu
            20                  25                  30

Lys Asn Trp Ile Thr Val Leu Gln Glu Ala Gln Ala Val Ala Asp
        35                  40                  45

Gly Ala Asp Cys Ala Pro Gln Val Met Ala Leu Gln Ala Glu Ala Leu
    50                  55                  60

Leu Arg Leu Gln Arg His Asp Glu Ala Asp Ser Leu Ser Gly Ala
65                  70                  75                  80

Gly Ala Pro Arg Phe Gly Val Asp Glu Ser Thr Lys Phe Phe Gly Thr
                85                  90                  95

Phe Gly His Ala Tyr Phe Leu Ile Val Arg Ala Gln Val Asp Met Ala
            100                 105                 110

```
Ala Gly Arg Phe Glu Asp Ala Val Ala Thr Ala Gln Thr Ala Phe Gln
            115                 120                 125

Leu Asp Pro Ser Asn Arg Glu Val Ser Val Val Gln Arg Arg Ala Lys
        130                 135                 140

Ala Ala Ala Ala Ala Arg Leu Arg Gly Asn Asp Leu Phe Lys Ala Ala
145                 150                 155                 160

Lys Phe Ala Glu Ala Cys Ala Ala Tyr Gly Glu Gly Leu Asp Arg Glu
                165                 170                 175

Pro Gly Asn Ala Val Leu Leu Cys Asn Arg Ala Ala Cys His Ala Lys
            180                 185                 190

Leu Gly Arg His Glu Lys Ala Val Glu Asp Cys Ser Ala Ala Leu Asp
        195                 200                 205

Val Arg Pro Ser Tyr Ser Lys Ala Arg Leu Arg Arg Ala Asp Cys Asn
    210                 215                 220

Val Lys Leu Glu Arg Trp Glu Ala Ser Leu Arg Asp Tyr Gln Val Leu
225                 230                 235                 240

Val Gln Glu Leu Pro Glu Asn Glu Asp Val Lys Lys Ala Leu Ser Glu
                245                 250                 255

Val Glu Ala Lys Leu Lys Gly Gln Arg His Gly Ala Ala Ala Ala Arg
            260                 265                 270

Ser Gln His
        275

<210> SEQ ID NO 90
<211> LENGTH: 1764
<212> TYPE: DNA
<213> ORGANISM: Sorghum bicolor

<400> SEQUENCE: 90
atgacggagc cgcgcgaccc gccgccgccg accggctgcg ccatgttcgg catctacagc      60
ggcatgttcc gccgccgccg atccgcatcc atgacctccc tccaccggat caacggggca     120
tcctcgcccg ccgaggccga ggccgcggcg ccggcgaacc cggcgcatca tcggaagccc     180
ggcgtgctcc acgactcctc ctccctcgtg cgccgcccca cgccatgcc cgtgccggcg      240 ccggcgcaga acggcgccgt ctcccgcgcc gcgccaccgg cggcgaacga taggagtagg     300
ccggccacca aggtggcgaa cggcggcgtc ggcggcccga acccgccgt ggagccggcg      360 gcggagtaca ccggcatggc cgcggagctg gacaagatga tcctcgacca ccagagggtc     420
aagggcacca cgcagctggt gcgcgccacg tccggcaaca tgatgctgca ccgcaaccct     480
ggcaacctca acgcgggggg cggcgcgccg gcgcgcaact ccgtggagcg cggcgccaag     540
gcggcgaacg agcggaaggc ccccaacggg tacgcgttct cgggaatggg gaacatcgtc     600
aaggagccca ggccggcggc gggggggcagc gagctgtgcc gggcgctgtc gcaccgcacg     660
gatcccgaga agctcaagga gatgggcaac gaggagtacc ggcaggggca ttacacggag     720
gcggtggcgc tctacgacca ggccatcatg atggacgcca gcggccggc gtactggagc     780 aacaaggcgg ccgcgctcgc cgcgctcgga cggctcatcg aggccgtcgg cgactgcaag     840
gaggccgtgc ggatcgaccc tgcgtacgat cgcgctcacc accggcttgg cggcttgtac     900
ctcagattag gagaacctga caaagccatc taccacttga gcaatcttg caatgaatcc     960 gcggggcgcag acgttgctcg tgcgcagtcg gtgaagagcc gcatcgccaa gagcagcgac    1020
gcgcgcaggc tcaagaactg gatcacggtg ctccaggaag cgcaggccgc cgtgtccgac    1080
ggcgccgact gcgctccaca ggtgatggcg ttgcaagccg aggcgttgct gaggctgcag    1140
```

-continued

```
cggcacgacg acgcggactc gcttctcagc agcgccgccg cgccaaggtt cggcgtcgac    1200
gagtcgacca agttcttcgg caccttcggc cacgcctact tcctcatcgt gcgagctcag    1260
gtcgacatgg ctgctggaag gttcgaggac gcggtggcga cggcgcagac ggcgtttcag    1320
ctggacccga gcaaccggga ggtgacggtc gtgcagagga gggccaaggc ggcggccgcg    1380
gcgcggctgc gtggcaacga cctcttcaag gccgccaagt tcgtggaggc gtgcgccgcc    1440
tacggcgagg gcctcgacag ggagcccagc aacgccgtgc tgctctgcaa ccgcgccgcg    1500
tgccacgcca agctcgggcg cacgagaag gccgtcgagg actgcagcgc cgcgctcgcc    1560
gtgcgcccct cgtacagcaa ggcgcggctc aggagggcgg actgcaacgt caagctggag    1620
aggtgggaag cgtccttgag agactaccag gtgctgatcc aagaactgcc ggagaacgag    1680
gacgtgaaga gtctctttc tgaggtcgaa gccaagctca agagccaaag gaatggcggc    1740
gcagcagcca gatctcagca ctga                                          1764
```

<210> SEQ ID NO 91
<211> LENGTH: 587
<212> TYPE: PRT
<213> ORGANISM: Sorghum bicolor

<400> SEQUENCE: 91

```
Met Thr Glu Pro Arg Asp Pro Pro Pro Thr Gly Cys Ala Met Phe
1               5                   10                  15

Gly Ile Tyr Ser Gly Met Phe Arg Arg Arg Ser Ala Ser Met Thr
                20                  25                  30

Ser Leu His Arg Ile Asn Gly Ala Ser Ser Pro Ala Glu Ala Glu Ala
                35                  40                  45

Ala Ala Pro Ala Asn Pro Ala His His Arg Lys Pro Gly Val Leu His
        50                  55                  60

Asp Ser Ser Ser Leu Val Arg Arg Pro Asn Ala Met Pro Val Pro Ala
65                  70                  75                  80

Pro Ala Gln Asn Gly Ala Val Ser Arg Ala Ala Pro Ala Ala Asn
                85                  90                  95

Asp Arg Ser Arg Pro Ala Thr Lys Val Ala Asn Gly Val Gly Gly
            100                 105                 110

Pro Arg Pro Ala Val Glu Pro Ala Ala Glu Tyr Thr Gly Met Ala Ala
        115                 120                 125

Glu Leu Asp Lys Met Ile Leu Asp His Gln Arg Val Lys Gly Thr Thr
    130                 135                 140

Gln Leu Val Arg Ala Thr Ser Gly Asn Met Met Leu His Arg Asn Leu
145                 150                 155                 160

Gly Asn Leu Asn Ala Gly Gly Gly Ala Pro Ala Arg Asn Ser Val Glu
                165                 170                 175

Arg Gly Ala Lys Ala Ala Asn Glu Arg Lys Ala Pro Asn Gly Tyr Ala
            180                 185                 190

Phe Ser Gly Met Gly Asn Ile Val Lys Glu Pro Arg Pro Ala Ala Gly
        195                 200                 205

Gly Ser Glu Leu Cys Arg Ala Leu Ser His Arg Thr Asp Pro Glu Lys
    210                 215                 220

Leu Lys Glu Met Gly Asn Glu Glu Tyr Arg Gln Gly His Tyr Thr Glu
225                 230                 235                 240

Ala Val Ala Leu Tyr Asp Gln Ala Ile Met Met Asp Ala Arg Arg Pro
                245                 250                 255

Ala Tyr Trp Ser Asn Lys Ala Ala Ala Leu Ala Ala Leu Gly Arg Leu
```

```
            260                 265                 270
Ile Glu Ala Val Gly Asp Cys Lys Glu Ala Val Arg Ile Asp Pro Ala
            275                 280                 285

Tyr Asp Arg Ala His His Arg Leu Gly Gly Leu Tyr Leu Arg Leu Gly
            290                 295                 300

Glu Pro Asp Lys Ala Ile Tyr His Leu Lys Gln Ser Cys Asn Glu Ser
305                 310                 315                 320

Ala Gly Ala Asp Val Ala Arg Ala Gln Ser Val Lys Ser Arg Ile Ala
                325                 330                 335

Lys Ser Ser Asp Ala Arg Arg Leu Lys Asn Trp Ile Thr Val Leu Gln
            340                 345                 350

Glu Ala Gln Ala Ala Val Ser Asp Gly Ala Asp Cys Ala Pro Gln Val
            355                 360                 365

Met Ala Leu Gln Ala Glu Ala Leu Leu Arg Leu Gln Arg His Asp Asp
            370                 375                 380

Ala Asp Ser Leu Leu Ser Ser Ala Ala Ala Pro Arg Phe Gly Val Asp
385                 390                 395                 400

Glu Ser Thr Lys Phe Phe Gly Thr Phe Gly His Ala Tyr Phe Leu Ile
                405                 410                 415

Val Arg Ala Gln Val Asp Met Ala Ala Gly Arg Phe Glu Asp Ala Val
                420                 425                 430

Ala Thr Ala Gln Thr Ala Phe Gln Leu Asp Pro Ser Asn Arg Glu Val
            435                 440                 445

Thr Val Val Gln Arg Arg Ala Lys Ala Ala Ala Ala Arg Leu Arg
            450                 455                 460

Gly Asn Asp Leu Phe Lys Ala Lys Phe Val Glu Ala Cys Ala Ala
465                 470                 475                 480

Tyr Gly Glu Gly Leu Asp Arg Glu Pro Ser Asn Ala Val Leu Leu Cys
                485                 490                 495

Asn Arg Ala Ala Cys His Ala Lys Leu Gly Arg His Glu Lys Ala Val
                500                 505                 510

Glu Asp Cys Ser Ala Ala Leu Ala Val Arg Pro Ser Tyr Ser Lys Ala
            515                 520                 525

Arg Leu Arg Arg Ala Asp Cys Asn Val Lys Leu Glu Arg Trp Glu Ala
            530                 535                 540

Ser Leu Arg Asp Tyr Gln Val Leu Ile Gln Glu Leu Pro Glu Asn Glu
545                 550                 555                 560

Asp Val Lys Lys Ser Leu Ser Glu Val Glu Ala Lys Leu Lys Ser Gln
                565                 570                 575

Arg Asn Gly Gly Ala Ala Ala Arg Ser Gln His
            580                 585

<210> SEQ ID NO 92
<211> LENGTH: 1782
<212> TYPE: DNA
<213> ORGANISM: Arabidopsis thaliana

<400> SEQUENCE: 92
atggaggaga acacggcggt ggctgcggcg gagagaagat caggttgtgg tttattgagt      60
gtaatgtttg gtagacgtgg cttgtggtcc aagaaatcta ccgctgtcga taacggtagc     120
cagaaaagca catctacggc tgcgaccgca acaagcaaca ttcaattcac taaatctccg     180
ggcaccgagt taagaagcc gcgtgatgat cagaaagttt ccgctgagcc aatccagaat      240
aacaagatcc agaacaacca aaatcacaac cagagatccg tagttccatc aaaaccctcg     300
```

```
tcaaatcagt accctaataa ccatcaatta gggacttacg agaatcacca acgaagtagt    360
tataacaaca atagtaatag tgttgatcca tatcgaggag gaggaggaca gaggaaagtg    420
ccaagagaag ccattggttt atcgggtgag cttgaaagca tgatcacgga tcatcagaaa    480
gcaaaaggaa ccaatggatt ggttcgtgca tcttctagca atataatgtt atatggtaat    540
cttggcaatt tgaatcagac tggacctgta actgcgggtg taaattacgg taataacaat    600
ggatatggcg tgaagaggac gacaatgggg gctgcaacgg cgacgacaac aaagagtcaa    660
gatcaatcag gatctttgtg tagagcaatc tcaacaagaa tggatccgga aactttgaag    720
atcatgggga atgaagatta caagaatggg aatttcgcag aggctttagc attgtatgat    780
gcagccattg caattgatcc aaacaaagct gcttaccgta gcaacaagag cgcggctttg    840
accgccctag ggagaatcct tgacgcggtt tttgaatgca gagaagcaat cagaattgag    900
cctcattacc acagagcaca tcataggttg ggtaacttgt acctcaggtt aggagaagtg    960
gagaaatcga tatatcattt caaacattcg ggtcccgaag ctgatcgtga agacattgca   1020
aaggcgaaaa cggtacagac acatctcaac aaatgcacag aagctaagag attacgagat   1080
tggaatggtt tgattacgga gacaacaaac acaatctctt caggagctga tgcagcccct   1140
caggtctatg cattgcaagc agaagctttg ttgaagacac atagacatca agaagctgat   1200
gatgctttgt ctagatgtcc ggttttcgat attgatgcta gtactaggta ctacggaccg   1260
gtcggttatg ctggtttctt ggtcgtccgt gctcaggttc acttagcgtc tggcagattc   1320
gacgaggcgg tggaggcgat ccaacgcgcc gggaagctgg acgggaataa ccgagaggtg   1380
attatgattt cacgacgggc acaagcggtg actgaagctc ggtttaaagg aaacgagctg   1440
tttaaatctg gacggttcca agaggcgtgc gccgcttatg gtgagggatt agatcacgat   1500
ccacgaaact ctgttttgct ctgtaaccgc gcggcttgtc ggtcaaaatt gggtcaattt   1560
gataaatcta tagaggattg cacggcggct ctctccgtcc ggccgggata tggtaaggct   1620
cgcctcagaa gagccgattg taacgccaag atcgaaaagt gggaattagc ggtgggtgac   1680
tacgagatat tgaaaaagga gtcgccggag gatgagcaag ttatcagagg attatcagag   1740
gctcaacaac aactcatgaa acgtagtgga caagactctt ga                     1782

<210> SEQ ID NO 93
<211> LENGTH: 593
<212> TYPE: PRT
<213> ORGANISM: Arabidopsis thaliana

<400> SEQUENCE: 93

Met Glu Glu Asn Thr Ala Val Ala Ala Ala Glu Arg Arg Ser Gly Cys
1               5                   10                  15

Gly Leu Leu Ser Val Met Phe Gly Arg Arg Gly Leu Trp Ser Lys Lys
            20                  25                  30

Ser Thr Ala Val Asp Asn Gly Ser Gln Lys Ser Thr Ser Thr Ala Ala
        35                  40                  45

Thr Ala Thr Ser Asn Ile Gln Phe Thr Lys Ser Pro Gly Thr Glu Leu
    50                  55                  60

Lys Lys Pro Arg Asp Asp Gln Lys Val Ser Ala Glu Pro Ile Gln Asn
65                  70                  75                  80

Asn Lys Ile Gln Asn Asn Gln Asn His Asn Gln Arg Ser Val Val Pro
                85                  90                  95

Ser Lys Pro Ser Ser Asn Gln Tyr Pro Asn Asn His Gln Leu Gly Thr
            100                 105                 110
```

```
Tyr Glu Asn His Gln Arg Ser Ser Tyr Asn Asn Ser Asn Ser Val
        115                 120                 125

Asp Pro Tyr Arg Gly Gly Gly Gln Arg Lys Val Pro Arg Glu Ala
    130                 135                 140

Ile Gly Leu Ser Gly Glu Leu Glu Ser Met Ile Thr Asp His Gln Lys
145                 150                 155                 160

Ala Lys Gly Thr Asn Gly Leu Val Arg Ala Ser Ser Ser Asn Ile Met
                165                 170                 175

Leu Tyr Gly Asn Leu Gly Asn Leu Asn Gln Thr Gly Pro Val Thr Ala
                180                 185                 190

Gly Val Asn Tyr Gly Asn Asn Gly Tyr Gly Val Lys Arg Thr Thr
            195                 200                 205

Met Gly Ala Ala Thr Ala Thr Thr Lys Ser Gln Asp Gln Ser Gly
    210                 215                 220

Ser Leu Cys Arg Ala Ile Ser Thr Arg Met Asp Pro Glu Thr Leu Lys
225                 230                 235                 240

Ile Met Gly Asn Glu Asp Tyr Lys Asn Gly Asn Phe Ala Glu Ala Leu
                245                 250                 255

Ala Leu Tyr Asp Ala Ala Ile Ala Ile Asp Pro Asn Lys Ala Ala Tyr
                260                 265                 270

Arg Ser Asn Lys Ser Ala Ala Leu Thr Ala Leu Gly Arg Ile Leu Asp
            275                 280                 285

Ala Val Phe Glu Cys Arg Glu Ala Ile Arg Ile Glu Pro His Tyr His
        290                 295                 300

Arg Ala His His Arg Leu Gly Asn Leu Tyr Leu Arg Leu Gly Glu Val
305                 310                 315                 320

Glu Lys Ser Ile Tyr His Phe Lys His Ser Gly Pro Glu Ala Asp Arg
                325                 330                 335

Glu Asp Ile Ala Lys Ala Lys Thr Val Gln Thr His Leu Asn Lys Cys
            340                 345                 350

Thr Glu Ala Lys Arg Leu Arg Asp Trp Asn Gly Leu Ile Thr Glu Thr
        355                 360                 365

Thr Asn Thr Ile Ser Ser Gly Ala Asp Ala Ala Pro Gln Val Tyr Ala
    370                 375                 380

Leu Gln Ala Glu Ala Leu Leu Lys Thr His Arg His Gln Glu Ala Asp
385                 390                 395                 400

Asp Ala Leu Ser Arg Cys Pro Val Phe Asp Ile Asp Ala Ser Thr Arg
                405                 410                 415

Tyr Tyr Gly Pro Val Gly Tyr Ala Gly Phe Leu Val Val Arg Ala Gln
            420                 425                 430

Val His Leu Ala Ser Gly Arg Phe Asp Glu Ala Val Glu Ala Ile Gln
        435                 440                 445

Arg Ala Gly Lys Leu Asp Gly Asn Asn Arg Glu Val Ile Met Ile Ser
    450                 455                 460

Arg Arg Ala Gln Ala Val Thr Glu Ala Arg Phe Lys Gly Asn Glu Leu
465                 470                 475                 480

Phe Lys Ser Gly Arg Phe Gln Glu Ala Cys Ala Ala Tyr Gly Glu Gly
                485                 490                 495

Leu Asp His Asp Pro Arg Asn Ser Val Leu Leu Cys Asn Arg Ala Ala
            500                 505                 510

Cys Arg Ser Lys Leu Gly Gln Phe Asp Lys Ser Ile Glu Asp Cys Thr
        515                 520                 525
```

```
Ala Ala Leu Ser Val Arg Pro Gly Tyr Gly Lys Ala Arg Leu Arg Arg
        530                 535                 540

Ala Asp Cys Asn Ala Lys Ile Glu Lys Trp Glu Leu Ala Val Gly Asp
545                 550                 555                 560

Tyr Glu Ile Leu Lys Lys Glu Ser Pro Glu Asp Glu Gln Val Ile Arg
                565                 570                 575

Gly Leu Ser Glu Ala Gln Gln Gln Leu Met Lys Arg Ser Gly Gln Asp
            580                 585                 590

Ser

<210> SEQ ID NO 94
<211> LENGTH: 1674
<212> TYPE: DNA
<213> ORGANISM: Glycine max

<400> SEQUENCE: 94
```

| | | | | | |
|---|---|---|---|---|---|
| atgacagcag | tatttagacg | aaataatcca | tggtcacgca | aatcagtctc | tgcaggttct | 60 |
| tctcctatgg | cccacaattt | tgaaaaacca | tctaacactc | aagattcaaa | acggagacat | 120 |
| ggaggatcta | atgattttgt | tccaattaaa | gaatcttcac | ataataataa | caacaatgat | 180 |
| gttacaaact | actcttctcg | ttctgtcccc | aatcctcaaa | ggccaacaac | accacatgtt | 240 |
| gtaagccaaa | ggaaaccaca | acaaaatcgc | gatgaaacaa | caatgggaaa | agggtcttca | 300 |
| ccttcaccca | ctcagggcta | tatcaaccaa | ggcaaaaggg | taccaaaaga | agctgttgga | 360 |
| atctctggtg | aacttgaaag | catgatcaat | gaacacctaa | agtccaaggg | aagtagtacc | 420 |
| cttggtaatt | taggtaacct | taggcaagga | ggagtaggac | aaaacatca | caatgcttac | 480 |
| agtgaaatgg | attactatgc | tagtaatgtt | gctagtggag | acacacaaa | tcaaatcaca | 540 |
| ggacgtgaat | atgataaaac | tagttttttat | ggcaaggaag | ctaaaccaag | caaggaacaa | 600 |
| tcaggttcac | tgtgtagggc | tgtgtctaca | cgaatggatc | ctgaacaatt | gaagataatg | 660 |
| ggcaatgagg | attacaagaa | tggaaggttt | gcagaggcat | tggctttgta | tgatgctgcc | 720 |
| atcgcaattg | acccgaataa | ggcttcttat | aggagcaata | gaagtgctgc | attaactgct | 780 |
| cttggaaggc | ttttggaggc | tgttttttgaa | tgtagagaag | ctattcggat | tgagtctcat | 840 |
| taccaaaggg | cccatcatcg | gttgggaaat | ttgaacttaa | gattaggaga | aacagacaaa | 900 |
| gctttatatc | attataaaca | agcaggacca | gacgctgatc | cagatgagat | tgttaaagca | 960 |
| aagacactcc | aagtatatct | aaacaaatgc | accgaggctc | gtaggttcgg | cgattggatc | 1020 |
| acacttataa | ctgcaaccaa | caatgctata | tcatctggtg | cagactctgc | tccacaaata | 1080 |
| tatgcattac | aagccgaagc | cttgctaaag | cttcatagac | atcaagatgc | agacaaagta | 1140 |
| atgtcaaggt | gccctaaatt | tgatgttgat | cagtgtacta | ggttctttgg | acctattggt | 1200 |
| aatgcaaatt | tgttggtgac | acgggctcaa | gttgatttag | ttgctggcag | atttgaagaa | 1260 |
| gctctggagg | cagcacagaa | agctactagg | ttggattcta | atagtagaga | agcaaataag | 1320 |
| gtgatgagaa | aggctcgagc | tttgacaagt | gctcgtgcaa | agggaaatga | gcttttcaag | 1380 |
| gcatcaaatt | ttcatgaggc | ttgcattgcc | tatggagaag | gccttgacca | tgatccatat | 1440 |
| aactctgttt | tactatgcaa | cagagctgct | tgtagatcaa | agctaggcca | atttgagaaa | 1500 |
| gcaatagatg | attgcaatac | tgcccttaac | ttacgcccgt | cttacatcaa | ggccaggttg | 1560 |
| agaagggcag | attgtaatgc | taagttggaa | agatgggaag | cttcaataca | agactatgaa | 1620 |
| attttactaa | aagagacacc | ggaagatgaa | gaagtaaagc | gagcattgat | ggag | 1674 |

<210> SEQ ID NO 95
<211> LENGTH: 558
<212> TYPE: PRT
<213> ORGANISM: Glycine max

<400> SEQUENCE: 95

| | | | | | | | | | | | | | | |
|---|---|---|---|---|---|---|---|---|---|---|---|---|---|---|
| Met | Thr | Ala | Val | Phe | Arg | Arg | Asn | Asn | Pro | Trp | Ser | Arg | Lys | Ser | Val |
| 1 | | | | 5 | | | | | 10 | | | | | 15 | |

Ser Ala Gly Ser Ser Pro Met Ala His Asn Phe Glu Lys Pro Ser Asn
                20                  25                  30

Thr Gln Asp Ser Lys Arg Arg His Gly Gly Ser Asn Asp Phe Val Pro
            35                  40                  45

Ile Lys Glu Ser Ser His Asn Asn Asn Asn Asp Val Thr Asn Tyr
    50                  55                  60

Ser Ser Arg Ser Val Pro Asn Pro Gln Arg Pro Thr Thr Pro His Val
65                  70                  75                  80

Val Ser Gln Arg Lys Pro Gln Gln Asn Arg Asp Glu Thr Thr Met Gly
                85                  90                  95

Lys Gly Ser Ser Pro Ser Pro Thr Gln Gly Tyr Ile Asn Gln Gly Lys
            100                 105                 110

Arg Val Pro Lys Glu Ala Val Gly Ile Ser Gly Glu Leu Glu Ser Met
        115                 120                 125

Ile Asn Glu His Leu Lys Ser Lys Gly Ser Ser Thr Leu Gly Asn Leu
    130                 135                 140

Gly Asn Leu Arg Gln Gly Gly Val Gly Pro Lys His His Asn Ala Tyr
145                 150                 155                 160

Ser Glu Met Asp Tyr Tyr Ala Ser Asn Val Ala Ser Gly Gly His Thr
                165                 170                 175

Asn Gln Ile Thr Gly Arg Glu Tyr Asp Lys Thr Ser Phe Tyr Gly Lys
            180                 185                 190

Glu Ala Lys Pro Ser Lys Glu Gln Ser Gly Ser Leu Cys Arg Ala Val
        195                 200                 205

Ser Thr Arg Met Asp Pro Glu Gln Leu Lys Ile Met Gly Asn Glu Asp
    210                 215                 220

Tyr Lys Asn Gly Arg Phe Ala Glu Ala Leu Ala Leu Tyr Asp Ala Ala
225                 230                 235                 240

Ile Ala Ile Asp Pro Asn Lys Ala Ser Tyr Arg Ser Asn Arg Ser Ala
                245                 250                 255

Ala Leu Thr Ala Leu Gly Arg Leu Leu Glu Ala Val Phe Glu Cys Arg
            260                 265                 270

Glu Ala Ile Arg Ile Glu Ser His Tyr Gln Arg Ala His His Arg Leu
        275                 280                 285

Gly Asn Leu Asn Leu Arg Leu Gly Glu Thr Asp Lys Ala Leu Tyr His
    290                 295                 300

Tyr Lys Gln Ala Gly Pro Asp Ala Asp Pro Asp Glu Ile Val Lys Ala
305                 310                 315                 320

Lys Thr Leu Gln Val Tyr Leu Asn Lys Cys Thr Glu Ala Arg Arg Phe
                325                 330                 335

Gly Asp Trp Ile Thr Leu Ile Thr Ala Thr Asn Asn Ala Ile Ser Ser
            340                 345                 350

Gly Ala Asp Ser Ala Pro Gln Ile Tyr Ala Leu Gln Ala Glu Ala Leu
        355                 360                 365

Leu Lys Leu His Arg His Gln Asp Ala Asp Lys Val Met Ser Arg Cys
    370                 375                 380

Pro Lys Phe Asp Val Asp Gln Cys Thr Arg Phe Phe Gly Pro Ile Gly
385                 390                 395                 400

Asn Ala Asn Leu Leu Val Thr Arg Ala Gln Val Asp Leu Val Ala Gly
            405                 410                 415

Arg Phe Glu Glu Ala Leu Glu Ala Ala Gln Lys Ala Thr Arg Leu Asp
        420                 425                 430

Ser Asn Ser Arg Glu Ala Asn Lys Val Met Arg Lys Ala Arg Ala Leu
            435                 440                 445

Thr Ser Ala Arg Ala Lys Gly Asn Glu Leu Phe Lys Ala Ser Asn Phe
    450                 455                 460

His Glu Ala Cys Ile Ala Tyr Gly Glu Gly Leu Asp His Asp Pro Tyr
465                 470                 475                 480

Asn Ser Val Leu Leu Cys Asn Arg Ala Ala Cys Arg Ser Lys Leu Gly
            485                 490                 495

Gln Phe Glu Lys Ala Ile Asp Asp Cys Asn Thr Ala Leu Asn Leu Arg
        500                 505                 510

Pro Ser Tyr Ile Lys Ala Arg Leu Arg Arg Ala Asp Cys Asn Ala Lys
            515                 520                 525

Leu Glu Arg Trp Glu Ala Ser Ile Gln Asp Tyr Glu Ile Leu Leu Lys
530                 535                 540

Glu Thr Pro Glu Asp Glu Val Lys Arg Ala Leu Met Glu
545                 550                 555

<210> SEQ ID NO 96
<211> LENGTH: 321
<212> TYPE: DNA
<213> ORGANISM: Oryza sativa

<400> SEQUENCE: 96
atgacgactc caactcggcc caggctgcag atcatcgcaa cagcttcatc aggagagaag    60
caagctacaa taataactag atgtgtgttc ttgcagttgc actacatata cttccttagt   120
ttgtgttctt ctctaatgct ctggtactgt gcaaatagat gcatatgcta ttttgattct   180
ccatcatgtc tgtctctact ctctgctact atacagagca gctgttcatt tcttggcttg   240
aatgaagaca agggaaatgg atccgtctgc caagttcgat atgtgtatat aaatgtatta   300
gagatgtata aatacaagta a                                             321

<210> SEQ ID NO 97
<211> LENGTH: 106
<212> TYPE: PRT
<213> ORGANISM: Oryza sativa

<400> SEQUENCE: 97

Met Thr Thr Pro Thr Arg Pro Arg Leu Gln Ile Ile Ala Thr Ala Ser
1               5                   10                  15

Ser Gly Glu Lys Gln Ala Thr Ile Ile Thr Arg Cys Val Phe Leu Gln
            20                  25                  30

Leu His Tyr Ile Tyr Phe Leu Ser Leu Cys Ser Ser Leu Met Leu Trp
        35                  40                  45

Tyr Cys Ala Asn Arg Cys Ile Cys Tyr Phe Asp Ser Pro Ser Cys Leu
    50                  55                  60

Ser Leu Leu Ser Ala Thr Ile Gln Ser Ser Cys Ser Phe Leu Gly Leu
65                  70                  75                  80

Asn Glu Asp Lys Gly Asn Gly Ser Val Cys Gln Val Arg Tyr Val Tyr
            85                  90                  95

Ile Asn Val Leu Glu Met Tyr Lys Tyr Lys
            100                 105

<210> SEQ ID NO 98
<211> LENGTH: 213
<212> TYPE: DNA
<213> ORGANISM: Sorghum bicolor

<400> SEQUENCE: 98
atggagtact acgcctacca gcacggcaac agcagcagcg gcaacttgag ctcatcaaag      60
gagaagaggc cgccactgaa gagggggcag ctcaagcggc agatcgtgag gaccatcagc    120
aacctcgtgg tgccgaggaa cgccgctgct gctggtgctg gtgctggctc tgcctcaagg    180
gagaaattca gcagagggcc gagctacaac tga                                  213

<210> SEQ ID NO 99
<211> LENGTH: 70
<212> TYPE: PRT
<213> ORGANISM: Sorghum bicolor

<400> SEQUENCE: 99

Met Glu Tyr Tyr Ala Tyr Gln His Gly Asn Ser Ser Gly Asn Leu
1               5                   10                  15

Ser Ser Ser Lys Glu Lys Arg Pro Pro Leu Lys Arg Gly Gln Leu Lys
            20                  25                  30

Arg Gln Ile Val Arg Thr Ile Ser Asn Leu Val Val Pro Arg Asn Ala
        35                  40                  45

Ala Ala Ala Gly Ala Gly Ala Gly Ser Ala Ser Arg Glu Lys Phe Ser
    50                  55                  60

Arg Gly Pro Ser Tyr Asn
65                  70

<210> SEQ ID NO 100
<211> LENGTH: 1053
<212> TYPE: DNA
<213> ORGANISM: Oryza sativa

<400> SEQUENCE: 100
atgtctggtg gtgtgatcag catggtggtc gcgccatgga ttctcgcttg cgggttcttg      60
ctctgctcat cctccttcct cggagctgaa ggcgccattg tgtgaactac ggcatgctg     120 gggaacaacc tgccgtcgcc ggcgcaggtg atctccatgt acaaggccaa gaacatcaac    180
tacgtccgcc tcttccaccc ggacaccgcc gtcctcgccg cgtccgcaa ctccggcatc     240 ggcgtcgtcc tcggcacgta caacgaggac ctcgcccgcc tcgcctccga ccctcgtttt    300
gccgcctcct gggtcagctc ctacgtccag cccttcgccg cgccgtcag cttccgctac    360 atcaacgccg caacgaggt catccccggc gaccccgccg ccaacgtcct cccggccatg    420
cgcaacctcg acgccgcgct caaggccgcc gggatcagcg catcccggt caccaccgcc    480 gtcgccacgt ccgtgctcgg cgtctcgtac ccgccgtcgc agggcgcgtt ctcggaggcg    540
gcgtcgccgt acatggcgcc gatcgtcgcc tacctcgcgt ccaggggcgc gccgctgctg    600
gtgaacgtgt accctactt cgcgtacgcc gcggacgcgg agcgcgtgca gctcgggtac    660
gcgctgctgt cggcgtcgca gtcggcgtcg gtgaccgacg gcggcgtgac atacaccaac    720
atgttcgacg cgatcgtgga cgcggcgcac gcggcggtgg agaaggcgac gggcgggcag    780
gcggtggagc tggtggtgtc ggagaccggc tggccgtccg gtggcggcgg cgtgggcgcc    840
accgtggaga acgcggcggc gtacaacaac aacctgatcc gccacgtctc cggcggcgcc    900

```
gggacgccgc ggcggccggg gaagccggtg gagacgtacc tgttcgccat gttcaacgag    960
aaccagaagc ccgagggcgt ggagcagcat ttcggcctct ccagcccga catgaccgaa   1020 gtctaccatg tcgacttcgc ggcctccagc tag                                1053
```

<210> SEQ ID NO 101
<211> LENGTH: 350
<212> TYPE: PRT
<213> ORGANISM: Oryza sativa

<400> SEQUENCE: 101

```
Met Ser Gly Gly Val Ile Ser Met Val Ala Pro Trp Ile Leu Ala
1               5                   10                  15

Cys Gly Phe Leu Leu Cys Ser Ser Ser Phe Leu Gly Ala Glu Gly Ala
            20                  25                  30

Ile Gly Val Asn Tyr Gly Met Leu Gly Asn Asn Leu Pro Ser Pro Ala
        35                  40                  45

Gln Val Ile Ser Met Tyr Lys Ala Lys Asn Ile Asn Tyr Val Arg Leu
    50                  55                  60

Phe His Pro Asp Thr Ala Val Leu Ala Ala Leu Arg Asn Ser Gly Ile
65                  70                  75                  80

Gly Val Val Leu Gly Thr Tyr Asn Glu Asp Leu Ala Arg Leu Ala Ser
                85                  90                  95

Asp Pro Ser Phe Ala Ala Ser Trp Val Ser Ser Tyr Val Gln Pro Phe
            100                 105                 110

Ala Gly Ala Val Ser Phe Arg Tyr Ile Asn Ala Gly Asn Glu Val Ile
        115                 120                 125

Pro Gly Asp Pro Ala Ala Asn Val Leu Pro Ala Met Arg Asn Leu Asp
    130                 135                 140

Ala Ala Leu Lys Ala Ala Gly Ile Ser Gly Ile Pro Val Thr Thr Ala
145                 150                 155                 160

Val Ala Thr Ser Val Leu Gly Val Ser Tyr Pro Pro Ser Gln Gly Ala
                165                 170                 175

Phe Ser Glu Ala Ala Ser Pro Tyr Met Ala Pro Ile Val Ala Tyr Leu
            180                 185                 190

Ala Ser Arg Gly Ala Pro Leu Leu Val Asn Val Tyr Pro Tyr Phe Ala
        195                 200                 205

Tyr Ala Ala Asp Ala Glu Arg Val Gln Leu Gly Tyr Ala Leu Leu Ser
    210                 215                 220

Ala Ser Gln Ser Ala Ser Val Thr Asp Gly Gly Val Thr Tyr Thr Asn
225                 230                 235                 240

Met Phe Asp Ala Ile Val Asp Ala Ala His Ala Ala Val Glu Lys Ala
                245                 250                 255

Thr Gly Gly Gln Ala Val Glu Leu Val Val Ser Glu Thr Gly Trp Pro
            260                 265                 270

Ser Gly Gly Gly Val Gly Ala Thr Val Glu Asn Ala Ala Ala Tyr
        275                 280                 285

Asn Asn Asn Leu Ile Arg His Val Ser Gly Gly Ala Gly Thr Pro Arg
    290                 295                 300

Arg Pro Gly Lys Pro Val Glu Thr Tyr Leu Phe Ala Met Phe Asn Glu
305                 310                 315                 320

Asn Gln Lys Pro Glu Gly Val Glu Gln His Phe Gly Leu Phe Gln Pro
                325                 330                 335

Asp Met Thr Glu Val Tyr His Val Asp Phe Ala Ala Ser Ser
```

<210> SEQ ID NO 102
<211> LENGTH: 1146
<212> TYPE: DNA
<213> ORGANISM: Zea mays

<400> SEQUENCE: 102

```
atgttcttat gtatatgtat atgtttgttt gcttgtgcct gttcatcttc gcttcgcgtg      60
cgattatatc gcgattcgtt tctgagcttt gaggaatcga cgatcaagca tggcgacaaa     120
gtgatcgaac tcttcgagtt ctacgagatc gaagaccctg agcatctgtt tggtgaagga     180
gctgaaggcg cgattggcgt gaactacggc atggtcgcca caaacctgcc ggcgccggag     240
caggtcgtct ccatgtacaa ggccaagaac atcagctacg tgcggctctt ccacccggac     300
acggacgcgt tgaacgcgct ccgcggctcc ggcgtcggcg tcgtcctggg cacgctgaac     360
gaggacctcc cgcgcctggc gtccgacccg tccttcgccg cgtcgtgggt ggccacgaac     420
gtgcagccct tcgccggcgc cgtccagttc cggtacatca cgccggcaa cgaggtcatc      480
ccggggacg ccgcggcgcg ggtgctcccg gccatgcaga acctggagtc ggcgctccgg      540
tccgcggggg tcacgggcgt ccccgtcacc acggccgtgg ccaccagcgt gctcggcgcc     600
tcgtacccgc cgtcccaggg cgcattctcc gaggcggccg cgtcggtgat ggcgcccatc     660
gtctcgtacc tgtcgtcgaa gggcgcgccg ctgctggtca acgtataccc gtacttcgcc     720
tactcgagca gcggcgggca ggtggcgctc gggtacgcgc tgctgtcggc ggacgccggc     780
gcggcgtcgt cggtcacgga cgccggggtg gtctacacca acatgttcga cgctatcgtg     840
gacgcgacgc acgccgcggt ggagaaagcc ggggtccagg gctggagct ggtggtgtcg      900
gagaccggct ggccgtcggc cggcggcgag gcgccaccgt ggagaatgc cgcggcgtac      960
aacaacaacg tggtgcggca cgtcggcggc ggtaccccgc gccggccagg gaaggccgtg    1020
gagacgtacc ttttcgccat gttcaacgag aacggcaagg ccgagggcgt ggagcagcac    1080
ttcggcctct tccagccgga catgagcgag gtctaccacg tcgacttcac ggcgggatcc    1140
ccctag                                                                1146
```

<210> SEQ ID NO 103
<211> LENGTH: 381
<212> TYPE: PRT
<213> ORGANISM: Zea mays

<400> SEQUENCE: 103

```
Met Phe Leu Cys Ile Cys Ile Cys Leu Phe Ala Cys Ala Cys Ser Ser
1               5                   10                  15

Ser Leu Arg Val Arg Leu Tyr Arg Asp Ser Phe Leu Ser Phe Glu Glu
            20                  25                  30

Ser Thr Ile Lys His Gly Asp Lys Val Ile Glu Leu Phe Glu Phe Tyr
        35                  40                  45

Glu Ile Glu Asp Pro Glu His Leu Phe Gly Glu Gly Ala Glu Gly Ala
    50                  55                  60

Ile Gly Val Asn Tyr Gly Met Val Ala Asn Asn Leu Pro Ala Pro Glu
65                  70                  75                  80

Gln Val Val Ser Met Tyr Lys Ala Lys Asn Ile Ser Tyr Val Arg Leu
                85                  90                  95

Phe His Pro Asp Thr Asp Ala Leu Asn Ala Leu Arg Gly Ser Gly Val
            100                 105                 110
```

```
Gly Val Val Leu Gly Thr Leu Asn Glu Asp Leu Pro Arg Leu Ala Ser
            115                 120                 125

Asp Pro Ser Phe Ala Ala Ser Trp Val Ala Thr Asn Val Gln Pro Phe
        130                 135                 140

Ala Gly Ala Val Gln Phe Arg Tyr Ile Asn Ala Gly Asn Glu Val Ile
145                 150                 155                 160

Pro Gly Asp Ala Ala Arg Val Leu Pro Ala Met Gln Asn Leu Glu
                165                 170                 175

Ser Ala Leu Arg Ser Ala Gly Val Thr Gly Val Pro Val Thr Thr Ala
                180                 185                 190

Val Ala Thr Ser Val Leu Gly Ala Ser Tyr Pro Pro Ser Gln Gly Ala
            195                 200                 205

Phe Ser Glu Ala Ala Ala Ser Val Met Ala Pro Ile Val Ser Tyr Leu
        210                 215                 220

Ser Ser Lys Gly Ala Pro Leu Leu Val Asn Val Tyr Pro Tyr Phe Ala
225                 230                 235                 240

Tyr Ser Ser Ser Gly Gly Gln Val Ala Leu Gly Tyr Ala Leu Leu Ser
                245                 250                 255

Ala Asp Ala Gly Ala Ala Ser Ser Val Thr Asp Ala Gly Val Val Tyr
                260                 265                 270

Thr Asn Met Phe Asp Ala Ile Val Asp Ala Thr His Ala Ala Val Glu
            275                 280                 285

Lys Ala Gly Val Gln Gly Leu Glu Leu Val Val Ser Glu Thr Gly Trp
        290                 295                 300

Pro Ser Ala Gly Gly Glu Gly Ala Thr Val Glu Asn Ala Ala Ala Tyr
305                 310                 315                 320

Asn Asn Asn Val Val Arg His Val Gly Gly Gly Thr Pro Arg Arg Pro
                325                 330                 335

Gly Lys Ala Val Glu Thr Tyr Leu Phe Ala Met Phe Asn Glu Asn Gly
                340                 345                 350

Lys Ala Glu Gly Val Glu Gln His Phe Gly Leu Phe Gln Pro Asp Met
        355                 360                 365

Ser Glu Val Tyr His Val Asp Phe Thr Ala Gly Ser Pro
370                 375                 380
```

<210> SEQ ID NO 104
<211> LENGTH: 1092
<212> TYPE: DNA
<213> ORGANISM: Sorghum bicolor

<400> SEQUENCE: 104

```
atgacggcgt gcggtggtgg tgtgaggatg gcggttgctg cggcggcggc ggcgaagatg      60
gctgcgccat gggttcttgg ttgcagcttg ctgctctgct ggcgaccttt tcagggagct     120
gagtgtgcga tcggcgtgaa ctacggcatg tcgccaaca acctgccggc gccggagcag     180
gtgatctcca tgtacaaggc caagaacatc aactacgtgc cctcttcca cccggacacg     240
tcggtgctga acgcgctccg gggctccggc atcggcgttg tcctgggcac gctgaacgag     300
gacctccagc gtctggcgtc cgacccgtcc tacgccgcgt cgtgggtggc caccaacgtg     360
cagcccttcg ccggcgccgt ccagttccgg tacatcaacg ccggcaacga ggtcatcccg     420
ggggacgccg cggcgcaggt gctcccggcc atgcagaacc tggagtcggc gctccggtcc     480
gcggggtca ctggcgtccc cgtcacgacg gccgtggcca cgagcgtgct cggcacgtcg     540
tacccgccgt cccagggcgc cttctccgag gcggcggcgc cggtgatggc gcccatcgtc     600
```

```
tcgtacctgt cgtcgaaggg cgcgccgctg ctggtgaacg tgtacccgta cttcgcctac      660
tcgggcagcg gcgggcaggt ggcgctcggg tacgcgctgt tgtcgtcgga cgccagcgcg      720
gcgtcgtcgt cgtcggtgac ggacggcggg gtggtgtaca ccaacatgtt cgacgcgatc      780
gtggacgcga cgcacgcggc ggtggagaag gccgggtgc agggactgga gctggtggtg       840
tcggagaccg ggtggccgtc gggcggcggc ggcgacggcg ccaccgtgga gaacgcggcg      900
gcgtacaaca caacgtggt gcggcacgtc ggcggaggca ccccgcggcg gccagggaag       960
gccgtggaga cgtacctgtt cgccatgttc aacgagaacg gcaaggccga gggcgtggag     1020
cagcacttcg gcctcttcca gccggacatg agcgaggtct accacgtcga cttcacggcg     1080
gcttcttcct ag                                                         1092
```

<210> SEQ ID NO 105
<211> LENGTH: 363
<212> TYPE: PRT
<213> ORGANISM: Sorghum bicolor

<400> SEQUENCE: 105

```
Met Thr Ala Cys Gly Gly Gly Val Arg Met Ala Val Ala Ala Ala
1               5                   10                  15

Ala Ala Lys Met Ala Ala Pro Trp Val Leu Gly Cys Ser Leu Leu
                20                  25                  30

Cys Leu Ala Thr Phe Gln Gly Ala Glu Cys Ala Ile Gly Val Asn Tyr
                35                  40                  45

Gly Met Val Ala Asn Asn Leu Pro Ala Pro Glu Gln Val Ile Ser Met
        50                  55                  60

Tyr Lys Ala Lys Asn Ile Asn Tyr Val Arg Leu Phe His Pro Asp Thr
65                  70                  75                  80

Ser Val Leu Asn Ala Leu Arg Gly Ser Gly Ile Gly Val Val Leu Gly
                85                  90                  95

Thr Leu Asn Glu Asp Leu Gln Arg Leu Ala Ser Asp Pro Ser Tyr Ala
            100                 105                 110

Ala Ser Trp Val Ala Thr Asn Val Gln Pro Phe Ala Gly Ala Val Gln
        115                 120                 125

Phe Arg Tyr Ile Asn Ala Gly Asn Glu Val Ile Pro Gly Asp Ala Ala
    130                 135                 140

Ala Gln Val Leu Pro Ala Met Gln Asn Leu Glu Ser Ala Leu Arg Ser
145                 150                 155                 160

Ala Gly Val Thr Gly Val Pro Val Thr Thr Ala Val Ala Thr Ser Val
                165                 170                 175

Leu Gly Thr Ser Tyr Pro Pro Ser Gln Gly Ala Phe Ser Glu Ala Ala
            180                 185                 190

Ala Pro Val Met Ala Pro Ile Val Ser Tyr Leu Ser Ser Lys Gly Ala
        195                 200                 205

Pro Leu Leu Val Asn Val Tyr Pro Tyr Phe Ala Tyr Ser Gly Ser Gly
    210                 215                 220

Gly Gln Val Ala Leu Gly Tyr Ala Leu Leu Ser Ser Asp Ala Ser Ala
225                 230                 235                 240

Ala Ser Ser Ser Ser Val Thr Asp Gly Val Val Tyr Thr Asn Met
                245                 250                 255

Phe Asp Ala Ile Val Asp Ala Thr His Ala Ala Val Glu Lys Ala Gly
            260                 265                 270

Val Gln Gly Leu Glu Leu Val Val Ser Glu Thr Gly Trp Pro Ser Gly
        275                 280                 285
```

```
Gly Gly Gly Asp Gly Ala Thr Val Glu Asn Ala Ala Ala Tyr Asn Asn
        290                 295                 300

Asn Val Val Arg His Val Gly Gly Gly Thr Pro Arg Arg Pro Gly Lys
305                 310                 315                 320

Ala Val Glu Thr Tyr Leu Phe Ala Met Phe Asn Glu Asn Gly Lys Ala
                325                 330                 335

Glu Gly Val Glu Gln His Phe Gly Leu Phe Gln Pro Asp Met Ser Glu
            340                 345                 350

Val Tyr His Val Asp Phe Thr Ala Ala Ser Ser
            355                 360
```

<210> SEQ ID NO 106
<211> LENGTH: 1035
<212> TYPE: DNA
<213> ORGANISM: Arabidopsis thaliana

<400> SEQUENCE: 106

| | | |
|---|---|---|
| atggattgtc atagaaagac gttcttgttg aagttttgt gcgtggcatt tctgttaaac | 60 |
| tacagcaatg ttggctttgt agacgcagca acaaacattg gcttgaacta cggcctcctt | 120 |
| ggagacaacc tcccgcctcc atctgaagtt atcaacctct acaagtcctt aagtgttacc | 180 |
| aatattcgga tcttcgacac aactacggat gtccttaacg cctttcgagg gaatcgcaat | 240 |
| atcggagtta tggtagacgt gaagaaccaa gacttagagg ctctttcggt cagcgaagaa | 300 |
| gctgttaaca cctggttcgt gaccaacatt gagccttact tagctgatgt caacatcacg | 360 |
| ttcattgctg tcgggaacga agtcatccca ggggaaatcg gctcttatgt gctacccgtc | 420 |
| atgaaatctc tcaccaacat tgtcaagtcg aggagtctcc cgatcttgat cagcaccacg | 480 |
| gtggctatga ccaaccttgg ccagtcatat ccaccttcgg ccggagattt catgcctcaa | 540 |
| gcacgtgaac aacttacccc ggtgctgaag tttttgtctc aaacaaatac gcctatcctc | 600 |
| gtcaacatct cccctacttt cgcatatgct gctgatccta tcaacattca gctcgactat | 660 |
| gccatcttca acaccaacaa ggtcgtggtc aagacgggc cacttggtta caaacatg | 720 |
| ttcgatgtga tatttgatgc gttcgtatgg gcaatggaga agaaggtgt gaaggattta | 780 |
| ccaatggtgg taacagaaac tggatggcca tctgctggta acggaaactt aacgactcca | 840 |
| gatatcgcat ctatatacaa taccaatttt gttaaacatg tggaaagcgg taaagggacg | 900 |
| ccaaagagac caaagagtgg cattagtgga tttctatttg cgacgttcaa tgagaatcaa | 960 |
| aagccagcgg gaaccgaaca aaattttggg ttatataatc caacagatat gaagcccatc | 1020 |
| tacaagatgt tttga | 1035 |

<210> SEQ ID NO 107
<211> LENGTH: 344
<212> TYPE: PRT
<213> ORGANISM: Arabidopsis thaliana

<400> SEQUENCE: 107

```
Met Asp Cys His Arg Lys Thr Phe Leu Leu Lys Phe Leu Cys Val Ala
1               5                   10                  15

Phe Leu Leu Asn Tyr Ser Asn Val Gly Phe Val Asp Ala Ala Thr Asn
            20                  25                  30

Ile Gly Leu Asn Tyr Gly Leu Leu Gly Asp Asn Leu Pro Pro Ser
        35                  40                  45

Glu Val Ile Asn Leu Tyr Lys Ser Leu Ser Val Thr Asn Ile Arg Ile
50                  55                  60
```

```
Phe Asp Thr Thr Thr Asp Val Leu Asn Ala Phe Arg Gly Asn Arg Asn
 65                  70                  75                  80

Ile Gly Val Met Val Asp Val Lys Asn Gln Asp Leu Glu Ala Leu Ser
                 85                  90                  95

Val Ser Glu Glu Ala Val Asn Thr Trp Phe Val Thr Asn Ile Glu Pro
            100                 105                 110

Tyr Leu Ala Asp Val Asn Ile Thr Phe Ile Ala Val Gly Asn Glu Val
        115                 120                 125

Ile Pro Gly Glu Ile Gly Ser Tyr Val Leu Pro Val Met Lys Ser Leu
130                 135                 140

Thr Asn Ile Val Lys Ser Arg Ser Leu Pro Ile Leu Ile Ser Thr Thr
145                 150                 155                 160

Val Ala Met Thr Asn Leu Gly Gln Ser Tyr Pro Pro Ser Ala Gly Asp
                165                 170                 175

Phe Met Pro Gln Ala Arg Glu Gln Leu Thr Pro Val Leu Lys Phe Leu
            180                 185                 190

Ser Gln Thr Asn Thr Pro Ile Leu Val Asn Ile Tyr Pro Tyr Phe Ala
        195                 200                 205

Tyr Ala Ala Asp Pro Ile Asn Ile Gln Leu Asp Tyr Ala Ile Phe Asn
210                 215                 220

Thr Asn Lys Val Val Gln Asp Gly Pro Leu Gly Tyr Thr Asn Met
225                 230                 235                 240

Phe Asp Val Ile Phe Asp Ala Phe Val Trp Ala Met Glu Lys Glu Gly
                245                 250                 255

Val Lys Asp Leu Pro Met Val Val Thr Glu Thr Gly Trp Pro Ser Ala
            260                 265                 270

Gly Asn Gly Asn Leu Thr Thr Pro Asp Ile Ala Ser Ile Tyr Asn Thr
        275                 280                 285

Asn Phe Val Lys His Val Glu Ser Gly Lys Gly Thr Pro Lys Arg Pro
290                 295                 300

Lys Ser Gly Ile Ser Gly Phe Leu Phe Ala Thr Phe Asn Glu Asn Gln
305                 310                 315                 320

Lys Pro Ala Gly Thr Glu Gln Asn Phe Gly Leu Tyr Asn Pro Thr Asp
                325                 330                 335

Met Lys Pro Ile Tyr Lys Met Phe
            340
```

<210> SEQ ID NO 108
<211> LENGTH: 957
<212> TYPE: DNA
<213> ORGANISM: Glycine max

<400> SEQUENCE: 108

```
gcacttaacc tattgttgtg tttgaggata ctaaatttca tccagctgaa attacgggca     60
caattccaat ccgtgggtgt gtgttatgga ggaaaaggaa acaacctacc aaaaatgcaa    120
gcagtggtgg atttatacaa atcaaaccga attgacaaaa tccgtttata ccatccagac    180
gaaggagccc ttcaagccct cagaggttca aacatagagg tgatcctcgg tgtccctaat    240
gaccaacttc aatctctcat caatgttgca atgccacaa ttgggtcaa caagtacgtg    300
aaagcatact cacaaaacgt gaaattcaag tacattgcag ttgcacttga aacattcag    360
aacgcaattt ctgccgccaa tttacaatgc caagtcaagg tgtcaacagc aatagacacc    420
actttacttg gctactctta cccaccaaac gttgccgttt tcagcagtag tgcaagttca    480
```

| | | |
|---|---|---|
| tacataagac caattgtaaa cttttttagct agaaatggag ctccacttct cgcaaacgtg | 540 | |
| taccettact tcgcctatgt taacgaccaa caaagcatta gtcttgacta tgccttgttt | 600 | |
| actgaacatg gtaacaacga ggctgggtac caaaacctgt ttgatgcatt gttggattct | 660 | |
| ctatacgctg ctcttgagaa agtaggggca cccaatgtga cggttgttgt gtctgagagt | 720 | |
| gggtggccat ctgaaggtgg agcagtagca gccactgttc aaaacgcagg aacctattac | 780 | |
| cgcaacttga ttagccatgc caagggtgga accccaaaga ggcctaatgg tcccatagag | 840 | |
| atttatctct atgccatgtt tgatgaaaac cagaagcagg gtcaagaaat tcagcaacac | 900 | |
| ttcggtctct tcagacttga caaatcacct ttaaatatga aaatttggt cctctaa | 957 | |

<210> SEQ ID NO 109
<211> LENGTH: 318
<212> TYPE: PRT
<213> ORGANISM: Glycine max

<400> SEQUENCE: 109

Ala Leu Asn Leu Leu Cys Leu Arg Ile Leu Asn Phe Ile Gln Leu
1               5                   10                  15

Lys Leu Arg Ala Gln Phe Gln Ser Val Gly Val Cys Tyr Gly Gly Lys
            20                  25                  30

Gly Asn Asn Leu Pro Lys Met Gln Ala Val Val Asp Leu Tyr Lys Ser
        35                  40                  45

Asn Arg Ile Asp Lys Ile Arg Leu Tyr His Pro Asp Glu Gly Ala Leu
    50                  55                  60

Gln Ala Leu Arg Gly Ser Asn Ile Glu Val Ile Leu Gly Val Pro Asn
65                  70                  75                  80

Asp Gln Leu Gln Ser Leu Ile Asn Val Ala Asn Ala Thr Asn Trp Val
                85                  90                  95

Asn Lys Tyr Val Lys Ala Tyr Ser Gln Asn Val Lys Phe Lys Tyr Ile
            100                 105                 110

Ala Val Ala Leu Glu Asn Ile Gln Asn Ala Ile Ser Ala Ala Asn Leu
        115                 120                 125

Gln Cys Gln Val Lys Val Ser Thr Ala Ile Asp Thr Thr Leu Leu Gly
    130                 135                 140

Tyr Ser Tyr Pro Pro Asn Val Ala Val Phe Ser Ser Ala Ser Ser
145                 150                 155                 160

Tyr Ile Arg Pro Ile Val Asn Phe Leu Ala Arg Asn Gly Ala Pro Leu
                165                 170                 175

Leu Ala Asn Val Tyr Pro Tyr Phe Ala Tyr Val Asn Asp Gln Gln Ser
            180                 185                 190

Ile Ser Leu Asp Tyr Ala Leu Phe Thr Glu His Gly Asn Asn Glu Ala
        195                 200                 205

Gly Tyr Gln Asn Leu Phe Asp Ala Leu Leu Asp Ser Leu Tyr Ala Ala
    210                 215                 220

Leu Glu Lys Val Gly Ala Pro Asn Val Thr Val Val Ser Glu Ser
225                 230                 235                 240

Gly Trp Pro Ser Glu Gly Gly Ala Val Ala Ala Thr Val Gln Asn Ala
                245                 250                 255

Gly Thr Tyr Tyr Arg Asn Leu Ile Ser His Ala Lys Gly Gly Thr Pro
            260                 265                 270

Lys Arg Pro Asn Gly Pro Ile Glu Ile Tyr Leu Tyr Ala Met Phe Asp
        275                 280                 285

Glu Asn Gln Lys Gln Gly Gln Glu Ile Gln Gln His Phe Gly Leu Phe

```
                290                 295                 300
Arg Leu Asp Lys Ser Pro Leu Asn Met Lys Asn Leu Val Leu
305                 310                 315
```

<210> SEQ ID NO 110
<211> LENGTH: 630
<212> TYPE: DNA
<213> ORGANISM: Oryza sativa

<400> SEQUENCE: 110

```
atgtccaagc cgatcgccg ctccggcgcc gccacgtccc cgtcgctccg cttcctcggc     60
ctcctcaagc agcccgacga cggcagcggc gaccacgagc tggagctcga cgagcgcgac    120
gtcgtctggt cgtcgtcgtc gtcgtcgaac acctcgccct cctcgtgggc ctcctcaacc    180
aattcctcgc cgtccctcac cccgtccgcg tccgcgggcg tgggcgtccg ccggccgctg    240
tcgtcgtccc acgccttccc cgccgccggc agcgtcggcc tgtccgccct cctcgccgac    300
gatcacgccc ccacggcgtc catcccggcc aaggcacgcc cggagaggca gcagcccccg    360
cagccgtacc accagtcggc gccggtcgcc gtgccggcct ggcccaaggc cacggacagc    420
gacaggcgtc gccgtggtgt gcagcacgag gccctcaacg acgaggagga cgatgacgac    480
gagctcgtgg tgccgccgca cgagatggcc gcgcgccgcg ccgcggcggc ggcgtcggtg    540
atggagggcg ccgggcggac gctgaaaggg cgcgacctcc ggcgcgtgcg caacgcggtg    600
tggcgcacca ccggcttcct cgacctgtga                                     630
```

<210> SEQ ID NO 111
<211> LENGTH: 209
<212> TYPE: PRT
<213> ORGANISM: Oryza sativa

<400> SEQUENCE: 111

```
Met Ser Lys Pro Asp Arg Arg Ser Gly Ala Ala Thr Ser Pro Ser Leu
1               5                   10                  15

Arg Phe Leu Gly Leu Leu Lys Gln Pro Asp Asp Gly Ser Gly Asp His
                20                  25                  30

Glu Leu Glu Leu Asp Glu Arg Asp Val Val Trp Ser Ser Ser Ser
            35                  40                  45

Ser Asn Thr Ser Pro Ser Ser Trp Ala Ser Ser Thr Asn Ser Ser Pro
    50                  55                  60

Ser Leu Thr Pro Ser Ala Ser Ala Gly Val Gly Val Arg Arg Pro Leu
65                  70                  75                  80

Ser Ser Ser His Ala Phe Pro Ala Ala Gly Ser Val Gly Leu Ser Ala
                85                  90                  95

Leu Leu Ala Asp Asp His Ala Pro Thr Ala Ser Ile Pro Ala Lys Ala
                100                 105                 110

Arg Pro Glu Arg Gln Gln Pro Gln Pro Tyr His Gln Ser Ala Pro
            115                 120                 125

Val Ala Val Pro Ala Trp Pro Lys Ala Thr Asp Ser Asp Arg Arg Arg
    130                 135                 140

Arg Gly Val Gln His Glu Ala Leu Asn Asp Glu Glu Asp Asp Asp Asp
145                 150                 155                 160

Glu Leu Val Val Pro Pro His Glu Met Ala Ala Arg Arg Ala Ala Ala
                165                 170                 175

Ala Ala Ser Val Met Glu Gly Ala Gly Arg Thr Leu Lys Gly Arg Asp
            180                 185                 190
```

```
Leu Arg Arg Val Arg Asn Ala Val Trp Arg Thr Thr Gly Phe Leu Asp
        195                 200                 205

Leu

<210> SEQ ID NO 112
<211> LENGTH: 516
<212> TYPE: DNA
<213> ORGANISM: Zea mays

<400> SEQUENCE: 112
atggcgatgc cgagggcggc gggcgcgggg tcgctccgct tcctgggcct gctgaagcag      60
ccggagtccg acgccgccgc cccattcgag ctcgacgagc gcgacgtgtt gtggccggcg     120 ggcgggggc agcaggacgg ttgtgccgcc cgccggcga ggcgtcgtcg cgcgcacgcc       180
gtgccgctgt acagcttcgg gctgtcgtcg ctgctcgccg aaggctgcgg cggcggggtg     240
cccgtgcccg tgcccgtgcc ggggagggcg atggcgccga cgccgcgcc gaggcagtcg      300 gcgccggtgc gcgtgccggc gccgtggcca ggcggcagga gggccgacga ggacgaggag     360
gacggcgagg aggtggtgcc gccgcacgtg gtcgcggcgc ggcgccacgc gcggtcgtcg     420
tccgtgctgg agggcgccgg cgcacgctc aagggccgcg acctccgtag cgtccgcaac     480
gccgtgctcc ggcagaccgg gttcttggac ctgtga                               516

<210> SEQ ID NO 113
<211> LENGTH: 171
<212> TYPE: PRT
<213> ORGANISM: Zea mays

<400> SEQUENCE: 113

Met Ala Met Pro Arg Ala Ala Gly Ala Gly Ser Leu Arg Phe Leu Gly
1               5                   10                  15

Leu Leu Lys Gln Pro Glu Ser Asp Ala Ala Pro Phe Glu Leu Asp
            20                  25                  30

Glu Arg Asp Val Leu Trp Pro Ala Gly Gly Gln Gln Asp Gly Cys
        35                  40                  45

Ala Ala Pro Pro Ala Arg Arg Arg Ala His Ala Val Pro Leu Tyr
    50                  55                  60

Ser Phe Gly Leu Ser Ser Leu Leu Ala Glu Gly Cys Gly Gly Gly Val
65                  70                  75                  80

Pro Val Pro Val Pro Val Pro Gly Arg Ala Met Ala Pro Ser Ala Ala
                85                  90                  95

Pro Arg Gln Ser Ala Pro Val Arg Val Pro Ala Pro Trp Pro Gly Gly
            100                 105                 110

Arg Arg Ala Asp Glu Asp Glu Glu Asp Gly Glu Glu Val Val Pro Pro
        115                 120                 125

His Val Val Ala Ala Arg Arg His Ala Arg Ser Ser Ser Val Leu Glu
    130                 135                 140

Gly Ala Gly Arg Thr Leu Lys Gly Arg Asp Leu Arg Ser Val Arg Asn
145                 150                 155                 160

Ala Val Leu Arg Gln Thr Gly Phe Leu Asp Leu
                165                 170

<210> SEQ ID NO 114
<211> LENGTH: 582
<212> TYPE: DNA
<213> ORGANISM: Sorghum bicolor

<400> SEQUENCE: 114
```

```
atgccgaggg cgccgggcgc gggctcgctc cgcttcctgg gcctcctgaa gcagccggag    60
tcagcagggc ccgacgccgc cgcgccccta cgacgagcgcg acgtcgtgtg ccggcgggc    120 gggggcagc aggacgggtg ggccacccccg ccggcgtcgg cgccacaggc ggcgaggcgg    180
cgcgcgcacg ccgtgccgca cagcttcggg ctgtcgtccc tgctcgccga caacggcggc    240
ggcggcggag tggccgtgcc agtgcacgtg cccgtgaggg cggtggcgcc gagcgccgcg    300
ccgaggcagt cggcgccggt gcgggtgccg gcgccgtggc cggggaaggc ggcgggcgag    360
cgccgcgcgg gggaggacgg ccgcggaggc ggggcggca gcagaagggc cgacgaggac    420
gaggaggacg gcgacgagat ggtgccgccg cacgtggtcg cggcgcggcg ccacgcgcgg    480
tcgtcgtccg tgctggaggg cgccgggcgc acgctcaagg gccgcgacct ccgccgcgtc    540
cgcaacgccg tgctccggca gaccgggttc ctggacctct ga                      582
```

<210> SEQ ID NO 115
<211> LENGTH: 193
<212> TYPE: PRT
<213> ORGANISM: Sorghum bicolor

<400> SEQUENCE: 115

```
Met Pro Arg Ala Pro Gly Ala Gly Ser Leu Arg Phe Leu Gly Leu Leu
1               5                   10                  15

Lys Gln Pro Glu Ser Ala Gly Pro Asp Ala Ala Pro Leu Asp Glu
            20                  25                  30

Arg Asp Val Val Trp Pro Ala Gly Gly Gln Gln Asp Gly Trp Ala
        35                  40                  45

Thr Pro Pro Ala Ser Ala Pro Gln Ala Ala Arg Arg Ala His Ala
    50                  55                  60

Val Pro His Ser Phe Gly Leu Ser Ser Leu Leu Ala Asp Asn Gly Gly
65                  70                  75                  80

Gly Gly Gly Val Ala Val Pro Val His Val Pro Val Arg Ala Val Ala
                85                  90                  95

Pro Ser Ala Ala Pro Arg Gln Ser Ala Pro Val Arg Val Pro Ala Pro
            100                 105                 110

Trp Pro Gly Lys Ala Ala Gly Glu Arg Arg Ala Gly Glu Asp Gly Arg
        115                 120                 125

Gly Gly Gly Gly Ser Arg Arg Ala Asp Glu Asp Glu Glu Asp Gly
    130                 135                 140

Asp Glu Met Val Pro Pro His Val Val Ala Ala Arg Arg His Ala Arg
145                 150                 155                 160

Ser Ser Ser Val Leu Glu Gly Ala Gly Arg Thr Leu Lys Gly Arg Asp
                165                 170                 175

Leu Arg Arg Val Arg Asn Ala Val Leu Arg Gln Thr Gly Phe Leu Asp
            180                 185                 190

Leu
```

<210> SEQ ID NO 116
<211> LENGTH: 447
<212> TYPE: DNA
<213> ORGANISM: Arabidopsis thaliana

<400> SEQUENCE: 116

```
atggcgacag cgacgagaaa gagctattac caacgcccga gtcatcgctt ccttccaaca    60
gatcggactt acaacgtcac cggagattca gaattcgagt cgacgagtc tgatctatac   120
```

```
tctaaccgct ccgattcgcc tgaatttcgt cggaaactca tcacatcaaa ccgtaaatcg    180
tctccggcaa ccgtaaccac cactacagta gcttcttcac ttccgatgaa cgtacagaac    240
tggtctaaga ttctcgggaa agagaatcgg aaaagcatcg aaaacgatga cgatggcggc    300
gaaggaaaat tgccgccgca tgagtatttg gcgaagacga gaatggcttc gttctctgtg    360
catgaaggaa ttggaggac attgaaagga agagatatga gtagggtgag aaatgcaatt    420
ttggaaaaga ctgggttctt agattaa                                       447
```

<210> SEQ ID NO 117
<211> LENGTH: 148
<212> TYPE: PRT
<213> ORGANISM: Arabidopsis thaliana

<400> SEQUENCE: 117

```
Met Ala Thr Ala Thr Arg Lys Ser Tyr Tyr Gln Arg Pro Ser His Arg
1               5                   10                  15

Phe Leu Pro Thr Asp Arg Thr Tyr Asn Val Thr Gly Asp Ser Glu Phe
            20                  25                  30

Glu Phe Asp Glu Ser Asp Leu Tyr Ser Asn Arg Ser Asp Ser Pro Glu
        35                  40                  45

Phe Arg Arg Lys Leu Ile Thr Ser Asn Arg Lys Ser Ser Pro Ala Thr
    50                  55                  60

Val Thr Thr Thr Val Ala Ser Ser Leu Pro Met Asn Val Gln Asn
65                  70                  75                  80

Trp Ser Lys Ile Leu Gly Lys Glu Asn Arg Lys Ser Ile Glu Asn Asp
                85                  90                  95

Asp Asp Gly Gly Glu Gly Lys Leu Pro Pro His Glu Tyr Leu Ala Lys
            100                 105                 110

Thr Arg Met Ala Ser Phe Ser Val His Glu Gly Ile Gly Arg Thr Leu
        115                 120                 125

Lys Gly Arg Asp Met Ser Arg Val Arg Asn Ala Ile Leu Glu Lys Thr
    130                 135                 140

Gly Phe Leu Asp
145
```

<210> SEQ ID NO 118
<211> LENGTH: 450
<212> TYPE: DNA
<213> ORGANISM: Glycine max

<400> SEQUENCE: 118

```
atgaccaaca ttcgaagagc aacctatcgc tttctccctg ccatggacac agattctttc     60
tccgattcca acttcgaatt ccaggaatcc gatctctaca actccgctcg cgctaactct    120
cccgaatttc gcaaatccgt acgcgcctcc agatttcaca ctactcttc ctccggcggc    180 cgcgtcggta ctccggtgtc gcttccggtg aacgtgccgg actggtcgaa gattctcggc    240
gacgagttcg acggaaccga gaggaggaac tacgacgaag cgcagagcga tgaggaagat    300
ggagatggga gagtgcctcc gcacgagttt ctggcgaaga cgggaatcgc ttcgttctcg    360
gtgcacgaag gagttggaag gactctcaaa ggacgcgatc tcagtagggt tcgaaacgcg    420
atttgggcta aacaggatt ccaggactag                                     450
```

<210> SEQ ID NO 119
<211> LENGTH: 149
<212> TYPE: PRT
<213> ORGANISM: Glycine max

<400> SEQUENCE: 119

```
Met Thr Asn Ile Arg Arg Ala Thr Tyr Arg Phe Leu Pro Ala Met Asp
1               5                   10                  15

Thr Asp Ser Phe Ser Asp Ser Asn Phe Glu Phe Gln Glu Ser Asp Leu
            20                  25                  30

Tyr Asn Ser Ala Arg Ala Asn Ser Pro Glu Phe Arg Lys Ser Val Arg
        35                  40                  45

Ala Ser Arg Phe His Asn Tyr Ser Ser Ser Gly Gly Arg Val Gly Thr
    50                  55                  60

Pro Val Ser Leu Pro Val Asn Val Pro Asp Trp Ser Lys Ile Leu Gly
65                  70                  75                  80

Asp Glu Phe Gly Arg Asn Gln Arg Arg Asn Tyr Asp Glu Ala Gln Ser
                85                  90                  95

Asp Glu Glu Asp Gly Asp Gly Arg Val Pro Pro His Glu Phe Leu Ala
            100                 105                 110

Lys Thr Gly Ile Ala Ser Phe Ser Val His Glu Gly Val Gly Arg Thr
        115                 120                 125

Leu Lys Gly Arg Asp Leu Ser Arg Val Arg Asn Ala Ile Trp Ala Lys
    130                 135                 140

Thr Gly Phe Gln Asp
145
```

<210> SEQ ID NO 120
<211> LENGTH: 1599
<212> TYPE: DNA
<213> ORGANISM: Oryza sativa

<400> SEQUENCE: 120

| | |
|---|---|
| atgacgccgc gggagggcgg cggcggcggc ggaggcggcg tggtggggtt ggtagcgtac | 60 |
| gcggcgctgg cggtggtggc gctgcgggtg gtgctgtcgt acaagtcggt ggcgcacgcg | 120 |
| gtgcggagga tgtggcggtg gcggacgag tgggcgcagg cgtaccagta ctacgaggtg | 180 |
| ccgcggttcg gcggcggcgg cggcgagggg gtggagaatc cgctgttcag gaaggcggcg | 240 |
| gcgtacgtgg cggcgctgcc gtcgctggag gacgcggacg cggcgtgcgt gctgtcgtcg | 300 |
| gcgtgcaaga ccaacgactt ctcgctgcag ctcgggccgg gcacacggc gcacgacgcg | 360 |
| ttcctcggcg cccgcctcgc gtggaccaac gccgggccgg cgggcgacgg cggcggcggc | 420 |
| cgcgagcgcc tggtgttgcg tgtgcgtcga catgacagga cgcgcgtgct cgcccgtac | 480 |
| ctgcagcatg tcgagtcggt cgccgacgag atggagctcc gccggcgcga gctgaggctg | 540 |
| tacgcgaaca ccggcggcga tggcgccccc tcgccgaagt ggacgtcggc gccgttcacc | 600 |
| cacccggcca cgctggagac ggtggccatg gacccgagc tcaaggcccg cgtccgcgcc | 660 |
| gacctggaga gcttcctcaa gggcagggcg tactaccatc ggctcggtcg cgcgtggcgc | 720 |
| cggagctacc tgctctacgg cccgtccggc accgggaagt ccacgttcgc cgcggcgatg | 780 |
| gcgaggttct tggtgtacga cgtctacgac atcgacatgt cccgcggcgg ctgcgacgac | 840 |
| ctccgcgcgc tgctcctgga gaccaccccg cggtcgctca tcctcgtgga ggacctggac | 900 |
| cggtatctcc gcggcggcgg cgatgggag acgtccgccg cgaggacgtc gaggatgctc | 960 |
| agcttcatgg acgggctctc gtcgtgctgc ggcgaggagc gcgtcatggt gttcaccatg | 1020 |
| agcggcgaca aggacggcgt ggacccggcc atcctgcggc cggggaggct ggacgtgcac | 1080 |
| atccacttca ccatgtgcga cttcgagggg ttcaagactc tggccagcaa ctacctcggc | 1140 |

-continued

```
ctcaaggacc acaagctgta cccgcaggtg gaggagggct tccacgccgc cggcgcgcgc    1200
ctcagccccg ccgagctcgg cgagatcatg ctcgccaacc gcgggtcccc gagccgcgcg    1260
ctccgcacgg tcatcaacgc gctgcagcac gtggcgccgg cccggcgcc gccgcagcag     1320 cagccccggg cgagctccgc gtcgcggccg ccgcccaggc tgaccgcgag atggtccggt    1380
cacctcgacg aggcaagcgc ggcggacgca agcgcggcca accaatcgcc gggcggcggc    1440
ggcgggggat tcgggaagga cgcgccgatg agggagttca agaagctcta cgggctgatc    1500
aagatcagga gccgcaagga cggcggcgtc gttcccgtcg acgacacggc gtcggcgaac    1560 ggccgggca gtgacgtcag cgccgataag gaccggtga                           1599
```

<210> SEQ ID NO 121
<211> LENGTH: 532
<212> TYPE: PRT
<213> ORGANISM: Oryza sativa

<400> SEQUENCE: 121

```
Met Thr Pro Arg Glu Gly Gly Gly Gly Gly Gly Gly Val Val Gly
1               5                  10                  15

Leu Val Ala Tyr Ala Ala Leu Ala Val Val Ala Leu Arg Val Val Leu
                20                  25                  30

Ser Tyr Lys Ser Val Ala His Ala Val Arg Arg Met Trp Arg Trp Ala
            35                  40                  45

Asp Glu Trp Ala Gln Ala Tyr Gln Tyr Glu Val Pro Arg Phe Gly
        50                  55                  60

Gly Gly Gly Glu Gly Val Glu Asn Pro Leu Phe Arg Lys Ala Ala
65                  70                  75                  80

Ala Tyr Val Ala Ala Leu Pro Ser Leu Glu Asp Ala Asp Ala Ala Cys
                85                  90                  95

Val Leu Ser Ser Ala Cys Lys Thr Asn Asp Phe Ser Leu Gln Leu Gly
            100                 105                 110

Pro Gly His Thr Ala His Asp Ala Phe Leu Gly Ala Arg Leu Ala Trp
        115                 120                 125

Thr Asn Ala Gly Pro Ala Gly Asp Gly Gly Gly Arg Glu Arg Leu
130                 135                 140

Val Leu Arg Val Arg Arg His Asp Arg Thr Arg Val Leu Arg Pro Tyr
145                 150                 155                 160

Leu Gln His Val Glu Ser Val Ala Asp Glu Met Glu Leu Arg Arg Arg
                165                 170                 175

Glu Leu Arg Leu Tyr Ala Asn Thr Gly Gly Asp Gly Ala Pro Ser Pro
            180                 185                 190

Lys Trp Thr Ser Ala Pro Phe Thr His Pro Ala Thr Leu Glu Thr Val
        195                 200                 205

Ala Met Asp Pro Glu Leu Lys Ala Arg Val Arg Ala Asp Leu Glu Ser
210                 215                 220

Phe Leu Lys Gly Arg Ala Tyr Tyr His Arg Leu Gly Arg Ala Trp Arg
225                 230                 235                 240

Arg Ser Tyr Leu Leu Tyr Gly Pro Ser Gly Thr Gly Lys Ser Thr Phe
                245                 250                 255

Ala Ala Ala Met Ala Arg Phe Leu Val Tyr Asp Val Tyr Asp Ile Asp
            260                 265                 270

Met Ser Arg Gly Gly Cys Asp Asp Leu Arg Ala Leu Leu Leu Glu Thr
        275                 280                 285

Thr Pro Arg Ser Leu Ile Leu Val Glu Asp Leu Asp Arg Tyr Leu Arg
```

Gly Gly Gly Asp Gly Glu Thr Ser Ala Ala Arg Thr Ser Arg Met Leu
305                 310                 315                 320

Ser Phe Met Asp Gly Leu Ser Ser Cys Cys Gly Glu Glu Arg Val Met
            325                 330                 335

Val Phe Thr Met Ser Gly Asp Lys Asp Gly Val Asp Pro Ala Ile Leu
            340                 345                 350

Arg Pro Gly Arg Leu Asp Val His Ile His Phe Thr Met Cys Asp Phe
        355                 360                 365

Glu Gly Phe Lys Thr Leu Ala Ser Asn Tyr Leu Gly Leu Lys Asp His
370                 375                 380

Lys Leu Tyr Pro Gln Val Glu Glu Gly Phe His Ala Ala Gly Ala Arg
385                 390                 395                 400

Leu Ser Pro Ala Glu Leu Gly Glu Ile Met Leu Ala Asn Arg Gly Ser
                405                 410                 415

Pro Ser Arg Ala Leu Arg Thr Val Ile Asn Ala Leu Gln His Val Ala
            420                 425                 430

Pro Ala Pro Ala Pro Pro Gln Gln Gln Pro Arg Ala Ser Ser Ala Ser
435                 440                 445

Arg Pro Pro Arg Leu Thr Ala Arg Trp Ser Gly His Leu Asp Glu
    450                 455                 460

Ala Ser Ala Ala Asp Ala Ser Ala Ala Asn Gln Ser Pro Gly Gly Gly
465                 470                 475                 480

Gly Gly Gly Phe Gly Lys Asp Ala Pro Met Arg Glu Phe Lys Lys Leu
            485                 490                 495

Tyr Gly Leu Ile Lys Ile Arg Ser Arg Lys Asp Gly Gly Val Val Pro
            500                 505                 510

Val Asp Asp Thr Ala Ser Ala Asn Gly Arg Gly Ser Asp Val Ser Ala
        515                 520                 525

Asp Lys Asp Arg
    530

<210> SEQ ID NO 122
<211> LENGTH: 1542
<212> TYPE: DNA
<213> ORGANISM: Zea mays

<400> SEQUENCE: 122
atgatggggc aggacggcgt cggcggaggg gtgatcgggg ccctgctcta cgccgcgctg      60
gcggtgctgg cgctgcgtct ggtgctgtcg tacaagtcgg cggcgcacgc ggtgcggcgg     120
gcgtggcggt gggcggacga gtgggcgcag gcgtaccagt actacgaggt gccgcgcctc     180
gccgtcgacg gcgcggagaa cccgctgttc cggaaggcgg cggcgtacgt ggcgtcgctg     240
ccgtcgctcg aggacgcgga cgccgcctgc gtgctgtcgt cggcggccaa gagcaacgac     300
ttcgcgctgc agctggggcc gggccacacc gcgcgggacg cgttcctcgg cgcgcgcctc     360
gcgtggacca acgccggcgg cgacggccgc ctcgtgctcc gcgtgcgccg ccacgaccgc     420
acccgcgtgc tgcggcccta cctgcagcac ctcgagtccg tcgccgacga gatggaggcg     480
cgccgccgcg agctgcgggt ccacgccaac gccggcggtg gcgcgccgcg gtgggcgtcc     540
gcgcccttca cgcacccggc cacgctcgac acggtggcca tggaccccga cctcaaggcc     600
cgcgtccgcg ccgacctgga gagcttcctc aagggccgcg cgtactacca ccgcctcggc     660
cgcgtctggc gcaggagcta cctgctgtac ggcgctcccg gcacgggcaa gtccacgttc     720

```
gccgccgcga tggcgaggtt cctggggtac gacgtctacg acgtggacct gtcccgcggc   780
ggctgcgacg acctccgcgc cctgctcctg gacaccgccc gcggtcgct catcctcgtg    840 gaggacctcg accgctacct gcgcggcggg gacggcgaga cggcggcggc gaggaccgcg   900
cgcgtgctcg gcttcatgga cgggctctcc tcgtcatgcg gcgaggagcg cgtgatggtg   960
ttcaccatga gcgggggcaa ggacggcgtg gacccggccg tgctgcggcc cggccggctc  1020
gacgtccaca tccacttcac catgtgcgac ttcgagggat tcaaggctct ggcgagcaac  1080
tacctggggc tcaaggacca caagctgtac ccgcaggtgg aggagggtt ccacgccggc   1140 gcccgcctca gccccgccga gctcggcgag atcatgctcg ccaaccgcgg gtccgcgagc  1200
cgcgcgctcc gcaccgtcat cagcgcgctg cagcacgtgg ccccgtcacc gcctccgcag  1260
cggaccgtca ccgcggcgcg gccgccgagg ctgacatcga gatggtccgg cacctcgac   1320 gaggccagcg tcgcgaccgc gacgtccgag gccagcgcgg cggggcagtc gccgcggggc  1380 ggggaggtt tcgccaagga cgcgccgatc agggagatca agaagctcta cggtctgatc    1440
aagtacagga gccgcaagga cgccggcgtc gtgccggtgg atgacagcgc ggcatcgccg  1500
gacgggcggg acagcgacgt tagcccgag aaggaccggt ga                        1542
```

<210> SEQ ID NO 123
<211> LENGTH: 513
<212> TYPE: PRT
<213> ORGANISM: Zea mays

<400> SEQUENCE: 123

```
Met Met Gly Gln Asp Gly Val Gly Gly Val Ile Gly Ala Leu Leu
1               5                   10                  15

Tyr Ala Ala Leu Ala Val Leu Ala Leu Arg Leu Val Leu Ser Tyr Lys
                20                  25                  30

Ser Ala Ala His Ala Val Arg Arg Ala Trp Arg Trp Ala Asp Glu Trp
            35                  40                  45

Ala Gln Ala Tyr Gln Tyr Tyr Glu Val Pro Arg Leu Ala Val Asp Gly
        50                  55                  60

Ala Glu Asn Pro Leu Phe Arg Lys Ala Ala Tyr Val Ala Ser Leu
65                  70                  75                  80

Pro Ser Leu Glu Asp Ala Asp Ala Ala Cys Val Leu Ser Ser Ala Ala
                85                  90                  95

Lys Ser Asn Asp Phe Ala Leu Gln Leu Gly Pro Gly His Thr Ala Arg
            100                 105                 110

Asp Ala Phe Leu Gly Ala Arg Leu Ala Trp Thr Asn Ala Gly Gly Asp
        115                 120                 125

Gly Arg Leu Val Leu Arg Val Arg Arg His Asp Arg Thr Arg Val Leu
    130                 135                 140

Arg Pro Tyr Leu Gln His Leu Glu Ser Val Ala Asp Glu Met Glu Ala
145                 150                 155                 160

Arg Arg Arg Glu Leu Arg Val His Ala Asn Ala Gly Gly Gly Ala Pro
                165                 170                 175

Arg Trp Ala Ser Ala Pro Phe Thr His Pro Ala Thr Leu Asp Thr Val
            180                 185                 190

Ala Met Asp Pro Asp Leu Lys Ala Val Arg Ala Asp Leu Glu Ser
        195                 200                 205

Phe Leu Lys Gly Arg Ala Tyr Tyr His Arg Leu Gly Arg Val Trp Arg
    210                 215                 220

Arg Ser Tyr Leu Leu Tyr Gly Ala Pro Gly Thr Gly Lys Ser Thr Phe
```

```
                225                 230                 235                 240
Ala Ala Ala Met Ala Arg Phe Leu Gly Tyr Asp Val Tyr Asp Val Asp
                    245                 250                 255
Leu Ser Arg Gly Gly Cys Asp Asp Leu Arg Ala Leu Leu Leu Asp Thr
                260                 265                 270
Ala Pro Arg Ser Leu Ile Leu Val Glu Asp Leu Asp Arg Tyr Leu Arg
            275                 280                 285
Gly Gly Asp Gly Glu Thr Ala Ala Ala Arg Thr Ala Arg Val Leu Gly
        290                 295                 300
Phe Met Asp Gly Leu Ser Ser Ser Cys Gly Glu Glu Arg Val Met Val
305                 310                 315                 320
Phe Thr Met Ser Gly Lys Asp Gly Val Asp Pro Ala Val Leu Arg
                325                 330                 335
Pro Gly Arg Leu Asp Val His Ile His Phe Thr Met Cys Asp Phe Glu
            340                 345                 350
Gly Phe Lys Ala Leu Ala Ser Asn Tyr Leu Gly Leu Lys Asp His Lys
        355                 360                 365
Leu Tyr Pro Gln Val Glu Glu Gly Phe His Ala Gly Ala Arg Leu Ser
    370                 375                 380
Pro Ala Glu Leu Gly Glu Ile Met Leu Ala Asn Arg Gly Ser Ala Ser
385                 390                 395                 400
Arg Ala Leu Arg Thr Val Ile Ser Ala Leu Gln His Val Ala Pro Ser
                405                 410                 415
Pro Pro Pro Gln Arg Thr Val Thr Ala Ala Arg Pro Arg Leu Thr
            420                 425                 430
Ser Arg Trp Ser Gly His Leu Asp Glu Ala Ser Val Ala Thr Ala Thr
        435                 440                 445
Ser Glu Ala Ser Ala Ala Gly Gln Ser Pro Arg Gly Gly Gly Phe
    450                 455                 460
Ala Lys Asp Ala Pro Ile Arg Glu Ile Lys Lys Leu Tyr Gly Leu Ile
465                 470                 475                 480
Lys Tyr Arg Ser Arg Lys Asp Ala Gly Val Val Pro Val Asp Asp Ser
                485                 490                 495
Ala Ala Ser Pro Asp Gly Arg Asp Ser Asp Val Ser Pro Glu Lys Asp
            500                 505                 510
Arg
```

<210> SEQ ID NO 124
<211> LENGTH: 1578
<212> TYPE: DNA
<213> ORGANISM: Sorghum bicolor

<400> SEQUENCE: 124

```
atgccactgc acgccacgag ccccgccggc gtgctcgcgt acgccgccct cgcgctcgcg    60
gcgctgcggc tgctgctgtc ctacaagtcg gcgctctacg cgctgcgccg cctgtggcgg   120
tgcgccgacg agtgggcgca ggcgtaccag taccacgagg tgccgcgctt cgccggggct   180
gggtgcgacg cgccgagaa cccgctgttc cgcaaggccg ccgcttacgt ggcggcgctg   240
ccgtcgctgg aggacgcgga cgccgcgtgc gtggtgtcct cggcgtcccg gaccaacggc   300
gggctctccc tgcagctcgg cccgggccac accgcgcggg acgcgttcct cggtgcgcgc   360
ctgtcgtgga ccagcgcggg cggcggaccc gagcgcctgg tgctgcgggt cgccgccac   420 gaccgctccc gcgtgctaag accttacctg cagcacgtgg agtccgtggc cgacgagatg   480
```

```
gagcagcgcc gccgcgagct gcggctcttc gccaacgccg gcaccgacgc ggacacaggc    540
gcgccgcgct gggcgtcggc gcccttcacc cacccggcca cgctcgacga cgtagccatg    600
gacccggacc tcaaggcccg cgtccgcgcc gacctcgaga gcttcctcaa gggccgcgcc    660
tactaccacc gcctcggccg cgtctggcgc cggagctacc tcctctacgg cccgccgggc    720
accggcaagt ccacgttcgc ggcggccatg gccaggttcc tgggctacga cgtctacgac    780
gtcgacctgt cccgcgccgt cgcctccggc gacgacctcc gcgcgctgct cctgcacacc    840
accccgcgct cgctcgtcct cgtcgaggac ctggaccggt acctgcaggg cggggcggg    900 gacggggagg cacgcgcggc cagggtgctg agcttcatgg acggcgtcgc gtcgtgctgc    960
ggcgaggagc gcgtcatggt gttcaccatg cgcggggca aggacgccgt cgacgccgcg   1020
gtgctgcgcc ccggccggct ggacgtgcac atccagttca cgctctgcga cttcgaggcg   1080
ttcaaggcgc tggccagcaa ctaccttggg ctcaaggacc acaagctgta cccgcaggtg   1140
gaagaggggt tccacgccgc cggcgcccgc ctcagcccg ccgagctcgg cgagatcatg   1200
ctggccaacc gcgcgtcccc gagccgcgcg ctccgcagcg tgatcaccaa gctccagcac   1260
gtcgcgtccg ggggcggcgc ggcgccgcgg tacccgtcgc acaggcggaa cacgagctgg   1320
tccggcggcg gcaccagtg ggaggaccag gcccagtcgg cgcgcgccag cgcggactcc   1380
gcgctggccg acgacgagac ggccgccggg gccccgccga cgtgcggggt gttcggcaag   1440
gaggcgccga tgagggagtt caagaagctg tacgggctga tcaagatcag gagccggagg   1500
gaggggtcgg gcgtcgtgcc acaggaaggc gacgcgcacg ggccgccgac gccgggcaac   1560
cacgacaggg accggtga                                                1578
```

<210> SEQ ID NO 125
<211> LENGTH: 525
<212> TYPE: PRT
<213> ORGANISM: Sorghum bicolor

<400> SEQUENCE: 125

```
Met Pro Leu His Ala Thr Ser Pro Ala Gly Val Leu Ala Tyr Ala Ala
1               5                   10                  15

Leu Ala Leu Ala Ala Leu Arg Leu Leu Leu Ser Tyr Lys Ser Ala Leu
            20                  25                  30

Tyr Ala Leu Arg Arg Leu Trp Arg Cys Ala Asp Glu Trp Ala Gln Ala
        35                  40                  45

Tyr Gln Tyr His Glu Val Pro Arg Phe Ala Gly Ala Gly Cys Asp Gly
    50                  55                  60

Ala Glu Asn Pro Leu Phe Arg Lys Ala Ala Tyr Val Ala Ala Leu
65                  70                  75                  80

Pro Ser Leu Glu Asp Ala Asp Ala Ala Cys Val Val Ser Ser Ala Ser
                85                  90                  95

Arg Thr Asn Gly Gly Leu Ser Leu Gln Leu Gly Pro Gly His Thr Ala
            100                 105                 110

Arg Asp Ala Phe Leu Gly Ala Arg Leu Ser Trp Thr Ser Ala Gly Gly
        115                 120                 125

Gly Pro Glu Arg Leu Val Leu Arg Val Arg His Asp Arg Ser Arg
    130                 135                 140

Val Leu Arg Pro Tyr Leu Gln His Val Glu Ser Val Ala Asp Glu Met
145                 150                 155                 160

Glu Gln Arg Arg Arg Glu Leu Arg Leu Phe Ala Asn Ala Gly Thr Asp
                165                 170                 175
```

Ala Asp Thr Gly Ala Pro Arg Trp Ala Ser Ala Pro Phe Thr His Pro
                180                 185                 190

Ala Thr Leu Asp Asp Val Ala Met Asp Pro Asp Leu Lys Ala Arg Val
            195                 200                 205

Arg Ala Asp Leu Glu Ser Phe Leu Lys Gly Arg Ala Tyr Tyr His Arg
        210                 215                 220

Leu Gly Arg Val Trp Arg Ser Tyr Leu Leu Tyr Gly Pro Pro Gly Pro Gly
225                 230                 235                 240

Thr Gly Lys Ser Thr Phe Ala Ala Ala Met Ala Arg Phe Leu Gly Tyr
                245                 250                 255

Asp Val Tyr Asp Val Asp Leu Ser Arg Ala Val Ala Ser Gly Asp Asp
            260                 265                 270

Leu Arg Ala Leu Leu Leu His Thr Thr Pro Arg Ser Leu Val Leu Val
        275                 280                 285

Glu Asp Leu Asp Arg Tyr Leu Gln Gly Gly Gly Asp Gly Glu Ala
    290                 295                 300

Arg Ala Ala Arg Val Leu Ser Phe Met Asp Gly Val Ala Ser Cys Cys
305                 310                 315                 320

Gly Glu Glu Arg Val Met Val Phe Thr Met Arg Gly Gly Lys Asp Ala
                325                 330                 335

Val Asp Ala Ala Val Leu Arg Pro Gly Arg Leu Asp Val His Ile Gln
            340                 345                 350

Phe Thr Leu Cys Asp Phe Glu Ala Phe Lys Ala Leu Ala Ser Asn Tyr
        355                 360                 365

Leu Gly Leu Lys Asp His Lys Leu Tyr Pro Gln Val Glu Glu Gly Phe
370                 375                 380

His Ala Ala Gly Ala Arg Leu Ser Pro Ala Glu Leu Gly Glu Ile Met
385                 390                 395                 400

Leu Ala Asn Arg Ala Ser Pro Ser Arg Ala Leu Arg Ser Val Ile Thr
                405                 410                 415

Lys Leu Gln His Val Ala Ser Gly Gly Ala Ala Pro Arg Tyr Pro
            420                 425                 430

Ser His Arg Arg Asn Thr Ser Trp Ser Gly Gly Gly His Gln Trp Glu
        435                 440                 445

Asp Gln Ala Gln Ser Ala Arg Ala Ser Ala Asp Ser Ala Leu Ala Asp
    450                 455                 460

Asp Glu Thr Ala Ala Gly Ala Pro Pro Thr Cys Gly Val Phe Gly Lys
465                 470                 475                 480

Glu Ala Pro Met Arg Glu Phe Lys Lys Leu Tyr Gly Leu Ile Lys Ile
                485                 490                 495

Arg Ser Arg Arg Glu Gly Ser Gly Val Val Pro Gln Glu Gly Asp Ala
            500                 505                 510

His Gly Pro Pro Thr Pro Gly Asn His Asp Arg Asp Arg
        515                 520                 525

<210> SEQ ID NO 126
<211> LENGTH: 1476
<212> TYPE: DNA
<213> ORGANISM: Arabidopsis thaliana

<400> SEQUENCE: 126
atggggattc tttgggattc gtttctcttg ttacttgtgt caacgtttgc tctgttctta      60
gttaggatcc tgttattcaa aactggattg atttacatgg tcaagttatg gcgtaggaag     120
atcatcgact ggtttcatgt ttaccaattc tacaaagtcc agaattcaa cgacaacgtt     180

-continued

```
caagagaatc atctctacca aaaagtctac atgtatctaa attccttaag ctcgatcgag    240
aattctgatt tcacgaacct cttcaccggg aaaaagtcca acgaaatcat cctccggtta    300
gatcggaacc aagtcgttgg cgacgagttt ctcggcgcta gagtttgttg gattaacgga    360
gaagacgaag atggagcgag gaatttcgtt ttgaagattc gtaaagctga caaacggaga    420
attctcggtt cttatctcca gcatatacat acagtatctg atgagcttga acagaggaac    480
acagagctta agcttttcat caacgtcgga atcgatgatc atctgaataa gaagaagaag    540
aagaacggac ggtggagatc gattccgttt gatcatcctt gtaccttcga acatcgcc     600 atggaaacgg atctgaagaa caaagtcaaa tctgatctcg aatctttcct caaaggtaaa    660
cagtattata atcgtctggg ccgtgtttgg aaacggagtt atctcttata cggaccttcc    720
ggtaccggaa aatcaagctt cgtcgcagca atggcgaatt cttagatta cgatgtttac    780 gatatagatc tctccaaagt agttgatgat tcagatctta agatgcttct gttacaaacc    840
agaggcaaat cagtgatcgt gatcgaagat ctagatcgac acctctcgac gaaatcaacg    900
gctgtgaatt tatctgggat tttgaatttc actgatagta ttctcagctc ttgcaccgcc    960
gatgaacgga tcatggtgtt tacgatgact gggaaagaac aaattgaccc ggctatgctt   1020
cgaccgggtc gggtcgacgt acacattcat tttcccttat gtgatttcac ggcgtttaaa   1080
acgctcgcta ataactactt aggtgttaaa gagcacaagc ttttctctca agttgaagga   1140
atatttcaaa acggtgcgtc tttgagtccc gccgagatcg gagagttgat gatcgcgaat   1200
cgtaactcgc cgactcgtgc attgaagcat gtcatcaatg cttttgcagac tgatggtgat   1260 cggagaggaa ctggacgacg tttgctttta gaaaatggtt cgagaaagtc gacgtcggag   1320
gatgtttctg atgatatgag tggttcgctt tgccggcggtg gcggaggaag ttcgccggcg   1380
gtgaaggagt ttaggaagtt gtatgggttg ttgagaatta aaagtagtag aaaatctgga   1440
tcgttcgatg tggctcgaga gatgagggac ggctag                             1476
```

<210> SEQ ID NO 127
<211> LENGTH: 491
<212> TYPE: PRT
<213> ORGANISM: Arabidopsis thaliana

<400> SEQUENCE: 127

```
Met Gly Ile Leu Trp Asp Ser Phe Leu Leu Leu Val Ser Thr Phe
1               5                   10                  15

Ala Leu Phe Leu Val Arg Ile Leu Leu Phe Lys Thr Gly Leu Ile Tyr
            20                  25                  30

Met Val Lys Leu Trp Arg Arg Lys Ile Ile Asp Trp Phe His Val Tyr
        35                  40                  45

Gln Phe Tyr Lys Val Pro Glu Phe Asn Asp Asn Val Gln Glu Asn His
    50                  55                  60

Leu Tyr Gln Lys Val Tyr Met Tyr Leu Asn Ser Leu Ser Ser Ile Glu
65                  70                  75                  80

Asn Ser Asp Phe Thr Asn Leu Phe Thr Gly Lys Lys Ser Asn Glu Ile
                85                  90                  95

Ile Leu Arg Leu Asp Arg Asn Gln Val Val Gly Asp Glu Phe Leu Gly
            100                 105                 110

Ala Arg Val Cys Trp Ile Asn Gly Glu Asp Glu Asp Gly Ala Arg Asn
        115                 120                 125

Phe Val Leu Lys Ile Arg Lys Ala Asp Lys Arg Ile Leu Gly Ser
    130                 135                 140
```

```
Tyr Leu Gln His Ile His Thr Val Ser Asp Glu Leu Glu Gln Arg Asn
145                 150                 155                 160

Thr Glu Leu Lys Leu Phe Ile Asn Val Gly Ile Asp Asp His Leu Asn
            165                 170                 175

Lys Lys Lys Lys Asn Gly Arg Trp Arg Ser Ile Pro Phe Asp His
        180                 185                 190

Pro Cys Thr Phe Asp Asn Ile Ala Met Glu Thr Asp Leu Lys Asn Lys
            195                 200                 205

Val Lys Ser Asp Leu Glu Ser Phe Leu Lys Gly Lys Gln Tyr Tyr Asn
210                 215                 220

Arg Leu Gly Arg Val Trp Lys Arg Ser Tyr Leu Leu Tyr Gly Pro Ser
225                 230                 235                 240

Gly Thr Gly Lys Ser Ser Phe Val Ala Ala Met Ala Asn Phe Leu Asp
            245                 250                 255

Tyr Asp Val Tyr Asp Ile Asp Leu Ser Lys Val Val Asp Asp Ser Asp
            260                 265                 270

Leu Lys Met Leu Leu Leu Gln Thr Arg Gly Lys Ser Val Ile Val Ile
            275                 280                 285

Glu Asp Leu Asp Arg His Leu Ser Thr Lys Ser Thr Ala Val Asn Leu
290                 295                 300

Ser Gly Ile Leu Asn Phe Thr Asp Ser Ile Leu Ser Ser Cys Thr Ala
305                 310                 315                 320

Asp Glu Arg Ile Met Val Phe Thr Met Thr Gly Lys Glu Gln Ile Asp
                325                 330                 335

Pro Ala Met Leu Arg Pro Gly Arg Val Asp Val His Ile His Phe Pro
            340                 345                 350

Leu Cys Asp Phe Thr Ala Phe Lys Thr Leu Ala Asn Asn Tyr Leu Gly
            355                 360                 365

Val Lys Glu His Lys Leu Phe Ser Gln Val Glu Gly Ile Phe Gln Asn
370                 375                 380

Gly Ala Ser Leu Ser Pro Ala Glu Ile Gly Glu Leu Met Ile Ala Asn
385                 390                 395                 400

Arg Asn Ser Pro Thr Arg Ala Leu Lys His Val Ile Asn Ala Leu Gln
            405                 410                 415

Thr Asp Gly Asp Arg Arg Gly Thr Gly Arg Arg Leu Leu Leu Glu Asn
            420                 425                 430

Gly Ser Arg Lys Ser Thr Ser Glu Asp Val Ser Asp Asp Met Ser Gly
            435                 440                 445

Ser Leu Cys Gly Gly Gly Gly Ser Ser Pro Ala Val Lys Glu Phe
        450                 455                 460

Arg Lys Leu Tyr Gly Leu Leu Arg Ile Lys Ser Ser Arg Lys Ser Gly
465                 470                 475                 480

Ser Phe Asp Val Ala Arg Glu Met Arg Asp Gly
            485                 490

<210> SEQ ID NO 128
<211> LENGTH: 1443
<212> TYPE: DNA
<213> ORGANISM: Glycine max

<400> SEQUENCE: 128
atgatttctc aaattagcat gctttccctt ttcttcttcc tcttctcctc ttttctaatc      60
gttttcttct tccgcaaaac ctctgcactt cacatcctca accaatggtt cctttccttc     120
```

```
gaaaaccgtc tccaccttca ccagtccttc aaaatccctc gctataatct tcactctctg    180
gacaatagcc tctaccggaa atcctcact tacctcgatt ctcttccctc cgttgaagat    240
tccgattaca ccaacctctt ctccggcccc aatccctccg acatcttcct ccacctcgac    300
cctaaccaca ccgttcatga caccttcctc ggcgccaggc tctcctggac caacgcctcc    360
ggcgacgcgc tcgtccttcg actaaagaag aaagacaagc gcagagtctt ccggcagtac    420
ttccagcaca ttctctccgt cgcggacgag atcgagcaac gaagaaaaaa ggacgtcaag    480
ctgtacgtga actccgactc cggcgagtgg cgctcggcgc cgttcacgca tccggcgagc    540
tttgagacgg tggcgatgga cgcggagctg aagaacaagg tgaagtccga tctggaccag    600
ttcctgaagt cgaagcagta ctaccaccgg ctaggccgcg tttggaagcg gagctacctc    660
ctctacggcg cgcctggcac cggaaaaatcc tccttcgtcg ccgcgatggc gaagttcctc    720
tgctacgacg tctacgacgt ggacgtttcg aagttcaccg atggcgccga ttggaaggtg    780
atgctgatgc agacgacggc gaagtctctg atcgtgatcg aagacctaga tcgcttgctg    840
acggagaagt caaagtcaaa cacaacgagc ttatcgagcg tgttgaactt catggacgga    900
atcgtatcgt gctgcggaga agagcgcgtg atggtgttca cgatgaacga aactaaagag    960
gaggttgatc aagcggttct gaggcctggg aggattgacg tgcacataca cttcccctta   1020
tgtgatttct ccacctttaa gattctcgcg agtagttact tagggttgaa ggagcacaag   1080
cttttccctc aggttgagga ggttttcag accggggccc ggctcagccc ggccgagctt   1140
ggtgagatta tgatatcgaa ccggaattcg cccacgcggg ccttgaaaac cgttatttcg   1200
gccctgcagg tgcaatccaa cggccccgaga gagggacaga ggttgagcca tagcgggtcg   1260
ggtcggaata gcgatgataa cgaaccgggt gcggttatat gtagggagag tgttcacacg   1320
gtgagggagt tccggaagct gtatgggctt ttgcgtttgg gaagtaggag gaaggaggag   1380
tcttattcgg ggcccataga gaaagagcct ccacgtattg agagtcgggt cggatataac   1440
taa                                                                 1443
```

<210> SEQ ID NO 129
<211> LENGTH: 480
<212> TYPE: PRT
<213> ORGANISM: Glycine max

<400> SEQUENCE: 129

```
Met Ile Ser Gln Ile Ser Met Leu Ser Leu Phe Phe Phe Leu Phe Ser
1               5                   10                  15

Ser Phe Leu Ile Val Phe Phe Arg Lys Thr Ser Ala Leu His Ile
            20                  25                  30

Leu Asn Gln Trp Phe Leu Ser Phe Glu Asn Arg Leu His Leu Gln
        35                  40                  45

Ser Phe Lys Ile Pro Arg Tyr Asn Leu His Ser Leu Asp Asn Ser Leu
    50                  55                  60

Tyr Arg Lys Ile Leu Thr Tyr Leu Asp Ser Leu Pro Ser Val Glu Asp
65                  70                  75                  80

Ser Asp Tyr Thr Asn Leu Phe Ser Gly Pro Asn Pro Ser Asp Ile Phe
                85                  90                  95

Leu His Leu Asp Pro Asn His Thr Val His Asp Thr Phe Leu Gly Ala
            100                 105                 110

Arg Leu Ser Trp Thr Asn Ala Ser Gly Asp Ala Leu Val Leu Arg Leu
        115                 120                 125

Lys Lys Lys Asp Lys Arg Arg Val Phe Arg Gln Tyr Phe Gln His Ile
```

```
            130                 135                 140
Leu Ser Val Ala Asp Glu Ile Glu Gln Arg Arg Lys Lys Asp Val Lys
145                 150                 155                 160

Leu Tyr Val Asn Ser Asp Ser Gly Glu Trp Arg Ser Ala Pro Phe Thr
                165                 170                 175

His Pro Ala Ser Phe Glu Thr Val Ala Met Asp Ala Glu Leu Lys Asn
            180                 185                 190

Lys Val Lys Ser Asp Leu Asp Gln Phe Leu Lys Ser Lys Gln Tyr Tyr
                195                 200                 205

His Arg Leu Gly Arg Val Trp Lys Arg Ser Tyr Leu Leu Tyr Gly Ala
            210                 215                 220

Pro Gly Thr Gly Lys Ser Ser Phe Val Ala Ala Met Ala Lys Phe Leu
225                 230                 235                 240

Cys Tyr Asp Val Tyr Asp Val Asp Val Ser Lys Phe Thr Asp Gly Ala
                245                 250                 255

Asp Trp Lys Val Met Leu Met Gln Thr Thr Ala Lys Ser Leu Ile Val
            260                 265                 270

Ile Glu Asp Leu Asp Arg Leu Leu Thr Glu Lys Ser Lys Ser Asn Thr
                275                 280                 285

Thr Ser Leu Ser Ser Val Leu Asn Phe Met Asp Gly Ile Val Ser Cys
290                 295                 300

Cys Gly Glu Glu Arg Val Met Val Phe Thr Met Asn Glu Thr Lys Glu
305                 310                 315                 320

Glu Val Asp Gln Ala Val Leu Arg Pro Gly Arg Ile Asp Val His Ile
                325                 330                 335

His Phe Pro Leu Cys Asp Phe Ser Thr Phe Lys Ile Leu Ala Ser Ser
            340                 345                 350

Tyr Leu Gly Leu Lys Glu His Lys Leu Phe Pro Gln Val Glu Glu Val
                355                 360                 365

Phe Gln Thr Gly Ala Arg Leu Ser Pro Ala Glu Leu Gly Glu Ile Met
370                 375                 380

Ile Ser Asn Arg Asn Ser Pro Thr Arg Ala Leu Lys Thr Val Ile Ser
385                 390                 395                 400

Ala Leu Gln Val Gln Ser Asn Gly Pro Arg Glu Gly Gln Arg Leu Ser
                405                 410                 415

His Ser Gly Ser Gly Arg Asn Ser Asp Asp Asn Glu Pro Gly Ala Val
            420                 425                 430

Ile Cys Arg Glu Ser Val His Thr Val Arg Glu Phe Arg Lys Leu Tyr
            435                 440                 445

Gly Leu Leu Arg Leu Gly Ser Arg Arg Lys Glu Glu Ser Tyr Ser Gly
450                 455                 460

Pro Ile Glu Lys Glu Pro Pro Arg Ile Glu Ser Arg Val Gly Tyr Asn
465                 470                 475                 480

<210> SEQ ID NO 130
<211> LENGTH: 654
<212> TYPE: DNA
<213> ORGANISM: Oryza sativa

<400> SEQUENCE: 130
atggcagcaa tggcgagcag ctgcagtgtg cttgttgtgg cctgcagctt cgctgtgctt    60
cacgtcgtcg ccatcgccgg cgcgacgcag tacaaggtcg gcggcgacgg cggatgggc    120 gtgcccggcg ccggcgacga gccgtacaac acctgggccg agaagaccag cttccaggtc    180
```

```
ggcgaccagc ttttgttcgt gtacccgaag acaaggact cggtgttggt ggtggagccg      240
gcggactaca acgcgtgcaa cacggcgtcg tacgacagca agttcgccga cggcaacacg      300
gcggtcacgc tcgaccgcgc cggcgccttc ttcttcatca gcggcgtcga cgccaactgc      360
cgcgccggcg agaagctcat cgtcatggtc gccaacgcca ccgggagcag cgcttcgccg      420
ccgtcctcct cgtcgtcgcc gtcgtctccc tccggtggtg gtggtggcgg tggcgctcca      480
gccgggcagg cgccgccggg tgctccggcc acgccggcgg ggacgaacag ctcgccggct      540
aacggcgggg cggccggcgg cggcgcgaag agtggcgctg gctcacggt ggcggcgagc       600 ggcctcgccg gctctctgat cgccgccatt gcctgcgtcg cgattgctat ctga           654
```

<210> SEQ ID NO 131
<211> LENGTH: 217
<212> TYPE: PRT
<213> ORGANISM: Oryza sativa

<400> SEQUENCE: 131

```
Met Ala Ala Met Ala Ser Ser Cys Ser Val Leu Val Ala Cys Ser
1               5                   10                  15

Phe Ala Val Leu His Val Val Ala Ile Ala Gly Ala Thr Gln Tyr Lys
            20                  25                  30

Val Gly Gly Asp Gly Gly Trp Gly Val Pro Gly Ala Gly Asp Glu Pro
        35                  40                  45

Tyr Asn Thr Trp Ala Glu Lys Thr Ser Phe Gln Val Gly Asp Gln Leu
    50                  55                  60

Leu Phe Val Tyr Pro Lys Asp Lys Asp Ser Val Leu Val Val Glu Pro
65                  70                  75                  80

Ala Asp Tyr Asn Ala Cys Asn Thr Ala Ser Tyr Asp Ser Lys Phe Ala
                85                  90                  95

Asp Gly Asn Thr Ala Val Thr Leu Asp Arg Ala Gly Ala Phe Phe
            100                 105                 110

Ile Ser Gly Val Asp Ala Asn Cys Arg Ala Gly Glu Lys Leu Ile Val
        115                 120                 125

Met Val Ala Asn Ala Thr Gly Ser Ser Ala Ser Pro Pro Ser Ser Ser
130                 135                 140

Ser Ser Pro Ser Ser Pro Ser Gly Gly Gly Gly Gly Gly Gly Ala Pro
145                 150                 155                 160

Ala Gly Gln Ala Pro Pro Gly Ala Pro Ala Thr Pro Ala Gly Thr Asn
                165                 170                 175

Ser Ser Pro Ala Asn Gly Gly Ala Ala Gly Gly Gly Ala Lys Ser Gly
            180                 185                 190

Ala Gly Leu Thr Val Ala Ala Ser Gly Leu Ala Gly Ser Leu Ile Ala
        195                 200                 205

Ala Ile Ala Cys Val Ala Ile Ala Ile
    210                 215
```

<210> SEQ ID NO 132
<211> LENGTH: 609
<212> TYPE: DNA
<213> ORGANISM: Zea mays

<400> SEQUENCE: 132

```
atgaggatgc gtgcgcgggc ggcatcggca tctgcgtcgg cggctgtggt ggtgctgctc       60
ctgctcctgc tactggtggg cgtctgcgcg ggcgccgtgt acaaggtagg cgacctggac      120
gcctggggcg tgccgccgcc gtccaagccc gacgtctaca gcgctgggc caagtccatc       180
```

-continued

```
cacttcgcgc tcggcgactc catctggttc ctgtacccgc cgagccagga ctcggtgctg    240
cagctggcgc cggcggcctt cgcgtcctgc gacctgtcgc gccccgtggc caggctcgcc    300
gacggcaact ccttattcaa cctcaccgcg cccggccgcg cctactacgc cagcggcgcg    360
ccgggtcact gccgcagggg ccagaagctc tgggtcgacg tgcccttgcc caacggcacc    420
tacctccagc cctccgccac cgacctcgcc gcgctcgcgc caccccgc cgccgacccg      480 cccgccgggt tcgcgtccgc tgccgccgcc gcgccacagg ggggcaacgc ctcgcccgcg    540
ccccgcgccg ccgccgccgc tggatccgtc gtcgcactct ccttcgcgct ccagatcctc    600
ctcctctga                                                            609
```

<210> SEQ ID NO 133
<211> LENGTH: 202
<212> TYPE: PRT
<213> ORGANISM: Zea mays

<400> SEQUENCE: 133

```
Met Arg Met Arg Ala Arg Ala Ala Ser Ala Ser Ser Ala Ala Val
1               5                   10                  15

Val Val Leu Leu Leu Leu Leu Leu Val Gly Val Cys Ala Gly Ala
            20                  25                  30

Val Tyr Lys Val Gly Asp Leu Asp Ala Trp Gly Val Pro Pro Ser
        35                  40                  45

Lys Pro Asp Val Tyr Lys Arg Trp Ala Lys Ser Ile His Phe Ala Leu
    50                  55                  60

Gly Asp Ser Ile Trp Phe Leu Tyr Pro Pro Ser Gln Asp Ser Val Leu
65                  70                  75                  80

Gln Leu Ala Pro Ala Ala Phe Ala Ser Cys Asp Leu Ser Arg Pro Val
                85                  90                  95

Ala Arg Leu Ala Asp Gly Asn Ser Leu Phe Asn Leu Thr Ala Pro Gly
            100                 105                 110

Arg Ala Tyr Tyr Ala Ser Gly Ala Pro Gly His Cys Arg Arg Gly Gln
        115                 120                 125

Lys Leu Trp Val Asp Val Pro Leu Pro Asn Gly Thr Tyr Leu Gln Pro
    130                 135                 140

Ser Ala Thr Asp Leu Ala Ala Leu Ala Pro Thr Pro Ala Ala Asp Pro
145                 150                 155                 160

Pro Ala Gly Phe Ala Ser Ala Ala Ala Ala Pro Gln Gly Gly Asn
                165                 170                 175

Ala Ser Pro Ala Pro Arg Ala Ala Ala Ala Gly Ser Val Val Ala
            180                 185                 190

Leu Ser Phe Ala Leu Gln Ile Leu Leu Leu
        195                 200
```

<210> SEQ ID NO 134
<211> LENGTH: 603
<212> TYPE: DNA
<213> ORGANISM: Sorghum bicolor

<400> SEQUENCE: 134

```
atgaggatgc gtgcgcgggc ggcattgcca tcggcgtcgg cgtcggtgct gctgctcctc    60
ctgctcctgg tgggcggctc cgccggcgcc gtgtacaagg tgggcgacct ggacgcctgg    120
ggcgtgccgc cgccgtccaa gcccgacgtc tacaagcgct gggccaagtc catccacttc    180
gcgctcggcg actccatctg gttcctgtac ccgccgagcc aggactcggt gctgcaggtg    240
```

```
acgccggagg ccttcgcgtc ctgcgacctg tcgcgccccg tggccaggct cgccgacggc    300
aactccttct tcaacctcac cacgccgggc cgcgcctact acgccagcgg cgcgccgggt    360
cactgccgca agggccagaa gctctgggtc gacgtcccca tggccaacgg cacctacctc    420
cagccctccg ccaccgacct cgccgcgctc gcgcccacac ccgccgccga cccgccgcc     480 gggttcgcat ccgcgtccgc gccagagggc gccagcgcct cgcccgcgcc ccgcgccgcc    540
gtcgccgccg ctggatccgt cgtcgccctc ctctgcttcg ccctccaaat cctcctccac    600
tga                                                                  603
```

```
<210> SEQ ID NO 135
<211> LENGTH: 200
<212> TYPE: PRT
<213> ORGANISM: Sorghum bicolor

<400> SEQUENCE: 135
```

Met Arg Met Arg Ala Arg Ala Ala Leu Pro Ser Ala Ser Ala Ser Val
1               5                   10                  15

Leu Leu Leu Leu Leu Leu Leu Val Gly Gly Ser Ala Gly Ala Val Tyr
            20                  25                  30

Lys Val Gly Asp Leu Asp Ala Trp Gly Val Pro Pro Ser Lys Pro
        35                  40                  45

Asp Val Tyr Lys Arg Trp Ala Lys Ser Ile His Phe Ala Leu Gly Asp
    50                  55                  60

Ser Ile Trp Phe Leu Tyr Pro Pro Ser Gln Asp Ser Val Leu Gln Val
65                  70                  75                  80

Thr Pro Glu Ala Phe Ala Ser Cys Asp Leu Ser Arg Pro Val Ala Arg
                85                  90                  95

Leu Ala Asp Gly Asn Ser Phe Phe Asn Leu Thr Thr Pro Gly Arg Ala
            100                 105                 110

Tyr Tyr Ala Ser Gly Ala Pro Gly His Cys Arg Lys Gly Gln Lys Leu
        115                 120                 125

Trp Val Asp Val Pro Met Ala Asn Gly Thr Tyr Leu Gln Pro Ser Ala
130                 135                 140

Thr Asp Leu Ala Ala Leu Ala Pro Thr Pro Ala Ala Asp Pro Pro Ala
145                 150                 155                 160

Gly Phe Ala Ser Ala Ser Ala Pro Glu Gly Ala Ser Ala Ser Pro Ala
                165                 170                 175

Pro Arg Ala Ala Val Ala Ala Gly Ser Val Val Ala Leu Leu Cys
            180                 185                 190

Phe Ala Leu Gln Ile Leu Leu His
        195                 200

```
<210> SEQ ID NO 136
<211> LENGTH: 576
<212> TYPE: DNA
<213> ORGANISM: Arabidopsis thaliana

<400> SEQUENCE: 136
```

```
atgggagtga tgagtttgag caagacgatg gtggtggtgg tattacaggt gatgatattg     60
ttgggacaag agattggtaa agtgtcgtcg actctataca aagttgggga cttggacgct    120
tggggcatcc caattgatgc taaagtctat tccaaatggc ccaaatctca ctctttcaag    180
atcggtgact ccctccttgt tcttgtaccc ccaagcgaag actcactgat tcaagtgacg    240
ccctccaatt tcaagagctg caacaccaaa gacccaatct tgtacatgaa cgacggcaac    300
```

```
tctctcttca acctcaccca aaacggaacc ctatacttca caagtgcaaa ccccggccac    360
tgtaccaagt accagaagct cctagtctcc gtcggcacct actccgccga agcagaggcc    420
ttgtctccgt cttctgccgc cgacgctccc tcttaccaaa acgccttcgg gtccattcct    480
ctctctcaga aatcgtctgc ttcctcctcg ctcatttctg ctttctccac tgtcgctgct    540
tcgctggctt gcgctgtcgt cggtgcaatc atgtga                             576
```

<210> SEQ ID NO 137
<211> LENGTH: 191
<212> TYPE: PRT
<213> ORGANISM: Arabidopsis thaliana

<400> SEQUENCE: 137

```
Met Gly Val Met Ser Leu Ser Lys Thr Met Val Val Val Leu Gln
1               5                   10                  15

Val Met Ile Leu Leu Gly Gln Glu Ile Gly Lys Val Ser Ser Thr Leu
            20                  25                  30

Tyr Lys Val Gly Asp Leu Asp Ala Trp Gly Ile Pro Ile Asp Ala Lys
        35                  40                  45

Val Tyr Ser Lys Trp Pro Lys Ser His Ser Phe Lys Ile Gly Asp Ser
    50                  55                  60

Leu Leu Phe Leu Tyr Pro Pro Ser Glu Asp Ser Leu Ile Gln Val Thr
65                  70                  75                  80

Pro Ser Asn Phe Lys Ser Cys Asn Thr Lys Asp Pro Ile Leu Tyr Met
                85                  90                  95

Asn Asp Gly Asn Ser Leu Phe Asn Leu Thr Gln Asn Gly Thr Leu Tyr
            100                 105                 110

Phe Thr Ser Ala Asn Pro Gly His Cys Thr Lys Tyr Gln Lys Leu Leu
        115                 120                 125

Val Ser Val Gly Thr Tyr Ser Ala Glu Ala Glu Ala Leu Ser Pro Ser
    130                 135                 140

Ser Ala Ala Asp Ala Pro Ser Tyr Gln Asn Ala Phe Gly Ser Ile Pro
145                 150                 155                 160

Leu Ser Gln Lys Ser Ser Ala Ser Ser Ser Leu Ile Ser Ala Phe Ser
                165                 170                 175

Thr Val Ala Ala Ser Leu Ala Cys Ala Val Val Gly Ala Ile Met
            180                 185                 190
```

<210> SEQ ID NO 138
<211> LENGTH: 684
<212> TYPE: DNA
<213> ORGANISM: Glycine max

<400> SEQUENCE: 138

```
agccagactc gagccaataa taagtccttg gcgagatcac tatatctaaa gaaaagagtg    60
aagattaatg tgagtgcaat tttgaataga accaagatgg ccatttttc aagtcaccac    120 agaatgttgg tgtctctctt gcttacgttg gtccaaatcc aagccaaggt gttttgctat    180
caatacaaag tgggagatct agatgcttgg ggcatacccca catcagcaaa tccacaagtc    240
tacacaaaat ggtccaaata tcataatctc acaattggag actcccttt atttctatac    300 ccaccaagtc aagattcagt gattcaagtt acagaggaat cctacaagag gtgcaacatt    360
aaagacccga tattgtacat gaacaatggc aactctttgt ttaacattac atcaaagggc    420
caattcttct tcactagtgg tgagcctggc cattgccaaa aaaatcaaaa gcttcatata    480
```

-continued

```
tctgttggtg aaggaataat agaaactatg gatacagcac ctggtccaag ttcgtcattg    540
cctgcatctg caccctccta tcccacagta tttggcaata ttccagtagc tccttcaacc    600
tcaacctcac ctcaactcac atcaactttt caacttctca tcattggatt tatgatatgt    660
gcgcacttcg cttccttaat gtga                                          684
```

<210> SEQ ID NO 139
<211> LENGTH: 227
<212> TYPE: PRT
<213> ORGANISM: Glycine max

<400> SEQUENCE: 139

```
Ser Gln Thr Arg Ala Asn Asn Lys Ser Leu Ala Arg Ser Leu Tyr Leu
1               5                   10                  15

Lys Lys Arg Val Lys Ile Asn Val Ser Ala Ile Leu Asn Arg Thr Lys
            20                  25                  30

Met Ala Ile Phe Ser Ser His His Arg Met Leu Val Ser Leu Leu Leu
        35                  40                  45

Thr Leu Val Gln Ile Gln Ala Lys Val Phe Cys Tyr Gln Tyr Lys Val
    50                  55                  60

Gly Asp Leu Asp Ala Trp Gly Ile Pro Thr Ser Ala Asn Pro Gln Val
65                  70                  75                  80

Tyr Thr Lys Trp Ser Lys Tyr His Asn Leu Thr Ile Gly Asp Ser Leu
                85                  90                  95

Leu Phe Leu Tyr Pro Pro Ser Gln Asp Ser Val Ile Gln Val Thr Glu
            100                 105                 110

Glu Ser Tyr Lys Arg Cys Asn Ile Lys Asp Pro Ile Leu Tyr Met Asn
        115                 120                 125

Asn Gly Asn Ser Leu Phe Asn Ile Thr Ser Lys Gly Gln Phe Phe Phe
    130                 135                 140

Thr Ser Gly Glu Pro Gly His Cys Gln Lys Asn Gln Lys Leu His Ile
145                 150                 155                 160

Ser Val Gly Glu Gly Ile Ile Glu Thr Met Asp Thr Ala Pro Gly Pro
                165                 170                 175

Ser Ser Ser Leu Pro Ala Ser Ala Pro Ser Tyr Pro Thr Val Phe Gly
            180                 185                 190

Asn Ile Pro Val Ala Pro Ser Thr Ser Thr Ser Pro Gln Leu Thr Ser
        195                 200                 205

Thr Phe Gln Leu Leu Ile Ile Gly Phe Met Ile Cys Ala His Phe Ala
    210                 215                 220

Ser Leu Met
225
```